(12) United States Patent
Ghosh

(10) Patent No.: US 7,687,252 B2
(45) Date of Patent: Mar. 30, 2010

(54) PROTEIN CRYSTAL OF HUMAN CYTOCHROME P450 AROMATASE AND USES THEREOF

(75) Inventor: Debashis Ghosh, Getzville, NY (US)

(73) Assignee: Hauptman-Woodward Medcial Research Institute, Inc., Buffalo, NY (US)

( * ) Notice: Subject to any disclaimer, the term of this patent is extended or adjusted under 35 U.S.C. 154(b) by 0 days.

(21) Appl. No.: 12/265,709

(22) Filed: Nov. 5, 2008

(65) Prior Publication Data

US 2009/0204378 A1     Aug. 13, 2009

Related U.S. Application Data

(60) Provisional application No. 60/985,471, filed on Nov. 5, 2007, provisional application No. 61/033,131, filed on Mar. 3, 2008, provisional application No. 61/101,928, filed on Oct. 1, 2008.

(51) Int. Cl.
*C12N 9/02* (2006.01)
*C12Q 1/26* (2006.01)
*G01N 33/483* (2006.01)

(52) U.S. Cl. .......................... 435/189; 435/25; 702/19

(58) Field of Classification Search ........................ None
See application file for complete search history.

(56) References Cited

U.S. PATENT DOCUMENTS

2006/0142360 A1    6/2006 Potter et al.

OTHER PUBLICATIONS

International Search Report and Written Opinion from PCT/US2008/082536, mailed Mar. 26, 2009.
Loge, C. et al., "Three-Dimensional Model of Cytochrome P450 Human Aromatase," *Journal of Enzyme Inhibition and Medicinal Chemistry*, Dec. 2005, vol. 20, Issue 6, pp. 581-585.
Kellis, J. et al., "Inhibition of Human Estrogen Synthetase (Aromatase) by Flavones," *Science*, Sep. 7, 1984, vol. 225, No. 4666, pp. 1032-1034.
Chen, S. et al., "Structure-Function Studies of Aromatase and Its Inhibitors: A Progress Report," *Journal of Steroid Biochemistry & Molecular Biology*, Sep. 2003, vol. 86, Issue 3-5, pp. 231-237.
Hong, Y. et al., "Molecular Basis for the Aromatization Reaction and Exemestane-Mediated Irreversible Inhibition of Human Aromatase," *Molecular Endocrinology*, Feb. 2007, vol. 21, Issue 2, pp. 401-414.

*Primary Examiner*—Nashaat T Nashed
(74) *Attorney, Agent, or Firm*—Heslin Rothenberg Farley & Mesiti P.C.

(57) ABSTRACT

The present invention relates to a protein crystal of at least one binding site of a human aromatase. The present invention also relates to a fully processed human cytochrome P450 aromatase and a protein crystal thereof. The present invention further relates to methods of making and using the aromatase and the protein crystal thereof.

28 Claims, 17 Drawing Sheets
(10 of 17 Drawing Sheet(s) Filed in Color)

SEQUENCE LISTING

<160> NUMBER OF SEQ ID NOS: 1

<210> SEQ ID NO 1
<211> LENGTH: 503
<212> TYPE: PRT
<213> ORGANISM: Homo sapiens

<400> SEQUENCE: 1

Met Val Leu Glu Met Leu Asn Pro Ile His Tyr Asn Ile Thr Ser Ile
1               5                   10                  15

Val Pro Glu Ala Met Pro Ala Ala Thr Met Pro Val Leu Leu Leu Thr
            20                  25                  30

Gly Leu Phe Leu Leu Val Trp Asn Tyr Glu Gly Thr Ser Ser Ile Pro
        35                  40                  45

Gly Pro Gly Tyr Cys Met Gly Ile Gly Pro Leu Ile Ser His Gly Arg
    50                  55                  60

Phe Leu Trp Met Gly Ile Gly Ser Ala Cys Asn Tyr Tyr Asn Arg Val
65                  70                  75                  80

Tyr Gly Glu Phe Met Arg Val Trp Ile Ser Gly Glu Glu Thr Leu Ile
                85                  90                  95

-continued

```
Ile Ser Lys Ser Ser Ser Met Phe His Ile Met Lys His Asn His Tyr
        100                 105                 110
Ser Ser Arg Phe Gly Ser Lys Leu Gly Leu Gln Cys Ile Gly Met His
        115                 120                 125
Glu Lys Gly Ile Ile Phe Asn Asn Pro Glu Leu Trp Lys Thr Thr
        130                 135                 140
Arg Pro Phe Phe Met Lys Ala Leu Ser Gly Pro Gly Leu Val Arg Met
145                 150                 155                 160
Val Thr Val Cys Ala Glu Ser Leu Lys Thr His Leu Asp Arg Leu Glu
                165                 170                 175
Glu Val Thr Asn Glu Ser Gly Tyr Val Asp Val Leu Thr Leu Leu Arg
                180                 185                 190
Arg Val Met Leu Asp Thr Ser Asn Thr Leu Phe Leu Arg Ile Pro Leu
                195                 200                 205
Asp Glu Ser Ala Ile Val Val Lys Ile Gln Gly Tyr Phe Asp Ala Trp
                210                 215                 220
Gln Ala Leu Leu Ile Lys Pro Asp Ile Phe Phe Lys Ile Ser Trp Leu
225                 230                 235                 240
Tyr Lys Lys Tyr Glu Lys Ser Val Lys Asp Leu Lys Asp Ala Ile Glu
                245                 250                 255
Val Leu Ile Ala Glu Lys Arg Arg Ile Ser Thr Glu Glu Lys Leu
                260                 265                 270
Glu Glu Cys Met Asp Phe Ala Thr Glu Leu Ile Leu Ala Glu Lys Arg
                275                 280                 285
Gly Asp Leu Thr Arg Glu Asn Val Asn Gln Cys Ile Leu Glu Met Leu
                290                 295                 300
Ile Ala Ala Pro Asp Thr Met Ser Val Ser Leu Phe Phe Met Leu Phe
305                 310                 315                 320
Leu Ile Ala Lys His Pro Asn Val Glu Glu Ala Ile Ile Lys Glu Ile
                325                 330                 335
Gln Thr Val Ile Gly Glu Arg Asp Ile Lys Ile Asp Asp Ile Gln Lys
                340                 345                 350
Leu Lys Val Met Glu Asn Phe Ile Tyr Glu Ser Met Arg Tyr Gln Pro
                355                 360                 365
Val Val Asp Leu Val Met Arg Lys Ala Leu Glu Asp Asp Val Ile Asp
                370                 375                 380
Gly Tyr Pro Val Lys Lys Gly Thr Asn Ile Ile Leu Asn Ile Gly Arg
385                 390                 395                 400
Met His Arg Leu Glu Phe Phe Pro Lys Pro Asn Glu Phe Thr Leu Glu
                405                 410                 415
Asn Phe Ala Lys Asn Val Pro Tyr Arg Tyr Phe Gln Pro Phe Gly Phe
                420                 425                 430
Gly Pro Arg Gly Cys Ala Gly Lys Tyr Ile Ala Met Val Met Met Lys
                435                 440                 445
Ala Ile Leu Val Thr Leu Leu Arg Arg Phe His Val Lys Thr Leu Gln
                450                 455                 460
Gly Gln Cys Val Glu Ser Ile Gln Lys Ile His Asp Leu Ser Leu His
465                 470                 475                 480
Pro Asp Glu Thr Lys Asn Met Leu Glu Met Ile Phe Thr Pro Arg Asn
                485                 490                 495
Ser Asp Arg Cys Leu Glu His
                500
```

PROTEIN CRYSTAL OF HUMAN CYTOCHROME P450 AROMATASE AND USES THEREOF

CROSS-REFERENCE TO RELATED APPLICATIONS

This application claims the benefit of U.S. Provisional Patent Application Ser. No. 60/985,471, filed Nov. 5, 2007, U.S. Provisional Patent Application Ser. No. 61/033,131, filed Mar. 3, 2008, and U.S. Provisional Patent Application Ser. No. 61/101,928, filed Oct. 1, 2008, all of which are hereby incorporated by reference in their entirety.

GOVERNMENT RIGHTS STATEMENT

The present invention was made with U.S. Government support under National Institutes of Health (NIH) Grant No. GM62794 and NIH Grant No. GM59450. The U.S. Government has certain rights in the invention.

FIELD OF THE INVENTION

The present invention relates to a protein crystal of at least one binding site of a human aromatase. The present invention also relates to a fully processed human cytochrome P450 aromatase and a protein crystal thereof. The present invention also relates to methods of making and using the aromatase and the protein crystal thereof.

BACKGROUND OF THE INVENTION

As used herein, citations to references are indicated in brackets, and are further described in the "References Cited" listing contained herein.

Enzymes that catalyze biosynthesis of steroid hormones in human are mainly cytochrome P450s and non-metallo dehydrogenases/reductases [A1]. Cytochrome P450's are members of a superfamily of heme-containing enzymes present both in eukaryotes and prokaryotes [A2]. Human cytochrome P450's have 18 gene families and 44 subfamilies. Cytochrome P450 Aromatase is the product of the CYP19A1 gene on chromosome 15q21.1, which has one family and one subfamily. The class I cytochrome P450s are mitochondrial and receive electrons via an iron-sulfur protein adrenodoxin and a flavoprotein adrenodoxin reductase. Class II enzymes, on the other hand, are residents of the endoplasmic reticulum/golgi system and use the flavoprotein cytochrome P450 reductase (CPR) to receive electrons from NADPH. Of the 57 human sequenced cytochrome P450 genes, 7 belong to Class I, and 50 to class II [A3,4].

Cytochrome P450 Aromatase (henceforth Aromatase) is one of the most important class II cytochrome P450s involved in steroid biosynthesis. Aromatase uses with high specificity androstenedione, testosterone, and 16α-hydroxytestosterone (all with the same androgen backbone) as substrates converting them to estrone, 17β-estradiol, and 17β,16α-estriol (all with the same estrogen backbone), respectively. It is the only known enzyme in vertebrates capable of catalyzing the aromatization of a six-membered ring. The functional human enzyme is monomeric, comprised of a heme group and a single polypeptide chain of 503 amino-acid residues (molecular mass about 55 kDa). It is an integral membrane protein of the endoplasmic reticulum, anchored to the membrane by an amino terminal transmembrane domain [A5-7], in addition to other membrane-associating regions.

Many soluble bacterial cytochrome P450s including P450cam [A8], P450BM-3 [A9], P450terp [A10], and P450eryF [A11], have been crystallized and structures determined by X-ray crystallography. In recent times, crystal structures of several recombinant, microsomal human cytochrome P450s (PDB ID codes: 1A2, 2A6, 2A13, 2C8, 2C9, 2D6, 2R1 and 3A4) have been determined [A12-16 and references therein]. Nearly all of these P450s catalyze metabolism of a wide variety of endogenous and xenobiotic compounds and drugs with low substrate specificities.

Being the sole catalyst for a unique hydroxylation, carbon-carbon bond cleavage and ring aromatization reaction step in the estrogen biosynthesis pathway, Aromatase has been the subject of intense biochemical and biophysical investigations for the past 35 years [see A7, 17, 18 for reviews]. Nevertheless, many aspects of the Aromatase catalyzed reaction, especially the third aromatization step, remain poorly understood. Lack of a crystal structure of Aromatase has led to a number of homology models for the enzyme based on other experimental P450 structures and site-directed mutagenesis data [A19-30 and references therein]. Several androgen-binding scenarios at the active site, possible involvements of side chains in the catalytic process, as well as models for enzyme's mechanism of action have been proposed based on these structural and functional analyses [A20-24, 27-29]. However, validation of all these results necessitated an experimental three-dimensional model of the enzyme showing the binding mode of the steroidal substrate and its interactions with active side amino acids. Additionally, because inhibition of estrogen biosynthesis by Aromatase inhibitors (AI) constitutes one of the foremost therapies for postmenopausal estrogen-dependent breast cancer today [A30-32], details of the substrates and inhibitor binding interactions at the active site have become increasingly critical information for the development of next generation AIs.

Despite concerted efforts in many laboratories, no experimental molecular structure of Aromatase has emerged yet. The major impediments to Aromatase crystallization have been its strong hydrophobic character, and susceptibility to rapid denaturation in the absence of the protective lipid bilayer. Furthermore, recombinant DNA techniques have also thus far been unsuccessful in producing the enzyme in qualities and quantities suitable for crystallization. A number of laboratories have reported purification of aromatase from human placenta [A33-35] and recombinant expression systems [A30, 36]. Nevertheless, attempts to crystallize either the placental or a recombinant/modified aromatase have been unsuccessful and an experimental aromatase structure has remained elusive. Numerous mechanistic/homology models based on known P450 structures and site-directed mutagenesis data have been proposed [A19-30], none of which could satisfactorily explain the functional data or enzyme action. Using term human placenta as a rich source of Aromatase and an elegant purification technique that employs a highly specific monoclonal antibody-based affinity chromatography [A37], we have been able to purify large quantities of the enzyme in a pristine, active form that has permitted the growth of diffraction-quality single crystals under suitable detergent conditions.

Therefore, there is a need for a purification and crystallization procedure that can yield a crystal of at least one binding site of a human aromatase, thereby providing a crystal and associated data and information that can be used to design and screen for drugs and new compounds for treating androgen-dependent breast cancer and for modulating estrogen biosynthesis. The present invention is useful in addressing this and other needs.

SUMMARY OF THE INVENTION

One aspect of the present invention relates to a crystal having at least one ligand binding site of a human aromatase. In one embodiment, the human aromatase can include, without limitation, an amino acid sequence of SEQ ID NO:1 or a functional mutant or variant thereof. In a further embodiment, the crystal is of a fully processed human aromatase of SEQ ID NO:1 or a functional mutant or variant thereof.

One aspect of the present invention relates to a composition that includes any one of the crystals of the present invention.

The present invention also relates to an isolated human cytochrome P450 aromatase, where the aromatase is isolated from human placental tissue and is effective in maintaining catalytic activity during crystallization. In one embodiment, the isolated human cytochrome P450 aromatase can include, without limitation, an amino acid sequence according to SEQ ID NO:1 or an active mutant or variant thereof. Methods of isolating and purifying the isolated human cytochrome P450 aromatase of the present invention are further described herein.

Another aspect of the present invention relates to a method for crystallizing a human aromatase. This method is effective in crystallizing a human aromatase having an amino acid sequence according to SEQ ID NO:1 or an active mutant or variant thereof. This method involves providing an isolated human aromatase of the present invention. The isolated human aromatase is incubated in a detergent solution under conditions effective to stabilize the human aromatase for crystallization. In one embodiment, the detergent can include, without limitation, n-dodecyl-β-D-maltopyranoside (BDM) and n-nonyl-β-D-maltopyranoside (BNM). The stabilized human aromatase is then crystallized in a crystallization solution that includes, without limitation, dithiothreitol (DTT) and a ligand under conditions effective to yield a crystallized human aromatase in complex with the ligand.

A further aspect of the present invention relates to methods for designing or screening for a drug for use in treating estrogen-dependent breast cancer or for use in inhibiting estrogen biosynthesis. In one embodiment, this method involves obtaining a three-dimensional representation of at least one ligand binding site of a human aromatase. Thereafter, at least one candidate ligand compound is superimposed on the three-dimensional representation of the ligand binding site. The binding of the at least one candidate compound and the ligand binding site is evaluated. Thereafter, a compound that spatially fits the ligand binding site is selected as a drug that can be used in treating estrogen-dependent breast cancer or for use in inhibiting estrogen biosynthesis.

Another aspect of the present invention relates to a method for screening for a novel drug that inhibits aromatase activity in humans. This method involves selecting a candidate compound by performing rational drug design using a three-dimensional structure determined from the crystal of the present invention. The candidate compound is contacted with at least one ligand binding site of a human aromatase or a functional equivalent of the ligand binding site. The binding potential of the candidate compound for the ligand binding site or the functional equivalent thereof is detected. According to this method, the candidate compound is selected based on its having a greater affinity for the ligand binding site or a functional equivalent thereof than that of a known drug.

Another aspect of the present invention relates to a method for designing a candidate drug that interferes with an activity of a human aromatase. This method involves providing a three-dimensional crystal structure of the isolated human cytochrome P450 aromatase of the present invention in complex with a ligand, where the ligand is bound to at least a portion of a ligand binding site of the human aromatase. Thereafter, a step of designing a compound predicted to bind the human aromatase configured in the human aromatase and ligand complex is performed.

Another aspect of the present invention relates to a method for designing a compound that interferes with an activity of a human aromatase. This method involves providing on a digital computer a three-dimensional structure of at least one ligand binding site of the isolated human cytochrome P450 aromatase of the present invention. Thereafter, software that includes the digital computer is used to design a compound that is predicted to bind to at least a portion of the at least one ligand binding site of the human aromatase. This method can also include the steps of synthesizing the compound using techniques known in the art and then evaluating the compound for an ability to interfere with an activity of the human aromatase.

A further aspect of the present invention relates to a high throughput enzymatic assay method for screening candidate compounds that inhibit human aromatase. This method involves testing a plurality of candidate compounds for human aromatase binding activity, where each compound is tested by the method previously described method for designing or screening for a drug for use in treating estrogen-dependent breast cancer or for use in inhibiting estrogen biosynthesis.

One aspect of the present invention relates to a three-dimensional computer image of the three-dimensional structure of human aromatase-ligand complex, where the human aromatase includes an isolated human cytochrome P450 aromatase of the present invention and has a three-dimensional structure that substantially conforms to the three-dimensional atomic coordinates of Appendix A.

A further aspect of the present invention relates to a computer-readable medium encoded with a set of three-dimensional atomic coordinates of a crystal according to the present invention, so that by using a graphical display software program, the three-dimensional atomic coordinates of the crystal create an electronic file that can be visualized on a computer capable of representing the electronic file as a three-dimensional image.

The present invention provides a human Aromatase and an X-ray crystal structure of the Aromatase. The Aromatase of the present invention has a number of attributes, some of which are summarized as follows. The Aromatase of the present invention is a unique human cytochrome P450 that has low (<20%) sequence homology with other P450s (e.g., human P450s 2A6, 3A4, etc., and bacterial P450cam, P450eryF, etc.). The Aromatase has an amino-terminal segment that is longer than other human P450s. The amino-terminal polypeptide (~100 amino acids) bears even lower sequence homology (<10%) with other P450s. The amino terminus of Aromatase is extremely hydrophobic and membrane integrated. The Aromatase of the present invention is highly selective of androgens as substrates, unlike many human microsomal drug- and xenobiotics-metabolizing P450s, such as 2D6 and 3A4, which are promiscuous with regard to the substrate selectivity. Aromatase is the only enzyme in the vertebrate world that specifically catalyzes the biosynthesis of estrogens from androgens. There is no other known pathway for estrogen biosynthesis. Aromatase (CYP19A1) is the first cytochrome P450 in the steroid hormone biosynthesis pathway to be crystallized. Other such P450s are CYP21, CYP17, but none of them has been crystallized. Aromatase is the first natural and full-length human P450 to be crystallized. All other human microsomal P450s crystallized, including 2D6 and 3A4, are synthetically prepared and modified by the recombinant DNA technology.

Over the period of past 20 years, similar initiatives to prepare amino-terminal deleted and/or otherwise modified Aromatase by various recombinant expression systems and to obtain diffraction-quality crystals have been unsuccessful. Numerous theoretical atomic models of Aromatase based on biochemical and biophysical data, as well as bioinformatics/homology approach have been published in the literature. None of these even remotely resembles the active site structure derived from the current X-ray crystallographic elucidation. Unlike the open active sites of many microsomal P450s that metabolize drugs and xenobiotics such as 2D6 and 3A4, the X-ray crystal structure of Aromatase reveals a unique androgen-binding cleft that snuggly fits the androstenedione molecule, exquisitely complemented by hydrophobic and polar amino acids The present invention is useful in overcoming the deficiencies in the prior art.

BRIEF DESCRIPTION OF DRAWINGS

The patent or application file contains at least one drawing executed in color. Copies of this patent or patent application publication with color drawings will be provided by the U.S. Patent and Trademark Office upon request and payment of the necessary fee.

DETAILED DESCRIPTION OF THE INVENTION

Figure 1:
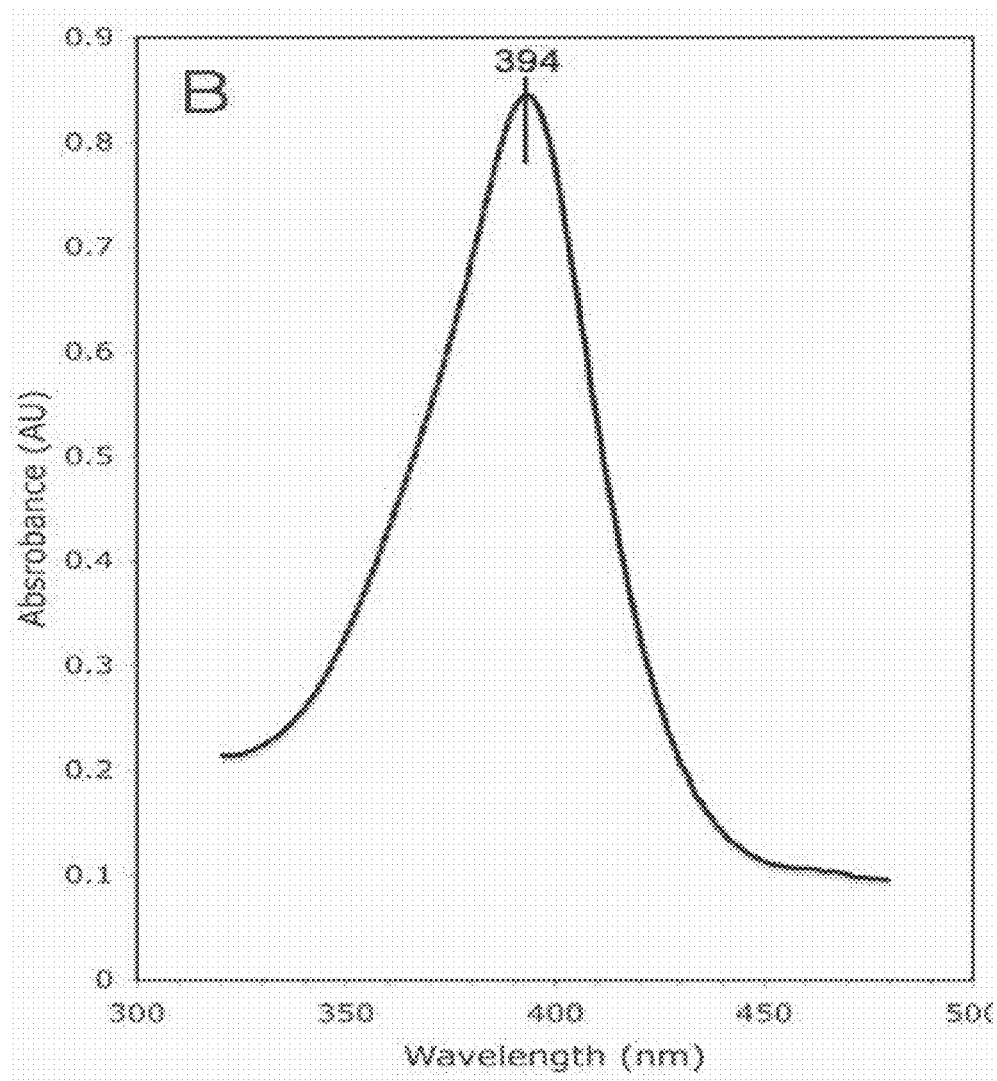
FIG. 1 is a graphical representation of an absorption spectrum of purified Aromatase showing a Soret peak at 394 nm, suggestive of the formation of the high spin Ferric-androstenedione complex.

The present invention relates to the crystal structure of human placental aromatase, which is described in more detail herein below. The atomic coordinates and structure factor files have been deposited with the Protein Data Bank under the accession code 3EQM, and are hereby incorporated by reference in their entirety. The atomic coordinates are also submitted herewith as a .txt file as Appendix A, which is hereby incorporated by reference in its entirety.

In one embodiment, the isolated human cytochrome P450 Aromatase has an amino acid sequence according to SEQ ID NO:1, as follows:

```
Met Val Leu Glu Met Leu Asn Pro Ile His Tyr Asn Ile Thr Ser Ile Val Pro

Glu Ala Met Pro Ala Ala Thr Met Pro Val Leu Leu Leu Thr Gly Leu Phe Leu

Leu Val Trp Asn Tyr Glu Gly Thr Ser Ser Ile Pro Gly Pro Gly Tyr Cys Met

Gly Ile Gly Pro Leu Ile Ser His Gly Arg Phe Leu Trp Met Gly Ile Gly Ser

Ala Cys Asn Tyr Tyr Asn Arg Val Tyr Gly Glu Phe Met Arg Val Trp Ile Ser

Gly Glu Glu Thr Leu Ile Ile Ser Lys Ser Ser Ser Met Phe His Ile Met Lys

His Asn His Tyr Ser Ser Arg Phe Gly Ser Lys Leu Gly Leu Gln Cys Ile Gly

Met His Glu Lys Gly Ile Ile Phe Asn Asn Asn Pro Glu Leu Trp Lys Thr Thr

Arg Pro Phe Phe Met Lys Ala Leu Ser Gly Pro Gly Leu Val Arg Met Val Thr

Val Cys Ala Glu Ser Leu Lys Thr His Leu Asp Arg Leu Glu Glu Val Thr Asn

Glu Ser Gly Tyr Val Asp Val Leu Thr Leu Leu Arg Arg Val Met Leu Asp Thr

Ser Asn Thr Leu Phe Leu Arg Ile Pro Leu Asp Glu Ser Ala Ile Val Val Lys

Ile Gln Gly Tyr Phe Asp Ala Trp Gln Ala Leu Leu Ile Lys Pro Asp Ile Phe

Phe Lys Ile Ser Trp Leu Tyr Lys Lys Tyr Glu Lys Ser Val Lys Asp Leu Lys

Asp Ala Ile Glu Val Leu Ile Ala Glu Lys Arg Arg Arg Ile Ser Thr Glu Glu

Lys Leu Glu Glu Cys Met Asp Phe Ala Thr Glu Leu Ile Leu Ala Glu Lys Arg

Gly Asp Leu Thr Arg Glu Asn Val Asn Gln Cys Ile Leu Glu Met Leu Ile Ala

Ala Pro Asp Thr Met Ser Val Ser Leu Phe Phe Met Leu Phe Leu Ile Ala Lys

His Pro Asn Val Glu Glu Ala Ile Ile Lys Glu Ile Gln Thr Val Ile Gly Glu

Arg Asp Ile Lys Ile Asp Asp Ile Gln Lys Leu Lys Val Met Glu Asn Phe Ile
```

-continued

```
Tyr Glu Ser Met Arg Tyr Gln Pro Val Val Asp Leu Val Met Arg Lys Ala Leu

Glu Asp Asp Val Ile Asp Gly Tyr Pro Val Lys Lys Sly Thr Asn Ile Ile Leu

Asn Ile Gly Arg Met His Arg Leu Glu Phe Phe Pro Lys Pro Asn Glu Phe Thr

Leu Glu Asn Phe Ala Lys Asn Val Pro Tyr Arg Tyr Phe Gln Pro Phe Gly Phe

Gly Pro Arg Gly Cys Ala Gly Lys Tyr Ile Ala Met Val Met Met Lys Ala Ile

Leu Val Thr Leu Leu Arg Arg Phe His Val Lys Thr Leu Gln Gly Gln Cys Val

Glu Ser Ile Gln Lys Ile His Asp Leu Ser Leu His Pro Asp Glu Thr Lys Asn

Met Leu Glu Met Ile Phe Thr Pro Arg Asn Ser Asp Arg Cys Leu Glu His
```

The Aromatase of SEQ ID NO:1 is a full-length polypeptide having 503 amino acid residues. As used herein, the term "Aromatase" is also referred to without italics and without capitalization. Further, the term "P450arom" is used herein to describe a human cytochrome P450 aromatase of the present invention.

In one embodiment of the crystal of the present invention, the three-dimensional structure model thereof is based on residues 45-496 of SEQ ID NO:1, because of the weak electron densities associated with residues 1-44 and 497-503 of SEQ ID NO:1. were not included in the model because of their weak electron densities.

In one aspect of the present invention, various sites of the Aromatase structure can be targeted for the design and synthesis of next generation Aromatase inhibitors (AIs). One such target site includes the substrate-specific distal heme active site, which is unique among all P450s. A second site, which also appears to be Aromatase-specific, is the active site access channel that leads the substrate from within the membrane bilayer to the active site cleft. Compounds that specifically block this channel would constitute an effective and novel class of AIs. A third site includes the heme proximal site where cytochrome P450 reductase couples with Aromatase, and compounds designed to target this site will make another new class of Aromatase inhibitors. A fourth site is the catalytic machinery to which a transition state analog compound can be covalently linked, with the compounds designed to target this site providing specific, but longer-lasting inhibition, a desirable drug property in the clinical setting.

Various substrates (also referred to herein as "ligands") of the human Aromatase of the present invention can be co-crystallized to yield Aromatase-substrate complexes. Suitable substrates include, but are not limited to, the following: androstenedione; testosterone; 19-hydroxyandrostenedione; 16α-hydroxytestosterone; exemestane; 7,8-benzoflavone; apigenin; chrysin; 19-aldoandrostenedione; 19-hydroxytestosterone; letrozole; anastrazole; and analogs or derivatives thereof.

Androstenedione: This is the first of the three androgenic substrates that Aromatase uses. Androstenedione is converted to estrone by Aromatase. The structure of the androstenedione-complex of Aromatase has elucidated the molecular basis of substrate specificity that is hallmark of Aromatase. This knowledge, along with similar information from other enzyme-substrate and enzyme-inhibitor complexes, can be utilized in the design and synthesis of more specific, exclusive and novel inhibitors of Aromatase.

Testosterone: This is the second androgen that Aromatase catalyzes by converting it to estradiol. This complex can be used to identify any structural and chemical differences among the three androgens in their binding interactions at the Aromatase active site.

19-Hydroxyandrostenedione: This is the postulated reaction intermediate of the first hydroxylation step by Aromatase. This complex will help us to trace the catalytic pathway, understand the stereo-specific nature of catalysis, and design novel inhibitors that mimic the stereo-specificity of the reaction intermediates without being catalyzed.

16α-Hydroxytestosterone: This is a third androgenic substrate that is converted to estriol by Aromatase.

Exemestane: This is the only steroidal inhibitor of the three FDA-approved breast cancer drugs known as Aromatase inhibitors (AIs). The structural, molecular, and chemical basis of their inhibitory action has remained largely unknown. Therefore, the use of the Aromatase crystal of the present invention can be useful in gathering knowledge that is critical to the development of the next generation AIs.

7,8-Benzoflavone, Apigenin, and Chrysin: These three compounds are flavones that were shown to be competitive inhibitors of Aromatase, i.e., they compete with substrate-binding at the active site (see Kellis J T, Vickery L E (1984) Inhibition of human Aromatase by flavones. Science 225, 1032-1034). The present invention contemplates Aromatase-specific modification of plant (dietary) flavones, thereby converting them to be effective AIs.

19-Aldoandrostenedione: This compound is the postulated reaction intermediate of the second hydroxylation step of androstenedione-to-estrone catalysis by Aromatase.

19-Hydroxytestosterone: This compound is the postulated reaction intermediate of the first hydroxylation step of testosterone-to-estradiol conversion by Aromatase.

Letrozole and Anastrazole: These are the other two FDA-approved AIs. However, in contrast to exemestane, these are non-steroidal compounds and their Aromatase binding modes are more speculative. The mechanism of inhibition by these two compounds quite possibly is different from that by exemestane, and hence the use of the crystal structures of the Aromatase in complex with these compounds is very useful.

Other complexes of Aromatase: The present invention contemplates the co-crystallization with Aromatase and study by X-ray crystallography and other biochemical methods any new inhibitors designed and synthesized by our group, and/or identified by virtual in silico screening and docking methods. The entire procedure will follow an iterative process of design, synthesis and evaluation for improving the affinity, specificity, and inhibition and anti-proliferative properties of the compound concerned.

One aspect of the present invention relates to a crystal having at least one ligand binding site of a human aromatase.

In one embodiment, the human aromatase can include, without limitation, an amino acid sequence of SEQ ID NO:1 or a functional mutant or variant thereof. In a further embodiment, the crystal is of a fully processed human aromatase of SEQ ID NO:1 or a functional mutant or variant thereof.

As used herein the term "ligand binding site" can include any portion of the human aromatase of the present invention to which a ligand or a portion of a ligand can bind. More particularly, suitable ligand binding sites of the present invention include, without limitation, an active/substrate-binding heme distal site of human aromatase, a heme proximal/P450 reductase coupling site of human aromatase, and functional mutants or variants thereof.

Suitable active/substrate-binding heme distal sites can further include, without limitation, the following portions of the amino acid sequence of SEQ ID NO:1 (or a functional mutant or variant thereof): residues Arg115 through Phe147; residues Ile217 through Leu228; residues Leu301 through Ser314; residues Pro368 through Arg375; and residues Ile474 through His480. Suitable active/substrate-binding heme distal sites can also include combinations of these portions of the amino acid sequence of SEQ ID NO:1 and/or functional mutants and variants of these portions of the amino acid sequence of SEQ ID NO:1.

Suitable heme proximal/P450 reductase coupling sites can further include, without limitation, the following portions of the amino acid sequence of SEQ ID NO:1 (or a functional mutant or variant thereof): residues Arg145 through Met149; residues Glu357 through Met364; and residues Pro423 through Met447. Suitable heme proximal/P450 reductase coupling sites can also include combinations of these portions of the amino acid sequence of SEQ ID NO:1 and/or functional mutants and variants of these portions of the amino acid sequence of SEQ ID NO:1.

Another aspect of the present invention relates to a crystal that includes at least one ligand binding site of a human aromatase and that further includes an active site access channel.

As used herein, an active site access channel can include, without limitation, the following portions of the amino acid sequence of SEQ ID NO:1 (or a functional mutant or variant thereof): residues Asp186 through Arg193; residues Gln218 through Leu228; residues Pro308 through Phe317; residues Pro368 through Leu372; and residues Gln472 through Lys485. Suitable active site access channels can also include combinations of these portions of the amino acid sequence of SEQ ID NO:1 and/or functional mutants and variants of these portions of the amino acid sequence of SEQ ID NO:1. Further, an access channel according to the present invention can include, for example, an interior protein border that includes at least amino acid residues Arg192, Asp309, Ser478, and Glu483 of SEQ ID NO:1 (or a functional mutant or variant thereof).

Another aspect of the present invention relates to a crystal that includes a space group of $P3_221$ and unit cell parameters of a=b=140.2 Å, c=119.3 Å, $\alpha=\beta=90°$, and $\gamma=120°$.

Another aspect of the present invention relates to a crystal that includes a three-dimensional structure described by atomic coordinates that substantially conform to the following atomic coordinates: (i) coordinates 553 through 821, 1359 through 1459, 2062 through 2161, 2611 through 2673, and 3468 through 3535 as set forth in Appendix A; (ii) coordinates 1112 through 1179, 1367 through 1459, 2113 through 2191, 2611 through 2647, and 3450 through 3565 as set forth in Appendix A; and/or (iii) coordinates 793 through 840, 2508 through 2578, and 3057 through 3257 as set forth in Appendix A.

Another aspect of the present invention relates to a crystal that includes a three-dimensional structure described by atomic coordinates that substantially conform to atomic coordinates corresponding to SEQ ID NO:1 as set forth in Appendix A, or to atomic coordinates corresponding to a functional mutant or variant of SEQ ID NO:1.

According to the present invention, the use of the term "substantially conform" (or variations thereof) refers to at least a portion of a three-dimensional structure of a human aromatase or human aromatase-ligand complex that is sufficiently spatially similar to at least a portion of a specified three-dimensional configuration of a particular set of atomic coordinates (e.g., those included in Appendix A) to allow the three-dimensional structure of a human aromatase or human aromatase-ligand complex to be modeled or calculated using the particular set of atomic coordinates as a basis for determining the atomic coordinates defining the three-dimensional configuration of a human aromatase or human aromatase-ligand complex.

Another aspect of the present invention relates to a crystal that includes at least one ligand binding site of a human aromatase and that further includes a ligand in complex with the human aromatase. In one embodiment, at least a portion of the ligand is: (i) bound to at least a portion of the at least one ligand binding site, where the ligand binding site includes an active site of the human aromatase; (ii) bound to the human aromatase at a location so as to block an access channel to the at least one ligand binding site, where the ligand is either bound to at least a portion of the ligand binding site or not bound to at least a portion of the ligand binding site; (iii) bound to the human aromatase at a location so as to block coupling of a cytochrome P450 reductase to the human aromatase; and/or (iv) covalently linked to a catalytic region of the human aromatase, where the catalytic region can include, without limitation, Ala306, Asp309, and/or Thr310 of SEQ ID NO:1 (or a functional mutant or variant thereof), or a heme Fe associated with the human aromatase.

As used herein, the term "ligand" refers to any compound or agent that can bind to at least a portion of a ligand binding site of the human aromatase of the present invention. More particularly, suitable ligands can include, without limitation, an androgenic substrate of human aromatase, an androgenic substrate intermediate of human aromatase, and a competitive inhibitor of human aromatase. Suitable androgenic substrates of human aromatase can include, without limitation, androstenedione, testosterone, 16α-hydroxytestosterone, and analogs or derivatives thereof. Suitable androgenic substrate intermediates of human aromatase can include, without limitation, 19-hydroxyandrostenedione, 19-aldoandrostenedione, 19-hydroxytestosterone, and analogs or derivatives thereof. Suitable competitive inhibitors of human aromatase can include, without limitation, exemestane, 7,8-benzoflavone, apigenin, chrysin, letrozole, anastrazole, formestane, fadrozole, aminoglutethimide, and analogs or derivatives thereof. Suitable ligands of the present invention can also include, without limitation, a transition state analog compound that is covalently linked to human aromatase.

In one embodiment of the present invention, the active site of the human aromatase can include, without limitation, the following amino acid residues of SEQ ID NO:1 (or a functional mutant or variant thereof): Arg115, Ile133, Phe134, Phe221, Trp224, Ala306, Asp309, Thr310, Val370, Val373, Met374, and/or Leu477. The active site can further include combinations of these amino acid residues.

In another embodiment, the active site can also include, without limitation, a catalytic cleft of the human aromatase of the present invention. The catalytic cleft can include, without limitation, the following amino acid residues of SEQ ID NO:1 (or a functional mutant or variant thereof): Ile133, Phe134, Ile305, Ala306, Asp309, Thr310, Val370, Leu372, Val373, Met374, Leu477, and/or Ser478.

In a further embodiment, the active site can additionally include, without limitation, the following amino acid residues of SEQ ID NO:1 (or a functional mutant or variant thereof): Arg192, Gln218, Gln225, Leu228, Pro308, Met311, and/or Glu483.

In yet a further embodiment, the active site can include, without limitation, three-dimensional regions of SEQ ID NO:1 (or a functional mutant or variant thereof), as follows: (i) an I-helix comprising Ile305, Ala306, Asp309, and/or Thr310; (ii) a B-C loop comprising Ile133 and Phe134; (iii) a K-helix-β3-loop comprising Val370, Leu372, and Val373; (iv) a β3 segment comprising Met374; and/or (v) a β8-β9 loop comprising Leu477 and Ser378.

As described hereinabove, one aspect of the present invention relates to a crystal that includes at least one ligand binding site of a human aromatase and that further includes a ligand in complex with the human aromatase. In a particular embodiment of this aspect of the present invention, the ligand is an androstenedione bound to at least a portion of an active site of the human aromatase. More particularly, the crystal is sufficiently pure to determine atomic coordinates of the human aromatase-ligand (e.g., androstenedione) complex by X-ray diffraction to a resolution of 2.90 Å or better than 2.90 Å (e.g., at least at a resolution of 2.70 Å).

One aspect of the present invention relates to a composition that includes any one of the crystals of the present invention.

The present invention also relates to an isolated human cytochrome P450 aromatase, where the aromatase is isolated from human placental tissue and is effective in maintaining catalytic activity during crystallization. In one embodiment, the isolated human cytochrome P450 aromatase can include, without limitation, an amino acid sequence according to SEQ ID NO:1 or an active mutant or variant thereof. Methods of isolating and purifying the isolated human cytochrome P450 aromatase of the present invention are further described herein.

Another aspect of the present invention relates to a method for crystallizing a human aromatase. This method is effective in crystallizing a human aromatase having an amino acid sequence according to SEQ ID NO:1 or an active mutant or variant thereof. This method involves providing an isolated human aromatase of the present invention. The isolated human aromatase is incubated in a detergent solution under conditions effective to stabilize the human aromatase for crystallization. In one embodiment, the detergent can include, without limitation, n-dodecyl-β-D-maltopyranoside (BDM) and n-nonyl-β-D-maltopyranoside (BNM). The stabilized human aromatase is then crystallized in a crystallization solution that includes, without limitation, dithiothreitol (DTT) and a ligand under conditions effective to yield a crystallized human aromatase in complex with the ligand.

In one embodiment of this method, the DTT is present during crystallization at a concentration of between about 10 mM and 20 mM. In another embodiment, the method of crystallizing a human aromatase is carried out at a temperature ranging from about 3° C. to about 6° C., preferably at about 4° C. Further, the method can be carried out in the presence of a protectant that is effective to maintain the aromatase in its natural fold. In view of the disclosure set forth herein, including in the Examples section, one of ordinary skill in the art would understand the types of protectants that can be used.

In another embodiment of this method, a further step can include solubilization of the ligand in a polyethylene glycol solution (or functional equivalent thereof) prior to the incubating step, thereby increasing yield of the crystallized aromatase-ligand complex.

Another aspect of the present invention relates to a crystallized human aromatase prepared according to the method for crystallizing a human aromatase, as described herein.

The successful crystallization of the human aromatase of the present invention has made it possible to use the human aromatase crystal, portions of the crystal, and various data and information relating to the crystal for a wide variety of uses. Before the present invention, such uses were not feasible. Various uses of the crystal are contemplated by the present invention, and are set forth herein below. Some of the terms used to describe the methods of use have been described or further defined herein, and the meaning of such terms apply with regard to the below methods of use.

In view of the above, a further aspect of the present invention relates to methods for designing or screening for a drug for use in treating estrogen-dependent breast cancer or for use in inhibiting estrogen biosynthesis. In one embodiment, this method involves obtaining a three-dimensional representation of at least one ligand binding site of a human aromatase. Thereafter, at least one candidate ligand compound is superimposed on the three-dimensional representation of the ligand binding site. The binding of the at least one candidate compound and the ligand binding site is evaluated. Thereafter, a compound that spatially fits the ligand binding site is selected as a drug that can be used in treating estrogen-dependent breast cancer or for use in inhibiting estrogen biosynthesis.

In one embodiment of this method, the three-dimensional representation of the at least one ligand binding site of the human aromatase can be determined from a crystal or co-crystal of the human aromatase.

In another embodiment of this method, a further step of obtaining or synthesizing the selected compound can be performed according to techniques known in the art and further described herein. After obtaining or synthesizing the selected compound, the compound can be contacted to at least one ligand binding site of the human aromatase to determine the ability of the selected compound to interact with the ligand binding site of the human aromatase.

In a further embodiment of this method, a further step of obtaining or synthesizing the selected compound can be performed according to techniques known in the art and further described herein. After obtaining or synthesizing the selected compound, a complex of the at least one ligand binding site of the human aromatase and the selected compound can be formed according to techniques known in the art and further described herein. Thereafter, the complex can be analyzed to determine the ability of the selected compound to interact with the at least one ligand binding site of the human aromatase.

Another aspect of the present invention relates to a method for screening for a novel drug that inhibits aromatase activity in humans. This method involves selecting a candidate compound by performing rational drug design using a three-dimensional structure determined from the crystal of the present invention. The candidate compound is contacted with at least one ligand binding site of a human aromatase or a functional equivalent of the ligand binding site. The binding potential of the candidate compound for the ligand binding site or the functional equivalent thereof is detected. According to this method, the candidate compound is selected based on its having a greater affinity for the ligand binding site or a functional equivalent thereof than that of a known drug.

Another aspect of the present invention relates to a method for designing a candidate drug that interferes with an activity of a human aromatase. This method involves providing a three-dimensional crystal structure of the isolated human cytochrome P450 aromatase of the present invention in complex with a ligand, where the ligand is bound to at least a portion of a ligand binding site of the human aromatase. Thereafter, a step of designing a compound predicted to bind the human aromatase configured in the human aromatase and ligand complex is performed.

Another aspect of the present invention relates to a method for designing a compound that interferes with an activity of a human aromatase. This method involves providing on a digital computer a three-dimensional structure of at least one ligand binding site of the isolated human cytochrome P450 aromatase of the present invention. Thereafter, software that includes the digital computer is used to design a compound that is predicted to bind to at least a portion of the at least one ligand binding site of the human aromatase. This method can also include the steps of synthesizing the compound using techniques known in the art and then evaluating the compound for an ability to interfere with an activity of the human aromatase.

In one embodiment of this method, the evaluating step can include, without limitation, assaying the compound for anti-proliferative activity. According to the present invention, anti-proliferative activity can include inhibiting growth of a breast cancer cell line under an estrogenic stimulus. A suitable breast cancer cell line for use in this method can include, without limitation, MCF-7. However, other known cancer cell lines can also be used and are contemplated by the present invention.

A further aspect of the present invention relates to a high throughput enzymatic assay method for screening candidate compounds that inhibit human aromatase. This method involves testing a plurality of candidate compounds for human aromatase binding activity, where each compound is tested by the method previously described method for designing or screening for a drug for use in treating estrogen-dependent breast cancer or for use in inhibiting estrogen biosynthesis.

In one embodiment of this method, the testing step involves evaluating binding affinity of the compound by direct measurement of the association constant using a isothermal titration calorimeter.

In another embodiment of this method, the testing step involves evaluating anti-proliferative activity of the compound as an aromatase inhibitor in a breast cancer cell line expressing aromatase and an estrogen receptor.

In yet another embodiment of this method, the testing step involves determining X-ray crystallographic structures of at least one reaction intermediate of estrogen biosynthesis by initiating hydroxylation reaction in a crystal with X-ray photoelectrons and following the shift in the Soret band with a micro-spectrophotometer suitable for in situ measurement in protein crystals.

One aspect of the present invention relates to a three-dimensional computer image of the three-dimensional structure of human aromatase-ligand complex, where the human aromatase includes an isolated human cytochrome P450 aromatase of the present invention and has a three-dimensional structure that substantially conforms to the three-dimensional atomic coordinates of Appendix A.

A further aspect of the present invention relates to a computer-readable medium encoded with a set of three-dimensional atomic coordinates of a crystal according to the present invention, so that by using a graphical display software program, the three-dimensional atomic coordinates of the crystal create an electronic file that can be visualized on a computer capable of representing the electronic file as a three-dimensional image.

The present invention is illustrated by the following examples.

EXAMPLES

The following examples are intended to illustrate particular embodiments of the present invention, but are by no means intended to limit the scope of the present invention.

Example 1

Optimized Methodology for the Purification of Human Aromatase from Term Placenta in Quality and Quantity Suitable for Crystallization A. Aromatase Purification Protocol An example of one embodiment of the Aromatase purification protocol of the present invention is set forth below:

Preparation of Placental Homogenate:
1. Obtain fresh human placenta from Women's and Children's Hospital, Buffalo, N.Y.
2. Remove chorionic plate and sac, preserving internal tissue.
3. Cut tissue into pieces and rinse with 1% KCl+67 mM $PO_4$ pH7.4.
4. Blot tissue with paper towels.
5. Weigh on pan balance.
6. To tissue—add ½ wet weight of SDP Buffer (all buffers are described in section E below)
   Example: 300 g tissue—add 150 ml buffer
7. Homogenize solution 2×30 sec. at full speed.
8. Measure volume of homogenate and store at −80° C. until further need.

Day 1—Aromatase Purification:
1. Remove in A.M. appropriate homogenate sample(s) and thaw at 4° C. overnight.
2. Check all buffers:
   Buffer A (no Em) [−Em; Em: Emulgen 913, a detergent]
   Buffer A (+Em) [+Em: 10% Em]
3. Wash and equilibrate mAb column with ~50 ml Buffer A (+Em)

Day 2 (Start: 7:30 am; Finish ~3:30-4:00 pm):
1. Homogenize thawed sample on high for 60 sec
2. Bring the homogenate volume to 800-900 ml (for 600 to 700 g placentas)] with Buffer A (−Em)
   Remove ⅛X aliquot (50 ml sample 350 ml Buffer A (−Em)) and label as "homogenate"
3. Centrifuge homogenate at 35,000 rpm using 45Ti rotor at 4° C. for 50 minutes
4. Repeat step 3 until all homogenate is used
5. Discard supernatant
6. Homogenize pellets with 600-700 ml (for 600 to 700 g placentas)] Buffer A (−Em)
7. Adjust the homogenate volume to 700-850 ml (for 600 to 700 g placentas)] with Buffer A (−Em)
   Remove ⅛ X aliquot (50 ml sample 350 ml Buffer A (−Em)) and label as "105 Kg ppt"
8. Add such that the final concentration is 0.3% of the following stocks to the 105 kg ppt:
   10% Em (22.3 for 700 ml) (26.2 ml for 850 ml)

10% Sodium Cholate (22.3 ml for 700 ml) (26.2 ml for 850 ml)
9. Stir homogenate for 1 hour
10. Centrifuge homogenate at 35,000 rpm using 45Ti rotor at 4° C. for 55 min
11. Repeat step 10 until all 105 kg ppt is used
12. Save and measure volume of supernatant
13. Discard pelleted debris
14. To supernatant—add equal volume of Buffer A (−Em) Remove 50 µl sample and label as "Extract"
15. Apply sample to pre-equilibrated mAb column and run o/n
   Flow rate=1.7 ml/min (clamp at green hash mark on bar)
   Start loading at ~1:30-2 pm
   Make sure "safety" line is attached to bottom of column
   No monitor hook-up
16. Start in A.M. equilibration of G-25 (2.5×95 cm) column with ~800 ml Buffer A (+Em)+0.5 mM DTT (any buffers containing DTT MUST be made fresh and protected from air)
   DTT: Dithiothreitol Day 3 (Start: 6:30 am; Finish ~2:30 pm):
1. Finish loading any remaining extract
   If any remaining, disconnect safety line, and speed up the loading to ~2 ml/min
2. Wash mAb column with ~30 ml Buffer A (+Em) until "red" color is no longer visible on column
   Remove 50 µl sample label "mAb-ps"
3. Collect mAb column pass and wash and store at −80° C.
4. Wash column with ~50 ml 0.5M NaCl in Buffer A (+Em)
5. Hook column to monitor. Once the columns are hooked up from this point out, the flow rate is 0.5 ml/min
6. Elute Aromatase with 100 ml 4M NaCl in Buffer A (+Em)
   Collect fractions at 6 minutes/tube, chart speed 0.5, UV monitor 1, recorder range 10 mV
   Monitor baseline (set blue marker at 10 on recorder paper), adjust as needed
   Each fraction tube contains 3 ml Buffer A (+Em)+0.5 mM DTT
7. Immediately load pooled fractions onto pre-equilibrated G-25 (2.5×95 cm) column
   Collect fractions at 8 minutes/tube, chart speed of 0.5, and UV monitor 0.5, recorder range 10 mV
   Don't start collecting fraction tubes until yellow color is ¾ through column
   Monitor baseline (set blue marker at 10 on recorder paper), adjust as needed
8. Elute with Buffer A (+Em)+0.5 mM DTT
9. Pool Aromatase fractions and store at 4° C. on ice
10. Run UV scan from Optical Density at 350 nm (OD350) to OD500 (P450scan method on nystar spec)
11. Regenerate mAb column with ~50 ml 0.2M Glycine in Buffer A (+Em) pH2.8
12. Wash mAb column with ~50 ml TBS+0.02% Sodium Azide for storage Hydroxyapatite Column Preparation (Day 3):
1. Weigh out 1.3 g Hydroxyapatite (HA) powder
2. Mix powder with 40 ml Buffer A (+Em)+0.5 mM DTT
3. Incubate for 20 minutes
4. Discard upper liquid phase
5. Repeat steps 3-4 with fresh 40 ml Buffer A (+Em)+0.5 mM DTT
6. Resuspend with 5 ml Buffer A (+Em)+0.5 mM DTT
7. Add slurry to 1.5 cm diameter column
8. Allow to settle for 10 to 15 minutes
9. Discard upper liquid phase and add fresh buffer
10. Continue to step 1 on day 4

Day 4 (Start: 7:30 am; Finish ~4:30 pm):
1. Prior to loading, again UV scan from OD350 to OD500 (P450scan method on nystar spec)
2. Load Aromatase onto HA column
   Flow rate: 2.0 ml/min (lower blue hash mark on bar)
3. Wash column with ~50 ml Buffer A (+Em)+0.5 mM DTT
   Flow rate: 2.5 ml/min (upper blue hash mark on bar)
4. Wash column with ~70 ml Buffer A (−Em)+0.5 mM DTT+2 mM BNM (OR 1 mM BDM)
   BNM: β-D-nonyl maltoside; BDM: β-D-dodecyl maltoside
   Place buffer at upper blue hash mark on bar
   Collect fractions at 10 minutes/tube, chart speed of 0.5, and UV monitor 0.1, recorder range 10 mV
   Monitor baseline (set blue marker at 10 on recorder paper), adjust as needed to make sure all of emulgen is removed
5. Turn off spigot to column and incubate column for 1 hour
6. Elute Aromatase with 200 mM $KPO_4$ in Buffer A (−Em)+0.5 mM DTT+1 mM BDM
   Collect fractions at 6 minutes/tube, chart speed 0.5, and UV monitor 1, recorder range 10 mV
   Monitor baseline (set blue marker at 10 on recorder paper), adjust as needed
   Each fraction tube contains 3 ml Buffer A (−Em)+0.5 mM DTT+1 mM BDM
7. Collect and pool Aromatase containing fractions
8. Divide eluted protein amongst several centricon ym30's (each holds 15 ml)
9. Concentrate to a volume of 2-3 ml eliminating centricons until only 1 is being used
10. Run sodium dodecylsulfate poly-acrylamide gel electrophoresis (SDS-PAGE) and UV scan from OD350 to OD500 (P450scan method on nystar spec) to estimate protein concentration
11. Adjust concentration of DTT to 20 mM
12. Adjust concentration of Andestenedione to 0.1 mM
13. Store at 4° C. on ice Day 5 (Start: 7:30 am; Finish ~3:30 pm):
1. Concentrate sample using Centricon ym30 to 1 ml
2. Perform Modified Lowry on all collected aliquots (if needed)
3. Remove 5 µl for activity assay
4. Record concentration with UV scan from OD350 to OD500 (P450scan method on nystar spec)
5. Concentrate using ym30 to a final volume such that the sample equals 30 mg/ml
6. Proceed to crystal set-up and final SDS-PAGE gel
7. Save sample for activity assay B. Assay of Enzyme Activity Purified Aromatase (0.20 µg) was reconstituted with 2 µg P450-reductase (CPR) and 20 µg 1,2-diarachidoyl-sn-glycero-3-phosphocholine. Reconstituted Aromatase was preincubated with 0.24 µM of the substrate, [1β-$^3$H, 4-$^{14}$C] androstenedione, with specific activity $2.7 \times 10^3$ dpm of $^3$H in 1 ml of 100 mM K-phosphate buffer at pH 7.4 containing 20% glycerol and 0.15% emulgen. Following preincubation at 37° C. for 1 min, the aromatase reaction was started by addition of 0.1 ml of 0.5 mM NADPH in 100 mM KPO4 buffer at pH 7.4 containing 20% glycerol. After shaking for 10 min at 37° C., the reaction was terminated by the addition of 0.4 ml of 20% trichloroacetic acid and 1.0 ml of 5% charcoal. After continued shaking at 37° C. for another 30 minutes, the mixture was centrifuged, and the supernatant is filtered through a cotton-plugged disposable Pasteur pipette. The $^3$H water in the eluate was assessed according to the 1β elimination mechanism (75% release into water) [A37]. The specific activity of the purified Aromatase was in the range 50-100 nmol/min/mg with Em as the detergent, one of the highest reported in the literature. The turnover number was calculated to be ~6/min. In the small molecule detergents BNM and BDM, the specific activity of Aromatase is retained at 80-90% levels at 4° C. for weeks.

C. Measurement of the Absorption Spectrum

Freshly purified Aromatase is concentrated to about 1-2 mg/ml (~0.02 mM). The concentration of androstenedione in solution was adjusted to 0.10 mM and the solution was incubated overnight. The absorption spectrum obtained from the resulting complex (FIG. 1) exhibits a Soret band at 394 nm, which is characteristic of oxidized Ferric ($Fe^{3+}$) state of the heme iron, suggesting the formation of the androstenedione-complex.

D. Typical Yield and Quality of the Purified Aromatase Preparations

Figure 2:
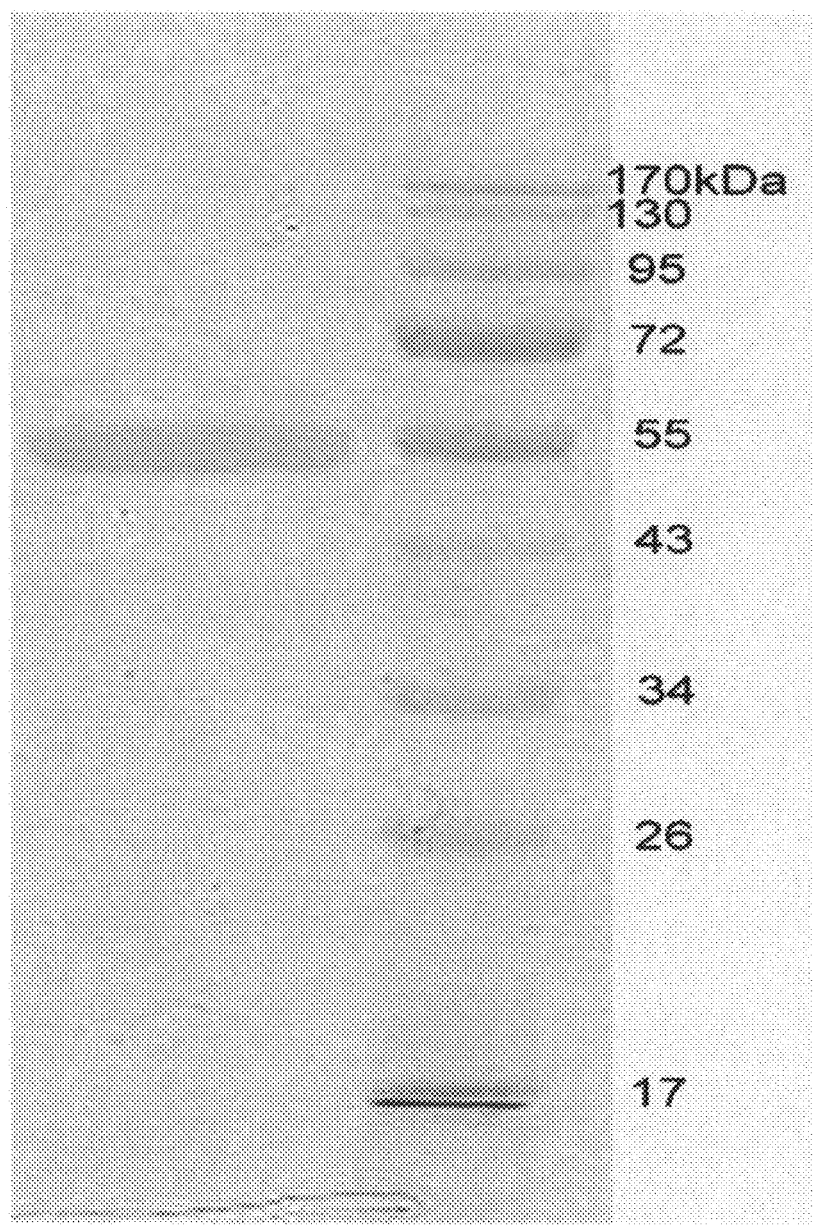
FIG. 2 is a depiction of a typical SDS-PAGE of purified Aromatase (15 μg).

FIG. 2 shows a silver-stained SDS-PAGE of the purified Aromatase product ready to undergo crystallization set-ups. Estimated purity from the gel ~99%+. Typical yield ~6-12 mg per placenta. Typical specific activity of the purified enzyme ~20-100 nmol/min/mg.

E. Buffer Recipes (All Buffers are Made and Kept at 4° C.)

Examples of various buffer recipes of the present invention are set forth below.

| | | Final concentration |
|---|---|---|
| Buffer A (−Em): 4 L volume | | |
| ****Add reagents in order below | | |
| 200 ml | $dH_2O$* | |
| 800 ml | 100% Glycerol* | 20% |
| 2948 ml | $dH_2O$ | |
| 40 ml | 1M $KPO_4$ | 10 mM |
| 10 ml | 200 mM Andestenedione | 0.5 μM |
| 2 ml | 200 mM EDTA | 0.1 mM |
| *In 1 L graduated cylinder add 200 ml $dH_2O$ then 800 ml glycerol. Rinse cylinder with remaining water volume | | |
| Buffer A (+Em): 4 L volume | | |
| ****Add reagents in order below | | |
| 200 ml | $dH_2O$* | |
| 800 ml | 100% Glycerol* | 20% |
| 2888 ml | $dH_2O$ | |
| 40 ml | 1M $KPO_4$ | 10 mM |
| 10 ml | 200 mM Andestenedione | 0.5 μM |
| 2 ml | 200 mM EDTA | 0.1 mM |
| 60 ml | 10% Emulgen913 | 0.15% |
| *In 1 L graduated cylinder add 200 ml $dH_2O$ then 800 ml glycerol. Rinse cylinder with remaining water volume | | |
| Buffer A (+Em) + DTT: 1.2 L volume (for g25) | | |
| 6 ml | 100 mM DTT* | 0.5 mM |
| *92.5 mg + 6 ml $dH_2O$ QS to 1.2 L with Buffer A(+Em) | | |
| Buffer A (+Em) + DTT: 200 ml volume (for HA) | | |
| 1 ml | 100 mM DTT* | 0.5 mM |
| *15.4 mg + 1 ml $dH_2O$ QS to 200 ml with Buffer A(+Em) | | |
| Buffer A (−Em) + 0.5 mM DTT + 1 mM BDM: 200 ml volume | | |
| 2 ml | DTT (30.8 mg + buffer)* | 100 mM |
| 102.1 mg | BDM (mw: 510.6) | 1 mM |
| QS to 100 ml with Buffer A(−Em) | | |
| *On Day 5: have 50 ml HA wash and HA Elute: add 250 ml of 100 mM DTT to each (final [DTT] = 0.5 mM) have 160 ml of Buffer A(−Em) + 0.5 mM DTT + 1 mM bDM: add 800 ml of 100 mM DTT to each (final [DTT] = 0.5 mM) | | |
| 200 mM $KPO_4$ in Buffer A (−Em) + 0.5 mM DTT + 1 mM BDM: 50 ml volume: | | |
| 10 ml | 1M $KPO_4$ | 200 mM |
| 40 ml | Buffer A (−Em) + 0.5 mM DTT + 1 mM BDM | |
| 0.067M $PO_4$: 4 L volume | | |
| 37.8 g | Sodium Phosphate Dibasic | |
| 784 ml | Potassium Phosphate Monobasic**** | |
| QS to 4 L with $dH_2O$ | | |
| ****9.1 g Potassium Phosphate Monobasic ($KH_2PO_4$) and QS to 1 L in volumetric flask **Store up to 4 weeks | | |
| 1% KCl in 0.067M $PO_4$: 4 L volume | | |
| 40 g | Potassium Chloride (KCl) | 1% |
| QS to 4 L with 0.067M $PO_4$ | | |

-continued

| | | Final concentration |
|---|---|---|
| SDP (Sucrose-DTT-Phosphate) Buffer: 1 L volume | | |
| 82 g | Sucrose | 240 mM |
| 5 ml | 100 mM DTT | 0.5 mM |
| QS to 1 L with 0.067M PO$_4$ | | |
| TBS: 1 L volume | | |
| 10 ml | 1M Tris pH 8.0 | 10 mM |
| 75 ml | 2M NaCl | 150 mM |
| 2 ml | 10% Na Azide | 0.02% |
| QS to 1 L dH$_2$O | | |
| 0.2M Glycine in Buffer A(+Em): 1 L volume | | |
| 15 g | Glycine | 0.2M |
| QS to 900 ml with Buffer A(+Em) | | |
| pH to 2.8 | | |
| QS to 1 L with Buffer A(+Em) | | |

Example 2

Optimization of Protein Solution, Buffer, Detergent, Precipitant, and Co-Precipitant Conditions This example describes various embodiments of optimal protein solutions, buffers, detergents, precipitant conditions, and co-precipitant conditions that yielded the diffraction-quality crystals of human Aromatase of the present invention, and the first crystallization of a native human cytochrome P450 enzyme purified from the tissue, and a cytochrome P450 enzyme in the steroid biosynthesis pathway.

A. Protein Concentration Optimization

Purified Aromatase concentration is measured both by the SDS-PAGE and OD spectrum scanned from 190 nm to 510 nm. The androstenedione complex of Aromatase has a Soret peak at 394 nm. Based on these measurements, the protein is then incubated with appropriate concentrations of DTT, substrates and/or inhibitors. It is then concentrated to a pre-determined final concentration. Final protein concentrations of 10, 20, 30, 32, 34, and 60 mg/ml were used in conjunction with commercial crystallization screens in search of a lead precipitant and buffer condition. The first protein concentration to give a crystallization hit was 20 mg/ml in 100 mM KPO4 pH 7.4, containing 10 mM DTT, 20% glycerol, 0.1 mM EDTA, 0.1 mM androstenedione, and 1 mM BDM. Further optimization of the concentration characteristically routinely yields diffraction-quality crystals at 30 to 34 mg/ml in 100 mM KPO4 buffer, pH 7.4, containing 20% glycerol, 0.1 mM EDTA, 0.1 mM Androstenedione, 1 mM BDM, and 20 mM DTT.

B. DTT Concentration Optimization

Purified Aromatase in the crystallization droplets tended to aggregate in the absence of a thiol-based reducing agent, such as DTT. Even about ~0.5 mM DTT could not prevent aggregation. In an experiment to evaluate the time stability of the purified enzyme undergoing crystallization at 4° C., various droplets each containing a different type of precipitate were harvested. The drops were originally set up in the presence of 0.5 mM and 5 mM DTT (after the initial mixing of crystallization cocktail the starting DTT concentrations were 0.25 mM and 2.5 mM, respectively). Precipitates were separated from the mother liquor and analyzed using SDS-PAGE. The protein incubated with 0.5 mM DTT showed visible signs of aggregation, while those precipitates with 5 mM DTT showed single, clean protein band. DTT concentration was then increased to 10, 20 and 30 mM with no decrease in activity. During crystal screening, it was determined through trial and error that 20 mM DTT was optimal for yielding diffraction-quality crystals.

C. Crystallization Condition Optimization

Initial commercial sparse crystal screens (Hampton Research (Aliso Viejo, Calif.), Nextal/Qiagen (Montreal, Canada/Valencia, Calif.); and Molecular Dimensions (Apopka, Fla.) were set up in a prop Volume Ratio (DVR) of 1 µl protein to 1 µl crystallization cocktail.

The following protocol was followed during the initial crystallization trials: (1) The crystallization screens were set-up in a 14° C. walk-in incubator room; the crystal drop boxes on ice and all reagents were chilled; (2) the protein/cocktail mixes were set-up using 24 well sitting drop Linbro plates and sealed with silicon grease; (3) once combined, the drops were observed and the Linbro boxes were stored in a 4° C. walk-in incubator room; (4) after 1 week of incubation, the drops were observed for any kind of crystalline formation; and (5) drops continued to be monitored and observed after weeks 2 and 4.

For any drops that showed the promise of forming crystals, the protein cocktails were altered for a finer crystallization screen.

Using a DVR of 1:1 (v/v) crystallization cocktail, a single crystallization cocktail gave the first Aromatase crystals. Under this condition the crystals grew from 0.5M NaCl, 50 mM Tris-HCl pH 8.5, 22% Polyethylene Glycol 4000 (PEG4000) at 4° C. Further optimization of this condition consistently yields diffraction-quality crystals. We now routinely grow diffraction-quality Aromatase crystals using cocktails containing: 24, 26, 28 and 30% PEG4000, each with 0.5M NaCl, 50 mM Tris-HCl pH 8.5 (at room temperature) at 2:1 (v/v), and 3:1 (v/v) DVRs respectively.

Figure 3:
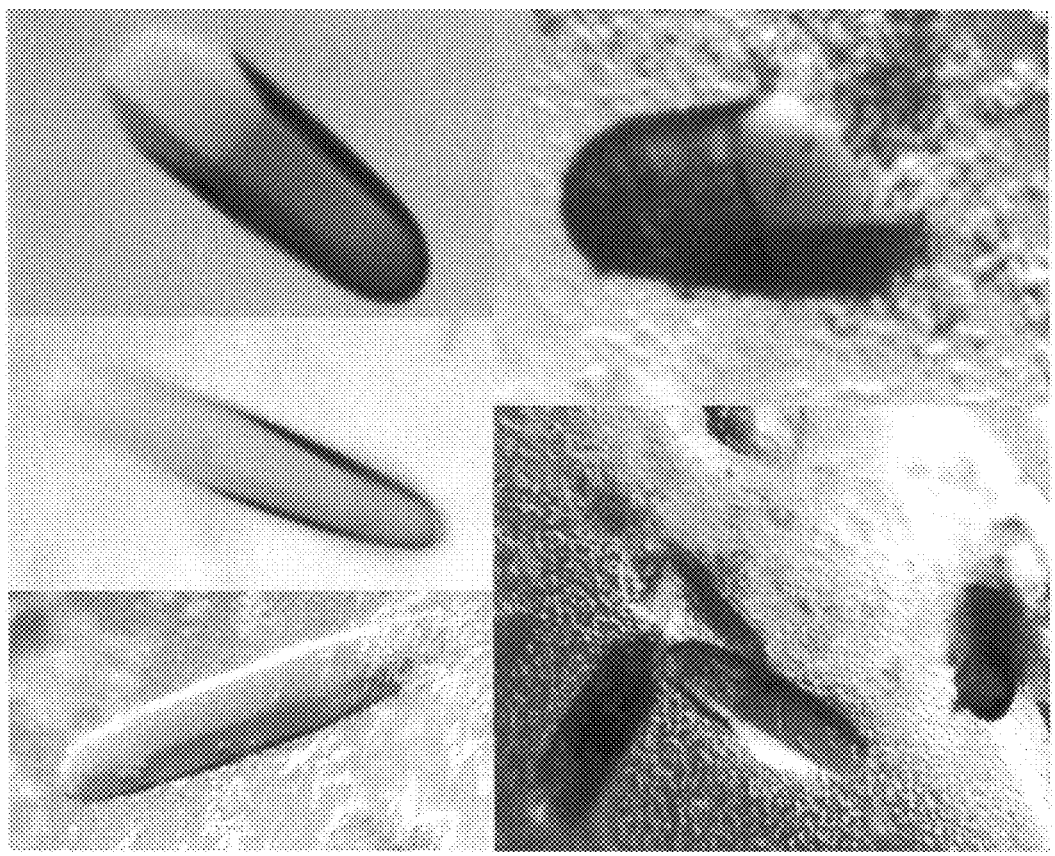
FIG. 3 shows crystals of human P450arom-androstenedione complex, grown from 3 different purification experiments. The hexagonal rod-shaped crystals shown here are ~0.30-0.50 mm in length and ~0.06-0.12 mm in cross-section.

Crystals under these conditions grow within 7-10 days at 4° C., and continue to grow up to 14-16 days. Typically between the first (7-10 days after initial set-up) and second evaluations (14-16 days after set-up), the crystal dimensions increase by 1.5 to 2 times in size. When fully grown, these brown-reddish colored hexagonal rod-shaped crystals (FIG. 3) have dimensions 0.10 mm to 0.50 mm in lengths and 0.05 mm to 0.15 mm in cross sections.

D. Crystals of Other Complexes of Aromatase

Diffraction-quality crystals have been successfully produced of Aromatase complexed with the following inhibitors and substrates: (1) 0.1 mM Androstenedione; (2) 0.2 mM Testosterone; (3) 0.2 mM 19-Hydroxyandrostenedione; (4) 0.3 mM 16α-Hydroxytestosterone; and (5) 0.4 mM Exemestane.

Crystallization of the following Aromatase complexes are under experimental study: (1) 0.2 mM 7,8-Benzoflavone; (2) 0.1 mM Apigenin; (3) 0.2 mM Chrysin; (4) 0.1 mM 19-Aldoandrostenedione; (5) 0.1 mM 19-Hydroxytestosterone; (6) 0.2 mM Letrozole; and (7) 0.2 mM Anastrazole.

Example 3

Diffraction Data Collection and Structure Solution

A. Diffraction Data Collection

Initially, diffraction data sets to about 3.3 Å resolution were collected at the A-1 station of the Cornell High Energy Synchrotron Source (CHESS). The A1 beam line receives monochromatic (double Si-crystal focused) X-rays from a 49-pole Wiggler at the fixed wavelength of 0.978 Å. The detector used for the entire diffraction experiment was ADSC Quantum-210 2X2 charge coupled detector (CCD). The crystals receive a flux of about $7.5\times10^{11}$ photon/second through a 200 μm collimator at the storage ring current of about 250 mA. The storage ring current decayed ~20% maximum over a period of 4 hours, and was replenished for the next run cycle. The crystals were cooled at cryogenic temperature by plunging them into liquid nitrogen and then maintaining them in a stream of liquid nitrogen at 100° K. Many different cryoprotectants were tried for this purpose. One that was best able to protect the integrity of the crystals was the crystal growth medium with the glycerol concentration adjusted to about 40%.

Figure 4:
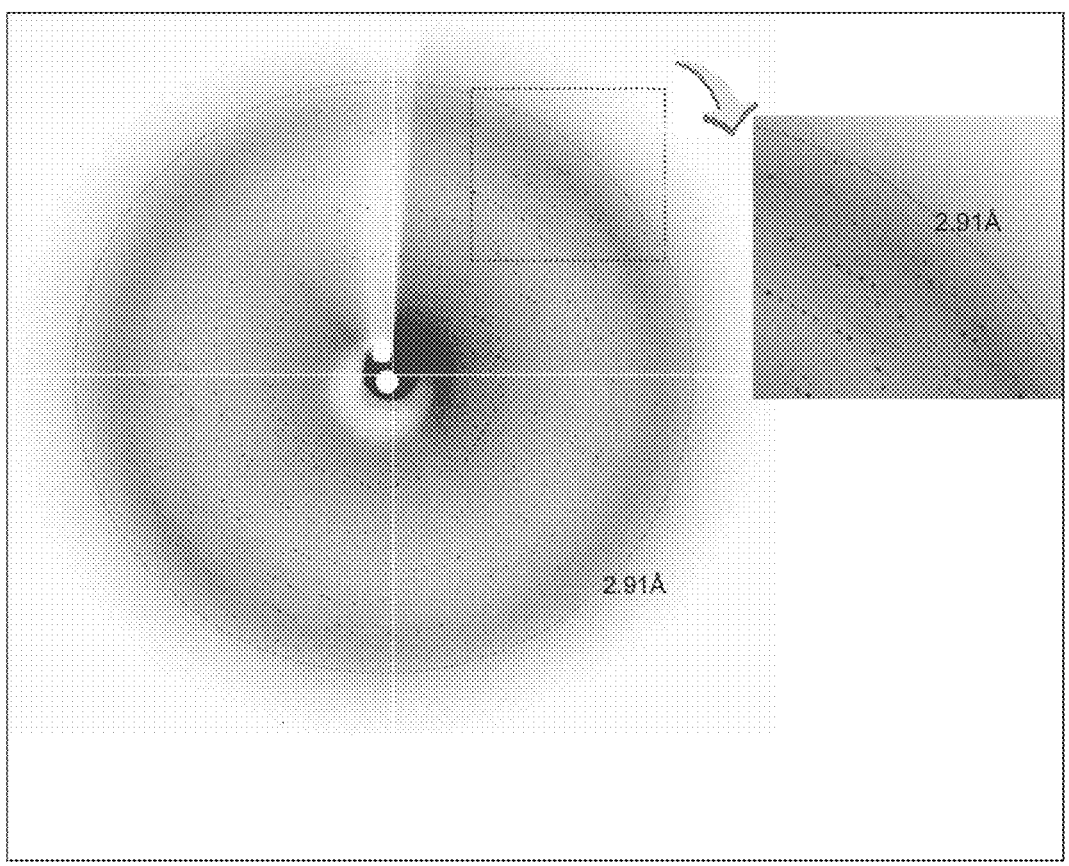
FIG. 4 is a diffraction image recorded from a crystal of human P450arom at the A1 beam line of the Cornell High Energy Synchrotron Source. Detector distance: 250 mm, wavelength: 0.978 Å, exposure time: 10 second, oscillation angle: 1°, detector used: ADSC Quantum-210 2X2 CCD. A section of image at the higher resolution side is magnified to show the limiting resolution.

Four complete diffraction data sets were collected with highest resolutions ranging between 2.9 and 3.4 Å. Although some of the crystals displayed diffraction spots up to 2.9 Å (FIG. 4), owing to the radiation damage the diffraction became progressively weaker between 2.9 and 3.2 Å, and the data at this range is weak and incomplete. Each frame of data represented of 1° oscillation of the crystal. Each data set consisted of a minimum of 120 to a maximum of 180 data frames. The data was processed with HKL2000 [A38] software package. The crystal belongs to the space group $P3_221$ with unit cell parameters a=b=140.17 Å, c=119.43 Å, α=β=90°, γ=120°. The crystal was flash cooled in a stream of liquid nitrogen using about 40% glycerol as the cryoprotectant, and maintained at ~100K during data collection. Additionally, two data sets, each to 4.2 Å resolution, were measured at the CHESS F-2 station by tuning the beam to the peak and the inflexion point of the iron absorption edge [Inflection (1.7433 Å): total 31833, unique 9814, completion 97%, I/sigI highest resolution 4.1, Rmerge 0.159. Remote (1.7284 Å): total 32671, unique 9903, completion 98%, I/sigI highest resolution 4.6, Rmerge 0.126].

Finally, a complete 2.9 Å diffraction dataset used for the solution and refinement of the structure was gathered at the beamline 19-ID-D of the Advanced Photon Source, Argonne National Laboratory, Argonne, Ill. The data was recorded on an ADSC Q315 CCD detector and processed with HKL3000 software package [A38]. The space group is $P3_221$ and the unit cell parameters are a=b=140.2 Å, c=119.3 Å, α=β=90°, γ=120°. There is one aromatase molecule in the asymmetric unit, with a solvent content of about 79%. A total of 184,295 diffraction intensities were measured yielding 30,371 unique reflections. The diffraction data was 99.4% complete to 2.90 Å resolution with an overall Intensity to sigma ratio of 31.1 and $R_{merge}$ of 0.067. The intensity to sigma ratio was 2.8 in the highest resolution shell. Table 1 summarizes the diffraction data statistics

TABLE 1

Data collection and structure refinement summary

| Description | Data/Stastics |
|---|---|
| Data frames, oscillation angle, exposure time | 200, 1°, 15 sec |
| Wavelength, number of crystals used | 0.979 Å, 1 |
| Total number of observations | 184,295 |
| Space group and unit cell | $P3_221$ |
| | a = b = 140.2 Å, |
| | c = 119.3 Å, |
| | α = β = 90°, γ = 120° |
| Resolution range | 50.0 Å-2.90 Å |
| Number of unique reflections | 30,371 |
| Completion percentage (in highest shell) | 99.4 (99.7) |
| Intensity/standard dev. (in highest shell) | 31.1 (2.8) |
| R-merge (in highest shell) | 0.067 (0.479) |
| Wilson plot B-value | 94.5 Å$^2$ |
| Molecules in asymm. unit, residues, protein atoms | 1, 452, 3767 |
| Heme and ligand atoms, waters, phosphates | 64, 35, 2 (10 atoms) |
| R-factor for all data (in highest shell) | 0.214 (0.315) |
| Free R-factor for 5% data (in highest shell) | 0.244 (0.362) |
| Average isotropic B-value | 77.3 Å$^2$ |
| RMSD from ideal bond distance, angle | 0.009 Å, 1.32° |
| Overall random coordinate error | 0.33 Å (based on R), |
| | 0.26 Å (on R-free), |
| | 0.19 Å (on max. likelihood) |
| Ramachandran plot summary | Allowed 405 |
| (407 non-glycine and non-proline residues) | Not allowed 2 |

B. Structure Determination and the Refined Model

Figure 5:
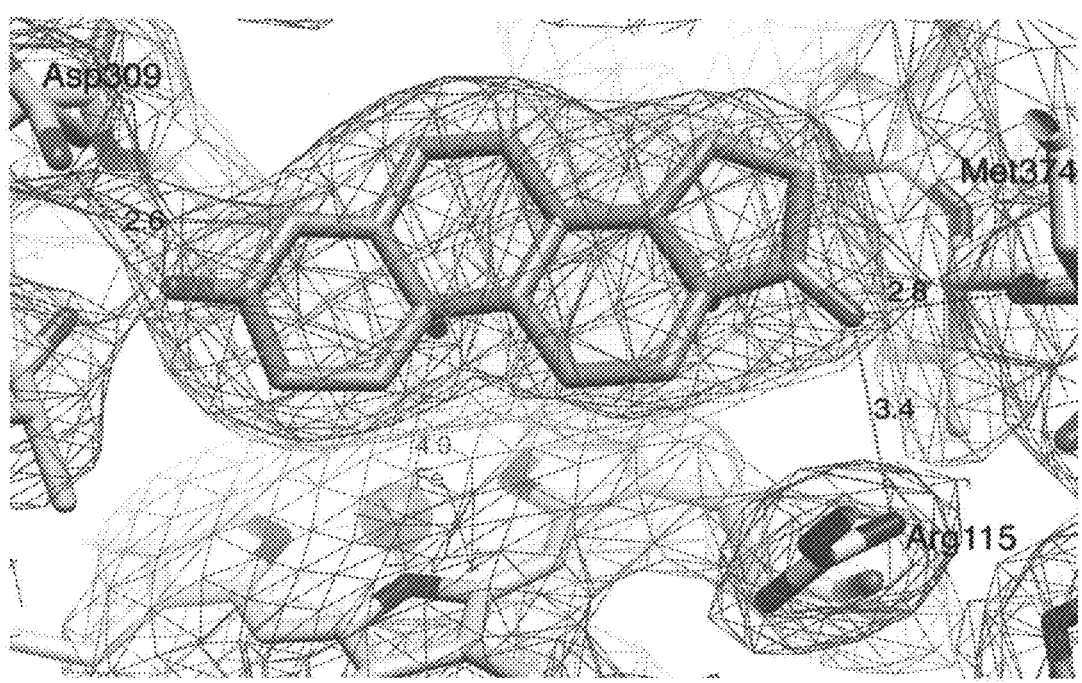
FIG. 5 shows the unbiased electron density for the bound androstenedione molecule viewed perpendicular to the steroid backbone. Colored in magenta is the (Fobs−Fcalc) difference electron density contoured at 4.5 times the standard deviation, and blue the (2Fobs−Fcalc) electron density contoured at 1.2 times the standard deviation, both are completely unbiased, calculated before the inclusion of the substrate atoms in the model. Contacting residues and heme atoms are shown in element colors: gray (carbon), blue (nitrogen), red (oxygen), and firebrick (Fe). The carbon atoms of androstenedione are colored in cornflower blue. The contact distances are shown in angstrom (Å).
Figure 6:
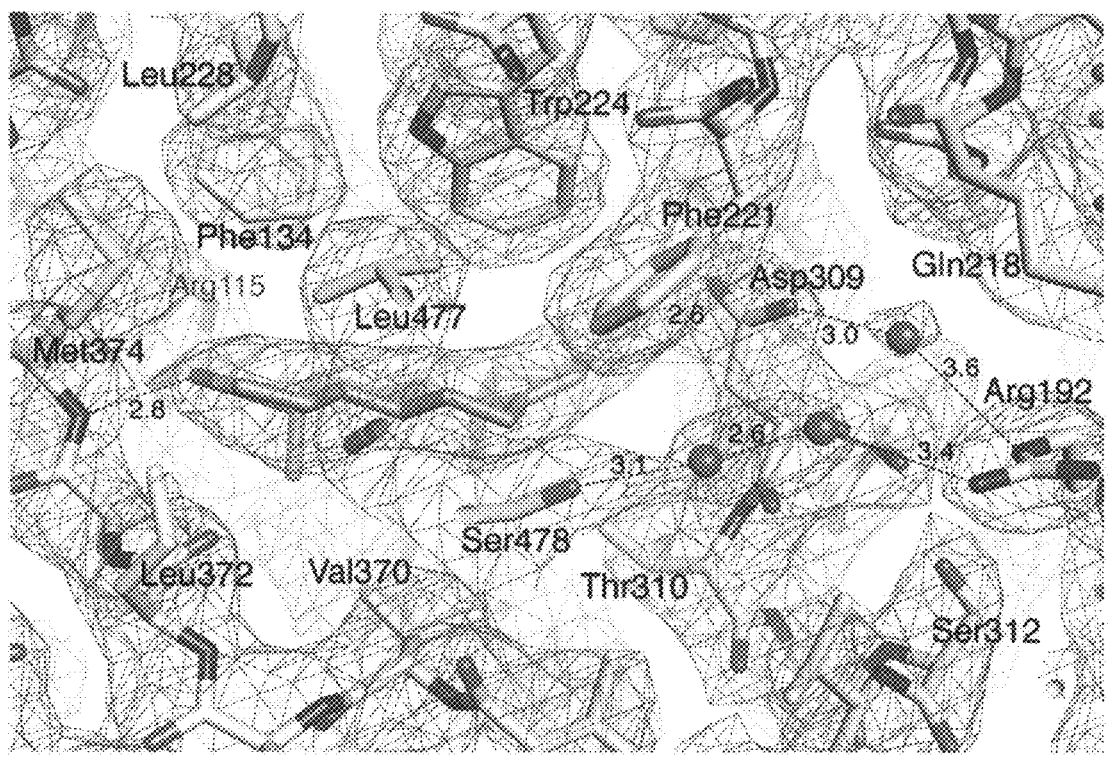
FIG. 6 shows an electron density map of the active site environment of bound androstenedione, contoured at 1.2 times the standard deviation. The hydrogen-bonding network among residues and water molecules is indicated by dashed lines and the distances are shown in Å.

The structure was solved by molecular replacement method (at 3.3 Å), coupled with Bijvoet difference Fourier synthesis utilizing the Fe-absorption edge datasets (at 4.5 Å). The latter helped in identifying the correct molecular replacement solution, at the same time confirmed that there was one molecule in the asymmetric unit. Extensive rotation and translation function searches were conducted with a large number of P450 coordinates from the Protein Data Bank (PDB ID codes: 1PQ2, 1R90, 1TQN, 1Z10, 1W0E, 1Z11, 1Z04, 1ZOA, 2F9Q, 2FDV, 2FDY, 2FDU, 2FDW, 2H14, 2J0C, 2J0D, 2OJD, and 2P85) using AMORE and MOLREP routines in the CCP4 software package [A39]. Only two search models that yielded the correct molecular replacement solution were 2F9Q (human P450 2D6) and 1W0E (human P450 3A4), the two human cytochrome P450's with highest sequence identities with aromatase (both about 14-18%). Model building and refinement were performed with Coot [A40] and Refmac5 [A41] routines, respectively, running on either a dual CPU G5 or a Powerbook G4 with the Mac OS 10.5 operating system. The final model contained 452 amino acid residues, a heme group, one androstenedione molecule, 35 solvent waters, and 2 phosphate ions (3767 total atoms). Models for 44 amino- and 7 carboxyl-terminal residues could not be built because of weakness of the their electron densities. Apart from these residues, the electron density for the rest of the molecule was mostly well defined, except for two short loop/turn regions. The fit between the experimental electron density of side chains and the corresponding sequence was excellent except for a few exposed charged amino acids, such as Lysines. In the space of missing amino-terminal residues, an isolated patch of weak electron density was identifiable and could be fitted to a distorted four-turn helix. However, owing to the lack of side chain identities, the helix could not be correctly positioned in the missing polypeptide segment and hence left out of the model. Additionally, electron densities appropriate for 2 detergent molecules were located near the Trp67 side chain, the presumed transmembrane region of the enzyme, but were not included in the final refinement owing to the possibility of multiple orientations of the sugar moiety or the alkyl chain. The final R factor for all reflections between 50 Å and 2.90 Å resolutions was 0.214 and the R-free value was 0.244. The root-mean squared deviations of bond-lengths and angles from ideal values were 0.009 Å and 1.32°, respectively. The average isotropic thermal factor (B) for all atoms was 77.3 Å$^2$, whereas the Wilson plot B-value was 94.5 Å$^2$. There were only 2 violations in the backbone torsion angle Ramachandran plot, all in weaker loop regions. Table 1 provides a summary of numbers from refinement. FIG. 5 shows the electron density of the bound androstenedione molecule. FIG. 6 is an electron density map of the active site region.

Example 4

The Crystal Structure of Aromatase

A. The Overall Structure of Aromatase

The crystal structure of highly active human placental Aromatase in complex with the substrate androstenedione has been determined at 2.90 Å resolution. The tertiary structure of Aromatase (FIG. 7a) consists of 12 major α-helices (labeled A through L) and 10 β-strands (numbered 1 through 10) distributed into 1 major and 3 minor sheets, and follows the characteristic cytochrome P450 fold. The major β-sheet is a mixed 4-stranded sheet that begins near the amino terminus (first two strands are β1:83-88 and β2:93-97) but ends in two strands from the carboxyl terminal half of the polypeptide chain (β3:373-376 and β6:393-396). A feature somewhat special to the Aromatase structure is that the amino-terminal residues 47-50, which makes one backbone hydrogen bond with β1, adds an extra β-strand-like element to this sheet. Each of the three minor sheets consists of two anti-parallel strands scattered over the polypeptide chain (sheet2: β4:381-383 and β5:386-388; sheet3: β8:473-475 and β9:479-481; sheet4: β7:458-461 and β10:491-494). Of the 12 major helices, the lengths, locations and orientations of helices I (293-324), F (210-227), G (242-267), H (278-287), C (138-152), D (155-174), E (187-205), J (326-341), K (354-366) and L (440-455) are similar to those found in most of the cytochrome P450s. Other helices, namely A' (57-68), A (69-80), B (100-109), B' (119-126), G' (232-236), H' (271-274), J' (346-349), K' (398-404), and K" (414-418) are 1 to 4 turns long and have more variability among P450s in terms of their locations, lengths and orientations. For instance, when compared with two human P450s 3A4 and 2D6 that Aromatase has the closest resemblance to (16-20% sequence identity), the helix A' in Aromatase is longer than a similar one in 3A4 and is not seen in 2D6. The other notable difference in the secondary structures between Aromatase and 3A4 is that the helix F in 3A4 is separated into two shorter helices by a stretch of polypeptide. As discussed below, this region of the structure contributes significantly to the constitution of the active site. Another difference is that the G-helix in Aromatase is at least one turn longer than those in 3A4 and 2D6. The F-helix-loop-G-helix region, in general, appears to be different in different P450s. With the helix G' in the middle, the loop is tighter in Aromatase than in either 3A4 or 2D6, both of which have longer intervening loops.

A striking feature of the tertiary Aromatase structure is that long loops interconnect well-defined secondary structure elements, again, in general agreement with other P450 structures. One example is the polypeptide between the 2-turn helix K' and helix L. This stretch of 35 residue polypeptide (405-439), devoid of much secondary structure except the 1-turn helix K", contributes the all important cysteine ligand (Cys437) to the heme iron. Other examples of long loops are between helices B' and C, β7 and β8, and β9 and β10, all of which either contribute active site residues (FIG. 7b) or have roles in scaffolding of functionally important elements. Although these loops have little intra-loop interactions through hydrogen bonding, they stabilize by interacting with other structural elements and are, thus, well defined in the electron density map. Last but not the least, a common feature that ties all cytochrome P450s together is the ligation of the heme group via its propionate moieties by arginine and tryptophan side chains through ionic and hydrogen bonding interactions. These side residues in Aromatase are Arg15, Trp141, Arg145, Arg375, and Arg435, homologous to those in 3A4, 2D6 and others.

Despite maintaining the overall P450 fold, the low sequence homology between Aromatase and other microsomal P450s is manifested in notable differences in the lengths and orientations of the α-helices, β-strands and loop regions and a drastically different active site structure. This explains why both 3A4 and 2D6 are drug/xenobiotic-metabolizing enzymes with widely diverse substrate selectivities, while in contrast Aromatase performs a very specific and unique catalytic role in steroid biosynthesis using a very specific substrate.

B. Androstenedione Complexed with the Active Site Cavity of Human Aromatase

Figure 7:
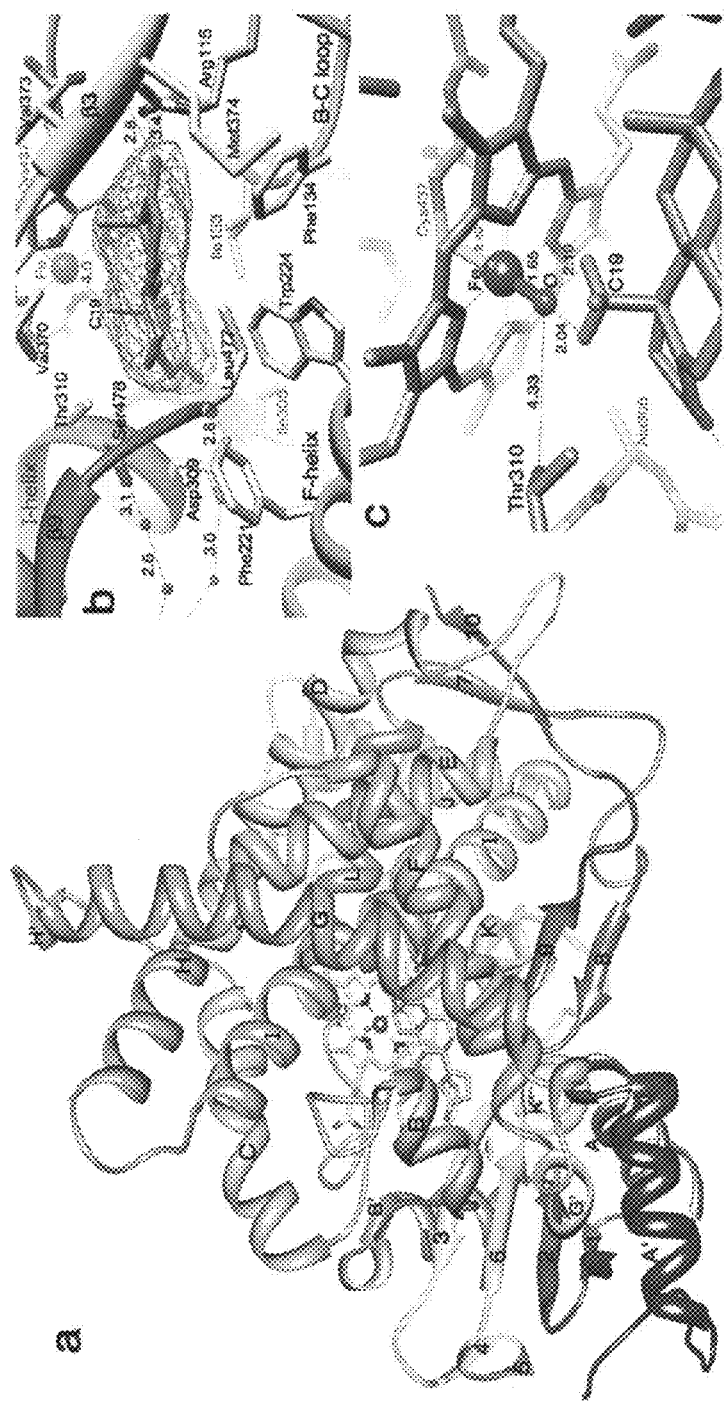
FIGS. 7A-7C depict the aromatase structure of the present invention. (A) A ribbon diagram showing the overall structure. The amino terminus, starting at residue 45, is colored dark blue and the carboxyl terminus ending at residue 496 is colored red. The α-helices are labeled from A to L and β-strands are numbered from 1 to 10. The heme group, bound androstenedione molecule at the active site, and its polar interactions are shown. (B) A close up view of the active site showing the bound androstenedione molecule in unbiased difference (Fobs-Fcal) electron density contoured at 4.5 times the standard deviation. (C) Modeling of Fe(III) as an oxyferryl Fe(IV)=O moiety. The C19-methyl hydrogen atoms are shown at the calculated ideal positions. Important side chains, heme and water molecules are depicted in element colors; C: gray, N: blue, O: red, S: yellow, Fe: firebrick, and H: orange. The C atoms of androstenedione are colored in cornflower blue. The color code is maintained for all figures throughout the manuscript. The distances are in Å. The directions of view into the active site are roughly similar in (A), (B) and (C). Unless otherwise noted, all 3D illustrations are prepared with Chimera [A46].

Unlike known P450s, it has been determined that androstenedione snugly fits in the active site cavity of human Aromatase. Androstenedione binds with its 1-face oriented towards the heme group and C19 4.0 Å from the Fe-atom (FIG. 7b). To test the catalytic viability of the substrate-binding mode, the heme Fe is modeled as a hypothetical oxyferryl Fe(IV)=O moiety (FIG. 7c). The resulting binding geometry of the C19 methyl hydrogens closely resembles that of the reactants for hydroxylation by P450cam [A42]. The residues comprising the catalytic cleft are Ile305, Ala306, Asp309 and Thr310 from the I-helix, Phe221 and Trp224 from the F-helix, Ile133 and Phe134 from the B-C loop, Val370, Leu372 and Val373 from the K-helix-β3 loop, Met374 from β3, and Leu477 and Ser478 from the β8-β9 loop (FIG. 7b). The 17-keto oxygen of the substrate makes a hydrogen bond (2.8 Å) with the backbone amide of Met374 and a weak contact (3.4 Å) with NH1 of Arg115 (FIG. 7b). The 3-keto oxygen is 2.6 Å from the carboxylate $O_{\delta2}$ of the Asp309 side chain (FIGS. 5, 6, 7b, 8a), suggesting that the carboxylate moiety is protonated. The hydrophobic residues and porphyrin rings of heme pack tightly against the steroid backbone, forming a cavity complementary in shape to the bound steroid (FIG. 8a, prepared with Molecular Operating Environment (MOE), Chemical Computing Group, Montreal, Canada). The side chains of residues Arg115, Ile133, Phe134, Phe221, Trp224, Ala306, Thr310, Val370, Val373, Met374 and Leu477 make direct van der Waals contacts with the bound androstenedione. Ile133, Phe134, Phe221, Trp224 and Leu477 approach the substrate from the α-face and follow the contour and puckering of the steroid backbone, while the side chains of Arg115, Ala306, and Met374 make contacts at its edge, and Thr310, Val370, and Val373 on the β-face. The combined surface creates a pocket that snugly encloses the bound androstenedione. The volume of the binding pocket is no more than 400 Å$^3$, considerably smaller than the volume of about 530 Å$^3$ of the active sites in 3A4 [A13] and 2D6 [A14], the two drug/xenobiotic-metabolizing human P450s with highest sequence identities (16-20%) to human aromatase.

Figure 8:
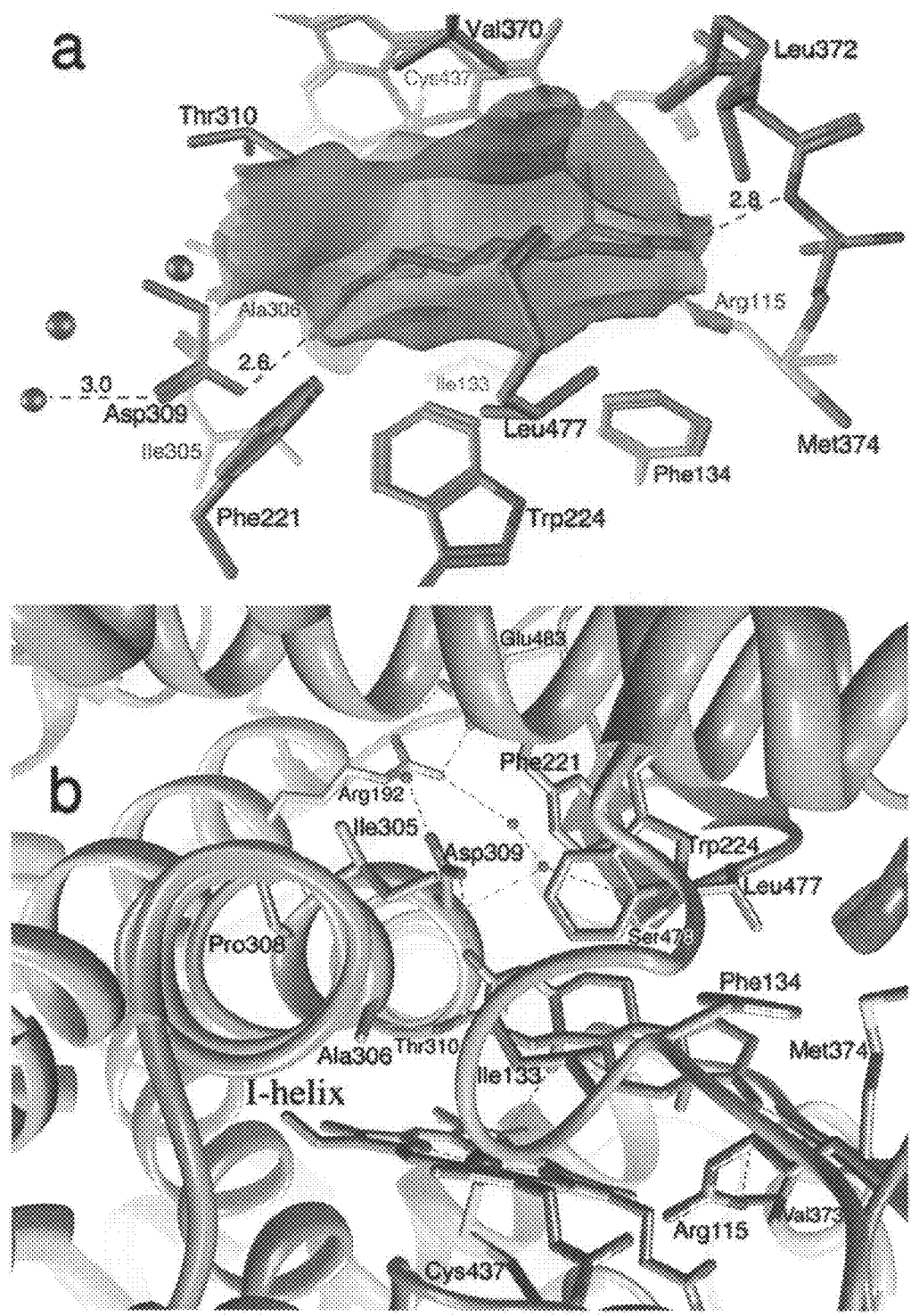
FIGS. 8A-8B are views of the aromatase active site: (A) A van der Waals interaction surface cast by the protein and heme atoms at the active site is shown. The semi-transparent surface, colored green for hydrophobic and magenta for polar interactions, closely resembles the shape, size and puckering of the steroid backbone. This figure was prepared with MOE. (B) A view along the I-helix axis from its amino-terminal end. The disruption to the helicity of the backbone at residues Pro308-Asp308-Thr310 causes the helix axis to displace about 3.5 Å, allowing the Asp309 side chain to interact with the 3-keto oxygen of the steroid. The deviation from helicity could be stabilized by a strong Ala306CO---HOThr310 (2.8 Å) hydrogen bond, as well as by Asp309 peptide CO---Water (3.4 Å) interaction as indicated.
Figure 9:
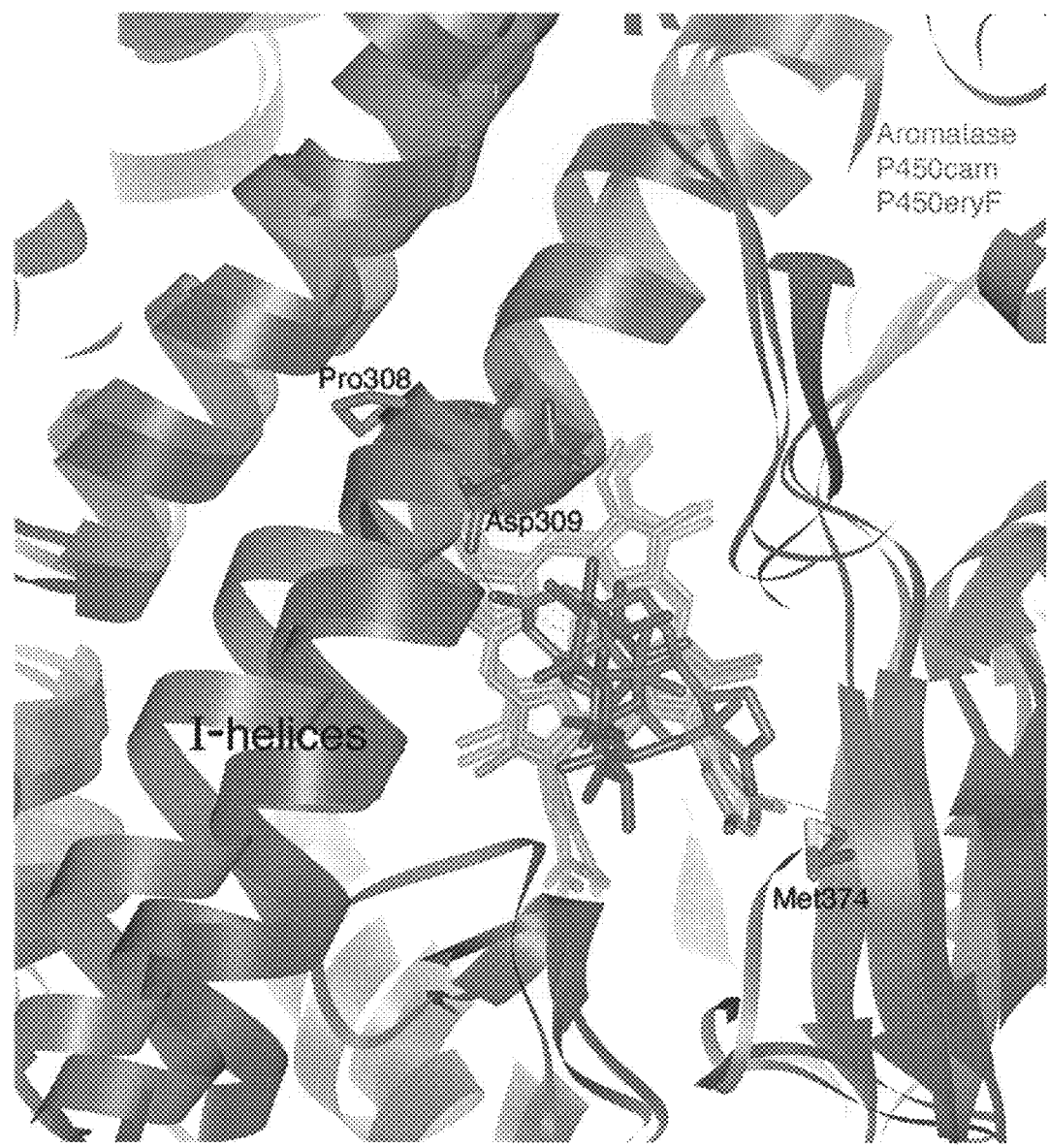
FIG. 9 shows superposition of the structures of aromatase (blue), bacterial P450cam (magenta; PDB ID: 2CPP) and bacterial P450eryF (green; PDB ID: 1OXA) shown with ligands bound at the active sites. Note that the amino-terminal end (the lower end in the figure) of the aromatase I-helix follows a course away from the active site and from the P450cam and P450eryF I-helices until the residue Pro308, which creates a kink in the protein backbone changing its course to follow the other two helices. This displacement of the amino-terminal half of the I-helix creates the extra room necessary to accommodate the A-ring of the steroid and the course alteration by Pro308 is responsible for positioning the Asp309 side chain to interact strongly with the 3-keto oxygen of the steroid. The corresponding side chains Asp251 and Glu244 in P450cam and P450eryF, respectively, do not have any interaction with their respective ligands. The residues corresponding to Pro308 in aromatase are Leu250 and Phe243 in P450cam and P450eryF, respectively. Met374 is also shown.
Figure 10:
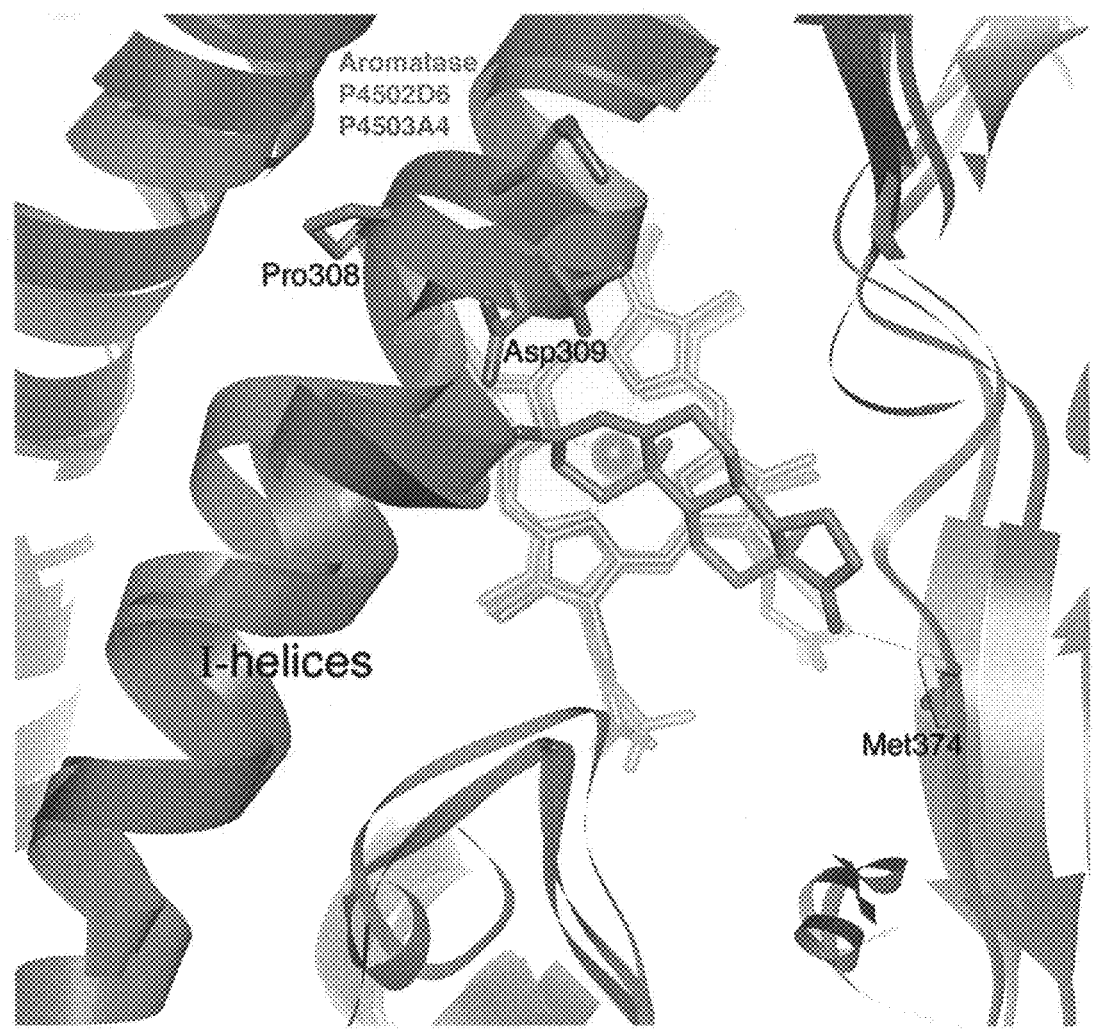
FIG. 10 shows superposition of the structures of aromatase (blue), P450 2D6 (magenta; PDB ID: 2F9Q) and P450 3A4 (green; PDB ID: 1W0E). The amino-terminal end (the lower end in the figure) of the aromatase I-helix follows a course away from the active site and from the P450 2D6 and P450 3A4 I-helices until the residue Pro308, which creates a distortion in the protein backbone changing its course to follow the other two helices. This displacement of the amino-terminal half of the I-helix creates the extra room necessary to accommodate the A-ring of the steroid and the course alteration by Pro308 is responsible for positioning the Asp309 side chain to interact strongly with the 3-keto oxygen of the steroid. The side chains corresponding to Asp309 in aromatase are Val308 and Glu308 in P450 2D6 and P450 3A4, respectively. The residues corresponding to Pro308 in aromatase are Met307 and Tyr307 in P450 2D6 and P450 3A4, respectively. Met374 is also shown.

A distortion in the I-helix backbone resulting in a ~3.5 Å displacement of the helix axis is crucial for creating the androgen-specific binding pocket at the active site. This shift in the helix axis caused by Pro308, a residue unique to aromatase among all P450s, is stabilized by a strong Ala306CO---HOThr310 (2.8 Å) hydrogen bond, as well as by an Asp309 peptide CO---Water (3.4 Å) interaction (FIG. 7b). Although an irregularity in the I-helix backbone at this region is observed in other P450s [A13,14,43,44], this Pro308-mediated axis shift precisely accommodates the 3-keto end of androstenedione near the 5$^{th}$ turn of the helix (Met303 to Ala307), allowing the Asp309 side chain to hydrogen bond to the 3-keto oxygen (FIG. 8b). Superposition of the aromatase backbone with bacterial P450cam and P450eryF (FIG. 9) as well as with human P450 3A4 and P450 2D6 (FIG. 10) shows that without this shift, the 3-keto end of the substrate would clash with the 1-helices of P450cam, P450eryF, P450 2D6 and P450 3A4. The structure thus confirms the critical roles of Pro308 and Asp309 predicted by mutagenesis and modeling [A19,25,27].

The Asp309 side chain also forms a hydrogen bond with a water molecule 3.0 Å from $O_{\delta 1}$ (FIGS. 5, 6, 7b, 8a). The geometries of these two hydrogen bonds place the 3-keto oxygen and the water oxygen atom roughly in the carboxylate plane (FIG. 8b). Furthermore, this water molecule is situated at 3.6 Å from the guanidinium group of the Arg192 side chain (FIG. 6), which forms a salt bridge with Glu483. An elongated electron density adjacent to the Ser478 side chain (FIG. 6) was modeled as two water molecules, hydrogen-bonded to each other and to the Ser478 side chain OH, which in turn donates a hydrogen bond to His480 $N_{\delta 1}$ further away from the active site. The Ser478 side chain is linked via these two water molecules to Arg192 by a weak hydrogen bond (3.4 Å; FIGS. 6, 8b). It is probably as a result of being linked to this network of proton donors on one side, and the keto group of a large hydrophobic substrate on the other, that the Asp309 side chain remains protonated and engaged in the substrate-binding interaction. Furthermore, this network could also serve as the proton source for the proposed participation of the Asp309 carboxylate moiety in the enolization process, as discussed below.

C. Substrate-Binding Geometry

Figure 11:
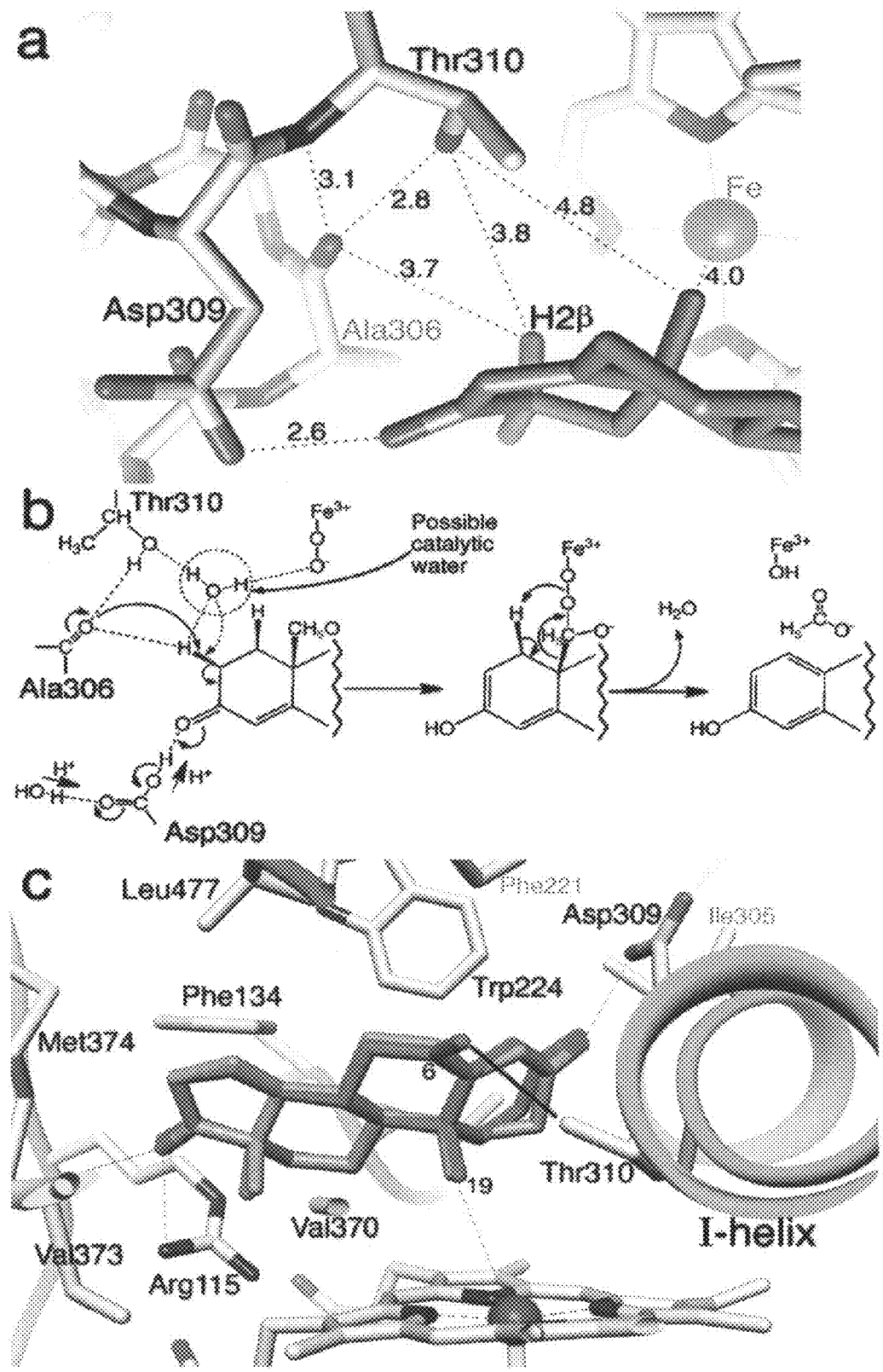
FIGS. 11A-11C illustrate various aspects of aromatization. (A) A close up view of the 306AlaCO---HOThr310 pair that may have a role in aromatization of the A-ring. Calculated H-atom positions of C2 of androstenedione are shown. Distances are in Å. (B) A possible mechanism for H2β abstraction and 2,3-enolization could be initiated by a nucleophilic attack on C2-H2β by the A306AlaCO---HOThr310 pair, along with an electrophilic attack on the C3 carbonyl by a protonated Asp309 side chain. The direction of proton flow from the proton relay network via Asp309 to the substrate is indicated. The A306AlaCO---HOThr310 pair aided by a possible catalytic water molecule, or the water oxygen itself (dotted arrow) could act as the nucleophile. H1β abstraction is drawn as previously proposed. (C) Modeling of exemestane (in magenta). The short van der Waals contact distance (3 Å) between the C6-methylidene carbon and Cγ of Thr310 is indicated by a black line.

Substrate-binding geometry provides mechanistic insight for the unique aromatization reaction. H2β of the A-ring of the bound androstenedione (FIG. 11a) that gets abstracted in the aromatization step is close to the Ala306CO---HOγThr310 pair (C=O-----H2β-C2: 3.7 Å and C2-H2β----OγH: 3.8 Å). Thr310, highly conserved in P450s, has been implicated in the P450 hydroxylation steps. The mechanism of P450 hydroxylation has been extensively studied for two bacterial enzymes P450cam [A43] and P450eryF [A44]. In the dioxygen complex of P450cam, the residue pair Thr252-Gly248 carbonyl, and two catalytic water molecules are involved in the activation of ferrous-dioxygen to the hydroxylating Fe(IV)=O species by providing two protons [A43]. A similar hydroxylation mechanism involving the corresponding Thr310-Ala306 carbonyl pair, and catalytic water molecules (the binding of which could be promoted by dioxygen binding as in P450cam) is probably at work for each of the first two steps catalyzed by aromatase, yielding the C19-aldehyde derivative of androstenedione through 19,19-gem-diol formation and retention of the pro-S hydrogen [A20,21]. The same catalytic residues could also be responsible for the H2β abstraction of the 2,3-enolization processes in the aromatization step. To accomplish this, a nucleophilic attack on H2β-C by the Ala306CO----HOγThr310 moiety (perhaps along with a water) and a concerted electrophilic attack on the C3-keto oxygen by a protonated Asp309 side chain could promote the H2β abstraction and 2,3-enolization, akin to —H$_2$C2-C3-keto to —HC2=C3-enol tautomerization (FIG. 11b). A bound water molecule (perhaps linked to the proton relay network) between Thr310-Oγ and the iron-peroxy/hydroperoxy intermediate could lower the pKa of Thr310-OγH, rendering Ala306C=O a more potent nucleophile, or alternatively, could itself act as a nucleophile, as shown in FIG. 11b. Asp309 thus appears to have a direct participation in enolization, unlike the indirect roles of Asp251 and Glu244 in hydroxylation by P450cam and P450eryF, respectively [A43, 44]. A density function theory calculation for the final catalytic step of aromatase suggests a strikingly low energy barrier (<7 kcal mole) for H1β abstraction when steroids are 2,3-enolized [A45]. The 1β hydrogen, however, is too far from this carbonyl (6.2 Å) to be abstracted in such a manner. It points at and is close to the heme Fe (4.2 Å), and is probably removed following the Fe-peroxy nucleophilic attack on 19-aldehyde (FIG. 11b) as previously proposed [A20,21].

In order to examine how a mechanism-based steroidal inhibitor could interfere with the aromatization process, an exemestane (AROMASIN®; one of the three FDA-approved aromatase inhibitors) molecule was built into the active site (FIG. 11c) using the androstenedione backbone. The two steroids superimpose quite well (rmsd ~0.2 Å), except for differences in puckering of the A-rings. The extra C6-methylidene group in exemestane is accommodated in a shallow hydrophobic crevice surrounded by the side chain C-atoms Thr310-Cγ, Val370-Cγ2 and Ser478-Cβ, at the mouth of the active site access channel (described below). The distance between the methylidene C and Cγ-Thr310 is 3 Å, shorter than the van der Waals contact distance. Indeed, slight adjustment of these side chains upon exemestane binding is highly likely. The clamping of C6-methylidene in a hydrophobic surrounding, resulting in entropic gain, and lowering of the free energy and the dissociation constant, could greatly reduce the mobility of the Thr310 side chain and/or interfere with its ability to interact with the catalytic waters for the creation of the active oxyferryl moiety. Exemestane would thus remain tightly bound in the pocket without being hydroxylated at C19.

D. Unique Transmembrane Domain of Human Aromatase

The unique transmembrane domain of human Aromatase positions the steroid entry/exit channel at the lipid interface.

Figure 12:
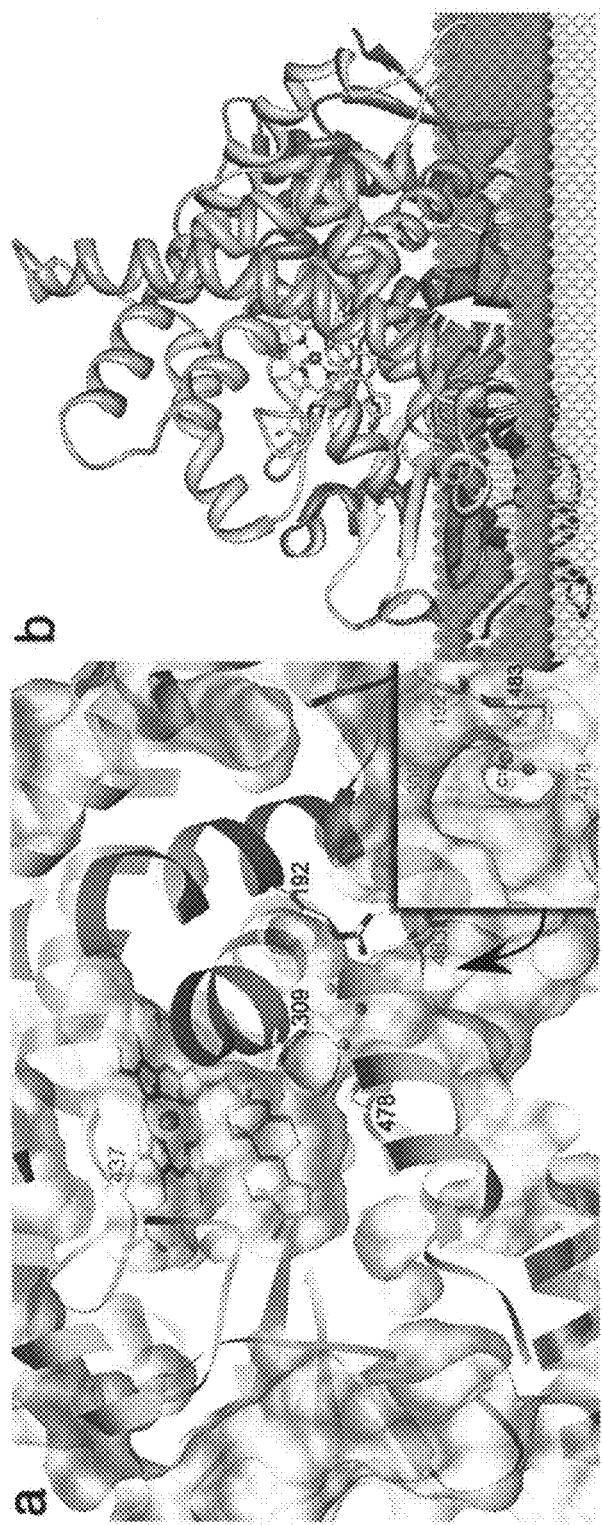
FIGS. 12A-12B illustrate a putative aromatase active site access channel from within the lipid bilayer. (A) The solvent-excluded surface [46] of aromatase excludes the steroid-binding pocket and heme from the protein interior by forming a "pouch"-like cleft that has the only opening to the protein exterior through a channel, roughly at the arrowhead. The course of the polypeptide chain is shown in rainbow color. Residues Arg192, Asp309, Ser478, and Glu483 border this channel from the protein interior, while three water molecules, part of the proton relay network, are within the channel. The inset is a view along this channel at the arrowhead, showing the locations of water molecules and opening to the active site. (B) In a proposed membrane integration model, the opening to the active site access channel rests on the lipid bilayer surface, allowing the steroids to enter the aromatase active site directly from within the bilayer, roughly along the arrow shown. The model suggests lipid integration/association of the amino terminus up to the helix A, and other loops near the carboxyl terminus. The orientation of aromatase is roughly the same in (A) and (B).

An access channel links the active site to the outer surface. FIG. 12a is a view of the interior of a semi-transparent solvent-excluded surface [A46] that also excludes the active site region, consisting of the steroid-binding pocket and heme, from the protein interior by forming a "pouch"-like cleft that opens only to the exterior through the channel, at the arrowhead. The inset shows a view along this channel, revealing the locations of three water molecules within the channel and a glimpse of the opening to the active site cavity. The salt bridging Arg192-Glu483 pair as well as Asp309 and Ser478 line the channel that hosts the putative proton relay network and is also probably the major transport route to and from the active site for water, oxygen and steroid molecules. This channel appears to be a confluence of what was previously described as channels 2a, 2ac and 2c for other P450s [A47]. Although it narrows at points, the channel is probably flexible to permit the passage of molecules such as steroids.

Having 7 cysteines in the reduced form, the bulk of aromatase probably resides in the reducing environment of the cytoplasm. A hydrophobicity plot of the aromatase sequence suggests lipid integration for residues 21-42 and 49-71, thereby placing the amino terminus having glycosylation at Asn12 on the opposite side, i.e. the lumen [A48]. It is possible that the transmembrane segment of residues 21-42, too short to traverse the bilayer as a regular α-helix, is at least partly an extended polypeptide devoid of secondary structure. This is consistent with the observed weak electron density for the polypeptide chain beyond residue 45 towards the amino terminus. It is also likely that the hydrophobic helix A' (residues 57-68) and part of helix A (residues 69-80) are embedded in the membrane. This arrangement positions several arginine (Arg64, Arg79 and Arg86) and tryptophan (Trp67 and Trp88; Trp239 from the F-G loop) residues at the lipid-protein interface, a telltale sign of lipid integration [A49]. Besides, electron densities for at least 2 detergent molecules were identified near Trp67 of helix A'. We, thus, propose that lipid integration of aromatase begins with these helices, as the amino terminus traverses farther into the bilayer towards the lumen side. A model (FIG. 12b) based on these concepts places the entrance to the active site access channel (FIG. 12a) on the membrane surface. Although other possible entry/exit routes cannot be excluded, this arrangement allows the lipophilic substrate to enter the aromatase active site directly from within the membrane, traveling between and across the F-G loop and the β8-β9 loop, roughly along the path indicated by an arrow (FIG. 12b). The structure of aromatase, thus, provides a rationale for its crucial membrane integration and reveals a finely tuned molecular machine that makes estrogens from androgens. Utilization of the molecular basis for enzyme-substrate and enzyme-drug interactions could lead to more efficacious intervention of estrogen production.

Example 5

Structural Basis for Androgen Specificity and Estrogen Synthesis in Human Aromatase The present example describes various methods used for isolating, purifying, and crystallizing a human aromatase of the present invention.

Aromatase was purified from term human placenta by immuno-affinity chromatography in highly active form. It was complexed with androstenedione and crystallized at 4° C. in the oxidized high-spin ferric state of the heme iron using polyethylene glycol 4000 as the precipitant. The space group was $P3_221$ and the unit cell parameters are a=b=140.2 Å, c=119.3 Å, α=β=90°, γ=120°, having one aromatase molecule in the asymmetric unit. Diffraction data at ~100K was collected initially at the Cornell High Energy Synchrotron Source (CHESS) and then to 2.90 Å resolution at the Advanced Photon Source, Argonne National Laboratory, Argonne, Ill., using glycerol as a cryoprotectant. Two data sets at the Fe absorption edge were also collected at the CHESS. The structure was solved by the molecular replacement method coupled with Bijvoet difference Fourier synthesis for identifying the correct solution. Model building and refinement were performed with Coot and Refmac5, respectively. The final model contained 452 amino acid residues—44 amino- and 7 carboxyl-terminal residues could not be built because of weakness of their electron densities. The final R factor for all reflections between 38 Å and 2.90 Å resolution was 0.214 and the R-free value was 0.244. The root-mean squared deviations of bond-lengths and angles from ideal values were 0.009 Å and 1.32°, respectively. The average isotropic thermal factor for all atoms was 77.3 Å$^2$. There were only 2 violations in the backbone torsion angle Ramachandran plot, both in the loop regions. The oxyferryl Fe(IV)=O moiety was generated by adding an oxygen atom to Fe using the modeling software MOE (Molecular Operating Environment, Chemical Computing Group, Montreal, Canada) The exemestane molecule was built into the active site by superimposing it on the experimentally derived androstenedione atomic positions using MOE.

Purification and crystallization: The enzyme was purified to homogeneity from the microsomal fraction of homogenized fresh human placenta by immunoaffinity chromatography. The purified enzyme was highly active—the specific activity with androstenedione as the substrate ranged between ~10 and ~100 nmol/min/mg over a large number of purification experiments. Details of this procedure have been previously described. The absorption spectrum of the androstenedione complex exhibited a Soret band at 394 nm, which is characteristic of the oxidized high-spin ferric ($Fe^{3+}$) state of the heme iron, suggestive of the formation of the androstenedione complex. Freshly purified aromatase in 100 mM potassium phosphate buffer, pH 7.4, containing 20% glycerol, 0.1 mM androstenedione, and 1 mM n-dodecyl-β-D-maltopyranoside (BDM) was mixed with reservoir cocktails of 24 to 30% polyethylene glycol 4000 and 0.5M NaCl in 0.05M Tris-HCl buffer pH 8.5 and vapor diffused in sealed 24-well sitting drop plates against corresponding reservoir solution. The purification and crystallization experiments were all conducted at 4° C. Reddish-brown color hexagonal rod-shaped crystals appeared in 7-10 days and continued to grow up to 14-16 days. Typically, the crystals are about 0.05 mm to 0.50 mm in lengths, and have a hexagonal cross-section of about 0.01 mm to 0.12 mm.

Example 6

Experimental Studies on the Crystal Structure of Human Aromatase

This example describes various experimental studies regarding the purification of the human Aromatase of the present invention. Some of this information documents preliminary studies leading up to the purification and crystallization of the human Aromatase. Other portions of this example reiterate experimental studies set forth herein.

We have purified P450arom from human term placenta to homogeneity in a stable, active form, and streamlined the procedure for routine isolation. The reported crystals of the P450arom-androstenedione (A) complex have improved in quality. We have now gathered high-quality diffraction data on this complex crystal, complete to 2.90 Å resolution and recorded diffraction to even higher resolution (~2.7 Å). We now have a solution for the crystal structure of the P450arom-A complex at 2.90 Å resolution and have built an atomic model. The refinement of the model is nearing completion. Additionally, we have prepared under the crystallization conditions inhibited complexes of P450arom with exemestane, letrozole and anastrozole, three known inhibitors of P450arom, and obtained the first crystals of P450arom-exemestane complex. We have also prepared a complex of P450arom with a highly specific monoclonal antibody, and continue to raise rabbit polyclonal antibodies to the enzyme. Furthermore, we have acquired a bacterial clone of P450arom (Del38arom), proceeded to sub-clone the DNA into a baculovirus expression system and expressed Del38arom in Sf9 insect cells. Studies have proceeded regarding the synthesis of several androstenedione analog compounds as potential inhibitors of P450arom. Lastly, we have now cloned, expressed and purified the full-length human CPR for preparing the P450arom complex. Details of the results are given below:

A. Purification of P450arom from Human Placenta

Fresh human term placentas were collected from local hospitals. One complete placenta was used for each purification. The entire purification process was carried out at 4° C. The tissue was cleaned, cut and rinsed with 67 mM Na/K phosphate buffer containing 1% KCl. To each gm of the tissue was added 0.5 ml of 67 mM Na/K-phosphate buffer containing 240 mM sucrose and 0.5 mM dithiothreitol (DTT). The mixture was homogenized for few minutes. The placental homogenate, if not used immediately, was stored at −80° C. until needed.

The homogenate was thawed and centrifuged at 35,000 rpm using 45Ti rotor for 50 minutes and the supernatant was discarded. The pellet was homogenized with 600-700 ml (for a 600-700 g placenta) of buffer A (10 mM K-phosphate buffer, pH 7.4, containing 0.1 mM ethylenediamine-tetraacetic acid (EDTA), 0.5 M androstenedione and 20% glycerol). The homogenized pellet was then applied to a monoclonal antibody (mAb 3-2C2) column washed and equilibrated with about 50 ml of buffer A containing 0.15% Emulgen913 (Em). The immunoaffinity column was washed with buffer A (+Em) until the red coloration was no longer visible on the column. The column was then washed with about 50 ml of 0.5M NaCl in buffer A (+Em). The bound P450arom was eluted with 100 ml of 4M NaCl in buffer A (+Em). The eluted P450arom fractions were collected in tubes each containing 3 ml of buffer A (+Em), plus 0.5 mM DTT. The pooled fractions were loaded onto a pre-equilibrated G-25 (2.5 cm×95 cm) column and eluted with buffer A (+Em), plus 0.5 mM DTT. The peak fractions were collected and applied to a hydroxyapatite (HA) column equilibrated with buffer A (+Em) containing 0.5 mM DTT. The column was first washed with 50 ml of buffer A (+Em) plus 0.5 mM DTT and then with about 70 ml of buffer A (−Em) plus 0.5 mM DTT, containing 2 mM β-D-nonyl maltopyranoside (BNM) or 1 mM β-D-dodecyl maltopyranoside (BDM). Thus, the detergent Em was exchanged with BNM (or BDM), more suitable for crystallization purposes. The purified P450arom was eluted from the HA column with 200 mM K-phosphate in buffer A (−Em) plus 0.5 mM DTT, containing 2 mM BNM. The protein was then concentrated to 20-30 mg/ml using Centricon YM30 ultra-concentrators. One placenta typically yielded 5 to 10 mg of P450arom purified essentially to homogeneity (FIG. 5). It is the high specificity of mAb 3-2C2 for the human enzyme and our immunoaffinity-based purification scheme that are responsible for the observed yield, homogeneity and high specific activity of the purified enzyme. The entire purification process takes less than a week to complete.

B. Measurement of Activity

Purified P450arom (0.20 μg) was reconstituted with 2 μg P450-reductase (CPR) and 20 μg 1,2-diarachidoyl-sn-glycero-3-phosphocholine. Reconstituted P450arom was preincubated with 0.24 μM of the substrate, [1β-$^3$H, 4-$^{14}$C] androstenedione, with specific activity $2.7\times10^3$ dpm of $^3$H in 1 ml of 100 mM K-phosphate buffer at pH 7.4 containing 20% glycerol and 0.15% emulgen. Following preincubation at 37° C. for 10 minutes, the aromatase reaction was started by addition of 0.1 ml of 0.5 mM NADPH in 100 mM KPO4 buffer at pH 7.4 containing 20% glycerol. After shaking for 20 minutes at 37° C., the reaction was terminated by the addition of 0.4 ml of 20% trichloroacetic acid and 1.0 ml of 5% charcoal. After continued shaking at 37° C. for another 30 minutes, the mixture was centrifuged, and the supernatant is filtered through a cotton-plugged disposable Pasteur pipette. The $^3$H water in the eluate was assessed according to the 1β elimination mechanism (75% release into water) [50]. The specific activity of the purified P450arom was in the range 50-100 nmol/min/mg with Em as the detergent, one of the highest reported in the literature. The turnover number was calculated to be ~6/min. In the small molecule detergents BNM and BDM, the specific activity of P450arom is retained at 80-90% levels at 4° C. for weeks.

C. Confirmation of Protein Identity by Amino-Terminal Sequencing

A SDS-PAGE analyzed band of highly pure P450arom was blotted on to a Polyvinylidene fluoride membrane. The band was then cut off from the membrane, dried and sent for protein sequencing by the Edman degradation method to ProSeq, Inc (Boxford, Mass.). Other than two minor ambiguities at positions 2 and 10, it was a clean, single protein band with 100% match with the known P450arom sequence, thereby confirming that purified and crystallized protein is indeed P450arom.

D. Search for an Optimal Detergent

Emulgen913 (Em), long established as the detergent of choice for extraction and purification of P450arom, is not suitable for crystallization because of its large size and heterogeneity. Furthermore, one of the most commonly used detergents for crystallization, n-octyl-β-D-glucopyranoside (BOG), was found to destroy P450arom activity rapidly [51]. Subsequently, we determined that n-dodecyl-β-D-maltopyranoside (BDM), another detergent suitable for crystallization of proteins, maintained P450arom activity for weeks at 4° C. [51]. However, the low critical micelle concentration (CMC) of BDM sometimes resulted in the formation of detergent micelles and precipitation or crystallization of the detergent. Therefore, we decided to screen detergents with glucopyranoside and maltopyranoside head groups and varying chain lengths. Six new detergents tested had CMC values between 1.5 and 19.5 mM. Hydroxylapatite (HA) column chromatography was used to perform a thorough exchange of Em with the detergent. Both enzyme activity and time stability were assessed with these detergents, all of which were suitable for crystallization of proteins. At concentrations of 1-3 mM, two of these detergents, n-nonyl-β-D-maltopyranoside (BNM) and n-octyl-β-D-maltopyranoside (BOM), maintained enzyme activity and time stability at least as well as BDM. BNM, in particular, showed superior ability in maintaining the enzyme activity at a high level for a prolonged period of time. The retention of P450arom activity by BNM alone (no addition of Em for the activity assay) as a function of concentration was better than activity retention by BDM. This study demonstrated that, up to a concentration of about 3 mM, BNM maintained the full P450arom activity when assayed in the absence of any Em. It should be noted that even Em inactivates the enzyme at concentrations greater than 1%. Subsequently, crystallization experiments were conducted with P450arom preparations both in BNM, as well as in BDM.

E. Crystallization of Human P450arom-A Complex

Freshly purified P450arom is concentrated to about 1-2 mg/ml (~0.02 mM). The concentration of A in solution was adjusted to 0.10 mM and the solution was incubated overnight with mild stirring. The absorption spectrum obtained from the resulting complex exhibits a Soret band at 394 nm, which is characteristic of oxidized Ferric ($Fe^{3+}$) state of the heme iron, suggesting the formation of the A-complex [3,20].

The final protein concentration, judged by the modified Lowry method, SDS-PAGE and absorption at 280 nm, is adjusted by ultrafiltration to 25 mg/ml-32 mg/ml (0.45-0.60 mM) in 100 mM K-phosphate buffer, pH 7.4, containing 20% glycerol, 0.1 mM EDTA, 0.1 mM A, and 2 mM BNM (or 1 mM BDM). The protein solution was mixed with the reservoir cocktails of 24 to 30% polyethylene glycol (PEG) 4000 in 50 mM Tris-HCl buffer, pH 8.5, containing 0.5M NaCl, in the ratios of 1:1, 2:1 and 3:1, and vapor diffused in sealed 24-well sitting drop plates against corresponding reservoir solution. The entire crystallization experiment was conducted at 4° C. The reddish-brown color hexagonal rod-shaped crystal appeared in 7-10 days and continued to grow up to 14-16 days. Typically, the crystals are about 0.05 mm to 0.50 mm in lengths, and have a hexagonal cross-section of about 0.01 mm to 0.12 mm. The crystals have now been grown reproducibly from 9 different placental purifications.

F. Diffraction Experiments

X-ray diffraction experiments were conducted at the A1 station of the Cornell High Energy Synchrotron Source (CHESS). The A1 beam line receives monochromatic (double Si-crystal focused) X-rays from a 49-pole Wiggler at the fixed wavelength of 0.978 Å. The detector used for the entire diffraction experiment was ADSC Quantum-210 2X2 charge coupled detector (CCD). The crystals receive a flux of about $7.5\times10^{11}$ photon/second through a 200 μm collimator at the storage ring current of about 250 mA. The storage ring current decayed ~20% maximum over a period of 4 hours, and was replenished for the next run cycle. The crystals were cooled at cryogenic temperature by plunging them into liquid nitrogen and then maintaining them in a stream of liquid nitrogen at 100° K. Many different cryo-protectants were tried for this purpose. One that was best able to protect the integrity of the crystals was the crystal growth medium with the glycerol concentration adjusted to about 35%.

Four complete diffraction data sets were collected with highest resolutions ranging between 2.9 and 3.4 Å. Although some of the crystals displayed diffraction spots up to 2.9 Å, owing to the radiation damage the diffraction became progressively weaker between 2.9 and 3.2 Å, and the data at this range is weak and incomplete. Each frame of data represented 1° oscillation of the crystal. Each data set consisted of a minimum of 120 to a maximum of 180 data frames.

The data was processed with HKL2000 [52] software package. The crystal belongs to the space group $P3_221$ with unit cell parameters a=b=140.17 Å, c=119.43 Å, α=β=90', γ=120°. With one P450arom molecule in the asymmetric unit of the crystal, the crystal solvent content is about 79%, in the high solvent territory for a protein crystal. Table 2 summarizes diffraction data collection numbers.

TABLE 4

Summary of data collection at beamline SBC-19-ID, APS

| | |
|---|---|
| Data frames, oscillation angle, exposure time | 200, 1°, 15 sec |
| Wavelength, number of crystals used | 0.979 Å, 1 |
| Total number of observations | 184,295 |
| Space group and unit cell | $P3_221$ |
| | a = b = 140.208 Å, |
| | c = 119.266 Å, |
| | α = β = 90°, γ = 120° |
| Resolution range | 50.0 Å-2.90 Å |
| Number of unique reflections | 30,371 |
| Completion percentage (in highest shell) | 99.4 (99.7) |
| Intensity/standard dev. (in highest shell) | 31.1 (2.8) |
| R-merge (in highest shell) | 0.067 (0.479) |

TABLE 2

Summary of X-ray data collected at the Cornell High Energy Synchrotron Source

| Data set | Total Observation | Unique Data (completeness %) | Anomalous | Highest resolution I > σ | Rmerge |
|---|---|---|---|---|---|
| 1 (63__B1a2) | 124,357 | 17,376 (99.6 to 3.5 Å) | Yes | 3.30 | 0.08 |
| 2 (67__B1c6) | 181,398 | 17,645 (99.7 to 3.5 Å) | Yes | 3.30 | 0.08 |
| 3 (67__B2a4) | 91,866 | 29,753 (99.9 to 3.2 Å) | Yes | 3.20 | 0.09 |
| 4 (67__B2b2) | 145,602 | 30,146 (99.2 to 3.1 Å) | Yes | 3.10 | 0.10 |

G. New Diffraction Data

Using the CHESS synchrotron X-ray facility, we gathered two P450arom diffraction data sets at the F-2 station by tuning the X-ray energy to the absorption edge of Fe. This experiment was designed to maximize the anomalous scattering from the heme Fe atom and to conduct a multiple anomalous dispersion or MAD experiment for locating the Fe position in the P450arom crystals and also to help solve the phase problem. Although the intensity of the X-ray beam was greatly reduced at the Fe-absorption edge energy of 7.12 keV, we were able to gather low-resolution 4.2 Å data sets at the inflection (1.7433 Å) and remote (1.7284 Å) points of the Fe-absorption edge on the crystals of P450arom. The objective was to use these data sets in conjunction with any molecular replacement solution to solve the P450arom structure. Table 3 provides a summary of results from processing of these two data sets.

H. Elucidation of the Crystal Structure of P450arom-A Complex

The structure has been solved by molecular replacement method, coupled with Bijvoet difference Fourier synthesis utilizing the Fe-absorption edge datasets. The latter has helped in identifying the correct molecular replacement solution. Extensive rotation and translation function searches have been conducted with a large number of P450 coordinates from the Protein Data Bank (PDB ID codes: 1PQ2, 1R90, 1TQN, 1Z10, 1W0E, 1Z11, 1ZO4, 1ZOA, 2F9Q, 2FDV, 2FDY, 2FDU, 2FDW, 2HI4, 2J0C, 2J0D, 2OJD, and 2P85) using AMORE and MOLREP routines in the CCP4 software package [53]. Only two search models that have yielded the correct molecular replacement solution are 1W0E (human P450 3A4) and 2F9Q (human P450 2D6), the two human cytochrome P450's with highest sequence identities with

TABLE 3

Summary of Fe-absorption edge data collected at the CHESS, Cornell University, Ithaca

| Data set | Total Observation | Highest resolution (Å) | Unique Data (completeness %) | Wavelength (Å) | I/σ(I) Highest shell | Rmerge |
|---|---|---|---|---|---|---|
| 1 (63__B1a2) | 32,671 | 4.20 | 9,903 (97.8) | 1.7284 | 4.6 | 0.126 |
| 2 (67__B1c6) | 31,833 | 4.20 | 9,814 (97.0) | 1.7433 | 4.1 | 0.159 |

A much improved diffraction data set has been gathered from an improved crystal of P450arom at the beam line SBC-19-ID of the Advanced Photon Source, Argonne National Laboratory. Not only the resolution was improved from ~3.30 Å (Table 2) to 2.90 Å, the data quality was vastly improved and nearly 100% complete, judging from the data processing statistics in Table 4. Diffraction spots were visible to about 2.7 Å resolution, but the data was processed to 2.90 Å.

Aromatase (both about 16-20%). Model building and refinement are being performed with Coot [54] and Refmac5 [55] routines, respectively, running on either a dual CPU G5 or a Powerbook G4 with the Mac OS 10.5 operating system. The current R factor for all reflections between 50 Å and 2.90 Å resolutions is 0.213 and the R-free value is 0.245. The root-mean squared deviations of bond-lengths and angles from ideal values are 0.009 Å and 1.32°, respectively, with good Ramachandran plot agreement. Unbiased electron density maps for the bound A in the active site demonstrates the quality of the current model. We will soon be able to complete the model refinement process and start analysis of the structural results.

I. Preparation and Crystallization of the Inhibited Complex of P450arom with Exemestane We have initiated the effort to grow diffraction quality crystals of inhibited complexes of P450arom with letrozole, anastrozole and exemestane, three known inhibitors of P450arom. Purified P450arom solutions at concentrations of about 0.05 mM were incubated overnight with roughly 10-fold molar excess of the inhibitors. The resulting solutions displayed about 95% or better reduction in the P450arom enzyme activity for all three inhibitors. The Soret bands for both letrozole and anastrozole complex was shifted up to 421 nm, whereas for exemestane the Soret band was at 394 nm, similar to that of the A-complex, reflecting the high spin ferric state of the heme group. This data suggests that while the steroidal inhibitor exemestane probably binds at the active site like a substrate, the binding of non-steroidal letrozole and anastrozole alters the electronic state of heme.

The complex solutions were concentrated and set up for crystallization around the previously successful condition. We have recently obtained single crystals of the P450arom-exemestane complex. The crystals, about 0.1 mm long, resemble in color and morphology those of the P450arom-A complex. Optimization of the growth conditions is currently underway to improve the size of the crystals.

J. Preparation of Monoclonal Antibody Complex of P450arom

We established that P450arom could be inhibited in a dose-dependent manner by the recombinant dimeric $VL_2$ (variable domains of the light chain) and the single-chain Fv (scFv; linked variable domains of the light and the heavy chain) fragments of the monoclonal antibody mAb 3-2C2 to P450arom [51]. However, the inhibition was not as pronounced as by either of the natural IgG or F(ab')$_2$ molecules [50]. Secondly, the yields of the recombinant fragments remained low in spite of our repeated optimization efforts. Therefore, we pursued crystallization of IgG- and F(ab')$_2$-complexes of P450arom. The Fab fragment of mAb3-2C2 was previously shown to have much lower affinity than IgG or F(ab')$_2$ (IC$_{50}$ of ~80 µg/ml as opposed to ~1 µg/ml). Consequently, the strategy was to prepare the F(ab')$_2$-P450arom complex first and then to attempt also to crystallize the Fab'-P450arom complex by reducing F(ab')$_2$ to Fab' by adding DTT in the crystallization drops. This technique resulted in successful crystallization in our laboratory of a Fab'-antigenic peptide complex of a mAb to a melanoma antigen [56]. Details of the complex preparation and purification procedure have been published [51]. Briefly, the enzyme was mixed with F(ab')$_2$ in a molar ratio of 2:1 and incubated overnight. Unbound P450arom was removed by a mAb 3-2C2 column. The complex was then captured by a HA column to remove it from free F(ab')$_2$ and eluted with 200 mM phosphate buffer. The purified complex displayed 80% inhibition of the P450arom activity. We have recently used an isothermal titration calorimeter (ITC) to record directly the interaction between P450arom and mAb3-2C2 IgG molecules by titrating mAb from the syringe (300 µl of 200 µM solution) into a 20 µM P405arom solution in the sample cell (1.5 ml). The instrument used is a VP-ITC available in the laboratory. Although saturation was not reached, sufficient titration data points were available for estimation of $K_D$, which was found to be about 10 µM.

Using seven crystallization kits (basic PEG, MPD and salt kits) and the concentrated P450arom-F(ab')$_2$ complex, we have screened about 200 separate crystallization conditions. Microcrystals observed in one such experiment were washed and subjected to SDS-PAGE analysis where they showed the presence of P450arom as well as the heavy- and the light-chain antibody fragments in nearly the same relative concentrations as in the starting material. Native gel mobility analysis of the complex from the microcrystals showed that the complex moves as a single molecule of 260 kDa. We have obtained needle-shaped crystals of the complex from 15% methylpentanediol and 0.2M sodium citrate in 0.1M HEPES at pH 7.5. However, these crystals, yellowish in color, are not large enough yet for X-ray diffraction. Optimization of the crystallization conditions is underway.

K. Expression of Recombinant P450arom in Insect Cells

In the past, several laboratories attempted to express crystallization-quality recombinant wild type and mutant P450arom [57-61]. Now that the native enzyme has been crystallized, renewed efforts to grow crystals of the recombinant enzyme under similar conditions have a better chance to succeed. We obtained a bacterial expression clone of Del38arom, the amino-terminal trans-membrane domain deleted P450arom (City of Hope, Calif.). This protein, expressed in the inclusion body, was solubilized with emulgen and purified by the mAb 3-2C2 immunoaffinity chromatography. After exchanging the detergent with BNM using a HA column, the purified enzyme showed low specific activity (<<1 nmole/min/mg). In contrast, purified placental enzyme in BNM has a specific activity of 10-50 nmole/min/mg. The yield was typically less than 0.5 mg per liter of culture. Several optimization experiments using various cell growth and induction temperatures as well as denaturation and renaturation conditions failed to improve either the quantity or the quality of the final product.

Consequently, we pursued a baculovirus expression clone of Del38arom. In order to use the baculovirus system, the gene was cloned into a pBAC-2 cp transfer plasmid with segments of ORF 603 and ORF 1629 flanking the polh promoter. Initially, the Del38arom gene was PCR-amplified from a pET3b-aro vector. Then, the product was inserted into pBAC-2 cp using Novagen's ligation-independent cloning kit. Positive clones were confirmed by sequencing. The recombinant baculovirus was then constructed by co-transfecting pBAC-2 cp-Del38arom with linearized virus DNA, provided by Novagen's BacVector-3000 transfection kit, into Sf9 (*Spodoptera frugiperda*) insect cells following the technique of cationic liposome mediated transfection. This BacVector-3000 Triple Cut Virus DNA has eight non-essential genes deleted in order to eliminate the competition of cellular resources from our target protein. After the co-transfection, we had a supernate containing the active, viable virus, 95% of which were recombinant. We performed two rounds of plaque purification in order to isolate pure recombinant virus away from uncut viral DNA.

In one protein expression experiment, IL of Sf9 cells at 91% viability was infected Del38arom master stock. The infected Sf9 cells were harvested at 72 hours post-infection at 80.5% viability, homogenized in 10 mM potassium phosphate containing 20% Glycerol, 0.1 mM EDTA, 0.5 µM androstenedione and 0.15% emulgen, and subjected to sonication. Del38arom in the soluble fraction was first purified with Ni-affinity chromatography (using the amino-terminal 6× Histidine tag) and then with an immunoaffinity column containing cross-linked mAb 3-2C2. A SDS-PAGE and western blot of various fractions from the mAb 3-2C2 column were obtained. Further optimization of expression and purification of the recombinant Del38arom are currently underway. Expression of the full-length enzyme in the Sf9 insect cells is also in progress.

L. Newly Synthesized Potential Inhibitors of P450arom

Figure 17:
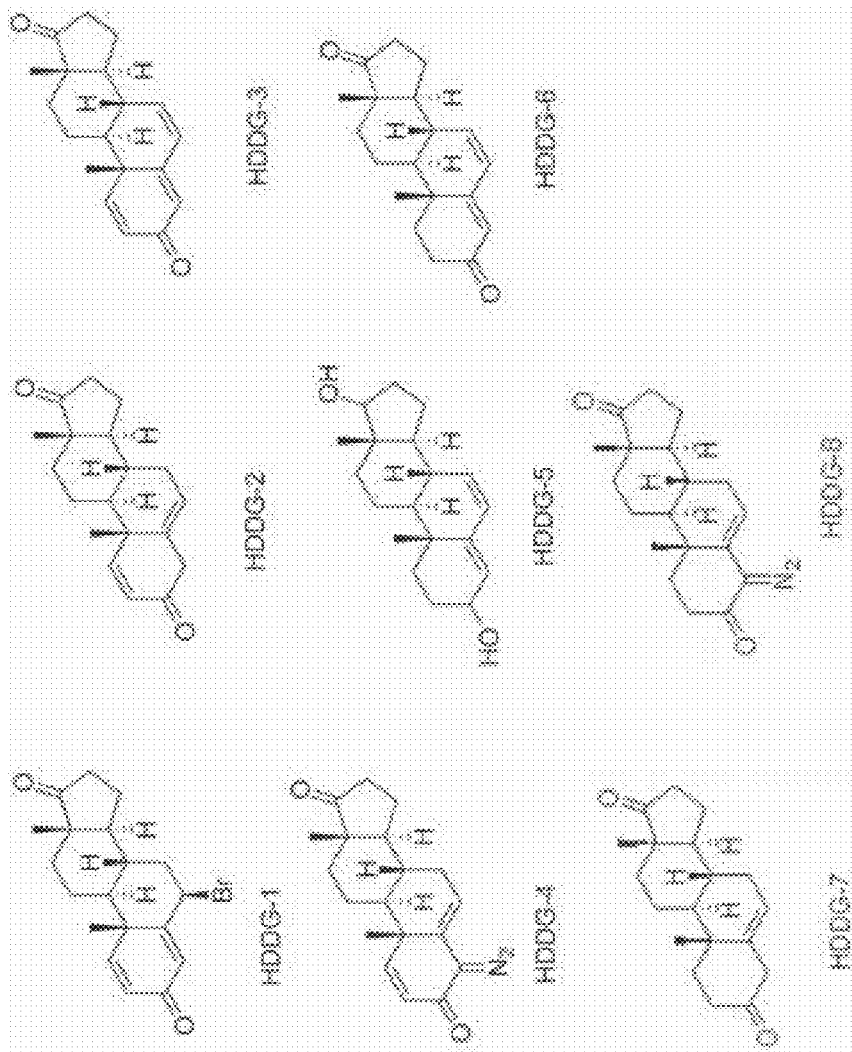
FIG. 17 shows newly synthesized androstenedione analogs as potential inhibitors of P450arom.

Others have synthesized 8 new androstenedione-analog compounds as potential inhibitors of P450arom (FIG. 17). Because of their similarity with androstenedione, all these analogs fit comfortably in the substrate-specific narrow active site cavity, but are likely not to be aromatized by P450arom. We will now test them for their inhibitory properties.

M. Cloning, Expression and Purification of Human Cytochrome P450 Reductase (hCPR)

Full-length human cytochrome P450 reductase (hCPR) cDNA was subcloned into the pFLAG-CTS expression vector using the HindIII/BglI restriction sites. A stop codon was included at the c-terminal end of the gene to prevent expression of the FLAG peptide affinity tag. Upon sequence confirmation, the plasmid was then transformed into BL21(DE3) cells for protein expression studies. Preliminary expression was done in LB media and was shaken at 220 rpm at 30° C. to $OD_{600}$ 1.0, at which point 2 mg/ml riboflavin and 0.5 mM IPTG were added. Expression of the hCPR protein was then carried out at 30° C. for approximately 18 hrs. hCPR protein expressed well, but found in the insoluble fraction. Insoluble hCPR was solubilized in 0.1% Triton X100 and purified using a 2'-5'-ADP Sepharose 4b column. Results were analyzed by SDS-PAGE analysis. Further purification will be done using a QHP ion-exchange column.

Examples 7-11

Examples 7 through 9 below relate to experimental procedures such as purification, assay of activity, and crystallization of complexes of P450arom, and methods involving X-ray diffraction data collection, structure solution, and refinement applicable to structure elucidation processes. Examples 10 through 11 describe the plan for structure-guided design, docking and ligand library screening procedures, as well as the plan for synthesis of new inhibitors.

Example 7

Substrate Recognition Mechanism: Structures of P450arom with Androstenedione, Testosterone, and 16α-Hydroxytestosterone We hypothesize that the atomic details of the active site bear the evidence of the specificity and, in order to elucidate the structural basis for the specificity, it is essential that binding modes of the steroid backbones are determined experimentally. Since P450arom exhibits nM affinity for androgenic substrates androstenedione (A), testosterone (T), and 16α-hydroxytestosterone (HT), crystallization of P450arom in the presence of 10's of µM concentrations and at ~10-fold molar excesses of the substrates in the crystallization media would suffice to trap the steroid molecule in the active site. This approach is especially valid for P450arom since the aromatization reaction cannot be initiated in the absence of CPR -supplied electrons. The solution of the first crystal structure at 2.90 Å showing the bound A in the active site proves the validity of this strategy. We will continue to adopt the same approach for the other two substrates, T and HT. We have shown that the crystal quality can be improved by reporting in this revised application diffraction data better in quality and resolution than the data shown in the first application. We will continue to work towards improving the data resolution by growing superior-quality crystals.

A. Purification

The full procedure of purification of P450arom from human placenta has been described elsewhere [51 and references therein]. Briefly, frozen human placental homogenate is thawed overnight and further homogenized in a 0.3% solution of emulgen and Na cholate. The solution containing solubilized proteins is applied overnight to a mAb3-2C2 immuno-affinity column. P450arom is eluted from the column with 4M NaCl. The eluate is immediately applied to an equilibrated G-25 column for desalting and then to a HA column. P450arom is eluted from the HA column with 100 mM phosphate buffer. The fractions containing the P450arom are pooled and applied to a G-25 column for desalting. All procedures are carried out at 4° C. As an alternative approach to the traditional column chromatography under gravity, our plan is to employ high performance liquid chromatography under high pressure with an AKTA Purifier (GE Healthcare, Piscataway, N.J.). A high performance, high throughput system will further reduce the purification time.

B. Detergent Exchange

A HA column is used for exchanging emulgen to n-nonyl-β-D-maltopyranoside (BNM) or n-dodecyl-β-D-maltopyranoside (BDM). The solution containing P450arom is applied to an HA column equilibrated with 50 mM phosphate buffer containing emulgen and washed with 5 bed volumes of the same buffer. The HA column is washed with 5 bed volumes of the buffer containing 2 mM BNM. The column is then incubated for 1 hour prior to elution. The column is eluted with 200 mM K-phosphate containing 2 mM BNM (or 1 mM BDM).

C. Activity Assay

We will continue to measure the enzyme activity as has been previously described. Briefly, the purified P450arom is reconstituted with CPR and 1,2-Diarachidoyl-sn-glycero-3-phosphocholine. Reconstituted P450arom is preincubated with the substrate, [1β-$^3$H, 4-$^{14}$C] androstenedione. The aromatase reaction is started by addition of NADPH. The reaction is terminated by the addition of trichloroacetic acid and charcoal. The mixture is centrifuged, and the supernatant is filtered through a cotton-plugged disposable Pasteur pipette. The $^3$H water in the eluate is assessed according to the 1β elimination mechanism (75% release into water) [50].

D. Crystallization: Optimization of Conditions for Improved Resolution

The procedure similar to that previously yielded diffraction-quality crystals for the P450arom-A complex will be employed to grow crystals of other complexes. However, we will perform a thorough fine tuning of the crystallization conditions in order to boost the diffraction limit. Parameters to be optimized include glycerol, detergent, and protein concentrations. Both BDM and the newly discovered BNM will be the detergents of choice. Furthermore, we will experiment with the addition of small amounts of various phospholipids, such as 1,2-linoleoylphosphatidylcholine (DLPC) and 1,2-oleoylphosphatidylcholine (DOPC) to enhance the internal long-range order of the crystals. Addition of lipids was shown to improve the diffraction limit of membrane-bound protein crystals [62]. We will screen for the optimum cryo-protecting agent for each of the P450arom-small molecule complexes. Some of these optimization techniques have already been implemented with a boost in the diffraction limit to better than 2.9 Å. Further improvement in the quality of the P450arom-A complex crystals, growth of crystals of new complexes (with T and HT), and/or growth of another crystal form with better diffractability may require new screening for optimal crystallization conditions and special crystallization experiments using several available alternative approaches. A brief summary of these techniques is provided below:

E. Special Crystallization Experiments

We plan to conduct the following systematic experiments for the growth and growth-optimization of superior diffraction-quality crystals of P450arom-ligand (substrate and inhibitors) complexes through these five available approaches: (i) additional optimization of the condition under which the latest single crystals are grown, (ii) buffer-based optimization: five new buffers and pH's at which the purified enzyme is to be prepared and set up for crystallization, (iii) utilization of the HWI's high-throughput robotics crystallization laboratory's the $5^{th}$ generation 1536 screen, (iv) utilization of the Z/3 plate technology to tailor time course of equilibration, and (v) use of the recombinant single-chain Fv (scFv) of the monoclonal antibody 3-2C2 in crystallization.

(i) Optimization of the condition under which the latest single crystals are grown: We plan to conduct a fine grid search by varying the (a) starting PEG (2K-10K) concentration (10-20%, in steps of 1%), (b) final reservoir concentration (22-40%, in steps of 1%), (c) protein concentration (20-45 mg/ml, in steps of 2 mg/ml), (d) substrate/inhibitor concentrations (0.1-0.5 mM), (e) the protein to reservoir addition ratio from 1:1 to 5:1, and (f) salt additives, such as sodium chloride, ammonium sulfate, magnesium chloride, ammonium phosphate, etc at low concentrations and amphiphile additives such as 1,2,3-heptanetriol. In addition, buffer/pH-based screening and variation of equilibration kinetics using Z/3 plates (both described below) will be undertaken at these conditions.

(ii) Buffer-based optimization: New crystallization trials are to be undertaken at five new pH's using new buffers. Thus far, potassium phosphate buffer at pH 7.4 has been used exclusively for the preparation of the final protein solution. The new buffers to be tried are bicine pH 9.0, Tris.HCl pH 8.0, HEPES pH 7.5, MES pH 6.0, and citrate pH 5.5, each at an ionic strength of 100 mM. The final P450arom preparations will be thoroughly exchanged into these buffers. Both BDM and the newly discovered BNM at concentrations of 1-3 mM will be the detergents of choice.

(iii) Utilization of the HWI's high-throughput robotics crystallization laboratory's the $5^{th}$ generation 1536 screen: We also plan to use Hauptman-Woodward's high-throughput screening laboratory to screen 1536 fifth generation cocktails by the "microbatch under oil" method. These cocktails can be subdivided into three categories: (1) 570 Hampton Research crystallization screening solutions, (2) 233 Salt/Buffer (an incomplete factorial of 35 salts and 8 buffers) and (3) 733 PEG/Salt/Buffer (an incomplete factorial of 5 PEGs, 35 salts, 8 buffers). Any conditions yielding positive results in the microbatch experiments will be converted to vapor diffusion conditions and optimized by a fine-grid screen.

(iv) Utilization of the Z/3 plate technology to tailor time course of equilibration: This plate, containing 6 cells of equal diameter, but varying depth, is designed to allow control, over a period of time, the equilibration of a protein and reservoir solution using a solid salt and a known percent of precipitant solution to drive the rate of vapor diffusion. With increasing amounts of solid salt, the endpoint concentration increases, and the time needed for equilibration decreases, but the slope is dependent only on depth $(d)^2$ and not the magnitude of the endpoint. The $d^2$ dependence of diffusion is manipulated with reservoirs of varying depth to increase or decrease the rate of equilibration [63]. The reservoir cell contains a salt solid base, overlaid with a set percentage of PEG solution and then a thin layer of water is added as a final layer. The idea is that is that as the salt dissolves and mixes with the PEG solution (hence actually dehydrating the solution), the vapor pressure of water in reservoirs is reduced driving dehydration of the protein droplet. P450arom will be exchanged into 100 mM Bicine, pH 9.0 (or any other buffer of choice), 20% Glycerol, 0.5 mM DTT, 0.5 mM A (or other substrates/inhibitors) and concentrated to ~30 mg/ml. At this point, 12-30% solutions of PEGs 400, 550 mme and 8000, as well as various concentrations of MPD (with all solutions in 100 mM Bicine, pH9.0 or other chosen buffer, 20% Glycerol, 0.5 mM DTT) will also be added in an equal volume. Volumes of this mixture will then be pipetted into the modified dialysis buttons, placed into the z/3 plate as described in literature, sealed with tape and placed at 4° C. Observations will be done at 1 day, 1, 2, 3 and 4 weeks.

(v) Use of the recombinant single-chain Fv of the monoclonal antibody 3-2C2: We have designed, cloned and expressed two single-chain fragments (scFv1 and scFv2) of the light and heavy chain variable domains of mAb 3-2C2. One of them, scFv2, has been shown to inhibit P450arom activity in a dose-dependent manner with an $IC_{50}$ value of about 1 µg/ml, similar to that of the intact mAb IgG [50]. The expression level of scFv2, which currently stands at about 1 mg of purified protein per liter of culture, will be further optimized for the purpose of co-crystallization with P450arom. Complex formation will be achieved by titrating scFv2 into a dilute (~2 mg/ml) solution of purified P450arom and monitoring inhibition. The complex solution will then be concentrated and crystallization will follow. Hopefully, scFv complexes of P450arom will yield better diffracting crystals (tighter packing dictated by inter-scFv contacts and not by P450arom molecules), quite possibly in a new crystal form.

F. X-Ray Diffraction

Initial crystal characterization and preliminary data collection will be carried out first at the in-house R-AXIS IV image plate detector system. Crystals will be flash frozen by plunging into liquid nitrogen and will be maintained at 100° K using a cryo-cooling device. Cryo-protectant solutions made with various combinations of ethylene glycol, PEGs, glycerol, and MPD will be used to find the optimum for each complex. Intensity data to determine and refine the crystal structure at the resolution limit will be gathered at a high flux synchrotron X-ray source. Anomalous scattering data will also be gathered for structures requiring phase determination, i.e. the first P450arom-complex; this data may also be useful for locating the heme iron in P450arom. For the collection of iron anomalous signal, synchrotron X-ray will tuned to the Fe K-absorption edge energy of 7.1234 keV (wavelength=1.7405 Å for a maximum value of f" of 4.34e⁻ that yields the maximum Bijvoet difference). Alternatively, we will attempt to gather the Fe-anomalous signal at the home source using Cu $K_\alpha$ X-radiation (wavelength=1.542 Å). If necessary, we will collect data on isomorphous heavy atom derivative crystals of P450arom complexes for obtaining the experimental phases. Intensity data will be processed by the software package HKL2000 [52] and/or MOSFLM [64]. In an alternative approach to the liquid nitrogen cooling, we will attempt to flash cool the crystals in liquid propane, which has a higher boiling point (231° K) than liquid nitrogen and a melting point (83° K) far removed from the boiling point. It is, thus, possible to avoid the formation of a gaseous insulating film on the crystal surface due to boiling of liquid nitrogen during the flash cooling. However, liquid propane is not the first choice cryo-coolant because of the fire hazard issue.

G. Structure Solution and Refinement

X-ray crystallographic determination of the structures of P450arom complexes will follow a standard protocol. This involves, first, phase determination by multiple heavy-atom isomorphous replacement, anomalous scattering, molecular replacement, or any combination of these techniques. For the P450arom structure, anomalous scattering from the heme iron will be fully exploited. This step will be followed by interpretation of the electron-density maps and building of an atomic model using computer graphics. Finally, the atomic model will be refined.

Combining iron anomalous dispersion data with a molecular replacement search solution has now solved the first P450arom structure. One technique that was successfully utilized in the past was the use of a cross-phased isomorphous or Bijvoet difference map to identify the correct molecular replacement solution when the homology with the search model was marginal [65]. Another approach successfully implemented in the past was the use of a weighted average of several low homology models as the search model for finding a molecular replacement solution [65]. The refined structure of the P450arom-A complex will be used to solve all other P450arom-complexes using the molecular replacement method and/or difference Fourier synthesis. For obtaining a solution for the structure of a complex of P450arom with F(ab')$_2$/Fab'/IgG, molecular replacement search with the known Fab crystal structure [66] may also be employed. Furthermore, full exploitation of the molecular averaging techniques will be made to improve the electron density maps whenever possible.

One or more model-building routines such as XTALVIEW [67], CHAIN [68], O [69] and Coot [54] running either on a Silicon Graphics Octane2 or on an Apple dual-processor G5 workstation will be used. Protein models will be refined by the simulated annealing/maximum entropy methods using programs such as XPLOR [70], CNS [71] and Refmac5 [55]. The quality of the structures will be assessed with a number of available software, such as PROCHECK [72] and WHAT_CHECK [73], and analyzed with computer graphics display packages.

As an alternative approach, if obtaining a conventional solution for the phase problem fails, we will iodinate the tyrosine residues [74] and use the combined isomorphous replacement and anomalous scattering signals from iodine atoms to solve the phase problem.

H. Anticipated Outcome

The methods described above will yield the crystal and molecular structure of P450arom, from which a complete atomic description of the active site, along with the binding interactions of A, T and HT will emerge. The same methodology could be adopted to elucidate the structures of other P450arom complexes with other small molecules, such as inhibitors and reaction intermediates. Optimization of the crystallization conditions described above, in conjunction with the presence of various tight-binding inhibitors/substrates in the crystallization media, is expected to improve the resolution limit to 2.5 Å or better for at least some of the complex crystals.

Crystallization and structural investigation of the full-length native P450arom could potentially pose numerous problems, namely, purification difficulties, limited amounts of protein, presence of hydrophobic trans-membrane domains, heterogeneity due to glycosylation, and the lack of ability to probe the structure-function questions with site-directed mutagenesis. In this application we demonstrate that our methodology and approach have successfully overcome all of these potential roadblocks except one: the ability to mutate an amino acid. A recombinant expression that expresses functionally active enzyme is clearly preferable in this regard. With future mutational studies in mind, we continue to pursue expression of Del38arom in insect cells. In this regard, an exciting new result is the demonstration of the existence of a soluble form of the enzyme expressed in insect cells in purifiable quantities (see section C.9). Once the protein expression is optimized, we will proceed with the purification and activity assay of Del38arom.

Example 8

Molecular Basis for Inhibition: Structures of P450arom-Inhibitor Complexes

A. Hypothesis, Rationale, and General Approach

Many small molecule inhibitors of P450arom have been identified [75,76]. The objective here is to understand at the molecular level how the most potent P450arom inhibitors that are being used as drugs in hormonal breast cancer bind the enzyme at or near the active site in preference to its own natural substrates. Our presumption is that crystal structures of these complexes will reveal very specific ligand-protein interactions conducive to inactivation of the enzyme. The long-term objective is to develop potent, reversible P450arom inhibitors by exploiting the complete binding-site structure.

B. Crystallization of Inhibited Complexes

P450arom complexes with high affinity inhibitors exemestane, formestane, letrozole, aminoglutethimide (all from LKT Laboratories, St. Paul, Minn.), anastrozole (gift from Astrazeneca, Cheshire, UK), and fadrozole (gift from Novartis, Basel, Switzerland) will be prepared and crystallized. The complexes will be prepared in the same way previously described. Purified P450arom will be concentrated to 20-30 mg/ml and concentrated solutions of ligands (10-30 mM in polyethylene glycol 400/550) will be added to it, such that the final inhibitor concentrations range between 0.5 and 1.0 mM. This will ensure at least a 1:1 to 2:1 inhibitor to protein molar ratio in the crystallization drops. The solutions will be thoroughly mixed and incubated before being set for crystallization by the sitting drop vapor diffusion method. Using this protocol, nearly 100% inhibition of P450arom has been observed for exemasten and letrozole (Table 3).

C. X-Ray Data Collection

The P450arom-inhibitor complex crystals will first be examined for quality at the home X-ray source. The intensity data up to the resolution limit will be gathered at a synchrotron X-ray source.

D. Structure Determination and Refinement

Once the first crystal structure of the P450arom-A complex is determined, a molecular replacement search and/or a difference Fourier synthesis will be sufficient to determine the structure of a new complex and build the model. The model will then be refined as usual.

F. Anticipated Outcome

We anticipate elucidating the structures of these six enzyme-inhibitor complexes without much difficulty.

If the solubility of any inhibitor under the crystallization conditions becomes as issue, the inhibition experiment will be carried out at a much lower concentration of the enzyme (~1 mg/ml; 0.02 mM) in order to achieve the desired inhibitor to protein molar ratio. After incubation, the complex solution will be concentrated to the desired molarity and set-up for crystallization. Similar methodology was previously used to determine the crystal structure of an enzyme-inhibitor complex prepared with a highly hydrophobic competitive inhibitor [77]

Example 9

Catalytic Pathway Identification of Reaction Intermediates

A. Hypothesis, Rationale and General Approach

X-ray photons interact with solvent molecules in protein crystals liberating photoelectrons, which in turn create reactive species responsible for the radiation damage of protein crystals. These photoelectrons can react with heme-containing redox proteins such as cytochrome P450's and alter their redox states. For enzymes like P450arom, catalysis can be initiated by the creation of such photoelectrons, especially when the enzyme has a substrate bound at the active site in the oxidized $Fe^{3+}$ state, and the availability of oxygen is sufficient to complete the reaction. The absorption spectrum of crystallized P450arom exhibits a Soret band at 394 nm, characteristic of the presence of an oxidized $Fe^{3+}$-A complex. It is also known that the Soret bands of P450arom have different maxima between 394 nm and 450 nm representing different redox states of the heme iron and the formation of various reaction intermediates. We, therefore, hypothesize that by following the absorption spectra of the crystal while collecting the diffraction data, we will be able to determine the X-ray dose-dependence of the Soret bands, isolate diffraction data belonging to each redox state, and determine the crystal structure of each state, thereby capturing snap-shots of the reaction intermediates. Similar methodologies have been successfully applied to determine catalytic pathways in horseradish peroxidase [78] and cytochrome P450cam [79], but not microsomal P450's. The experiment has the potential of yielding direct structural evidence for reaction intermediates, leading to the formulation of a molecular mechanism for the P450arom-catalyzed aromatization reaction.

B. Measurement of Absorption Spectrum in a Single Crystal

A specially designed single crystal spectrophotometer adoptable to a generic X-ray diffractometer system used in synchrotron beam lines is commercially available (4DX Systems AB, Uppsala, Sweden). Components of the spectrophotometer system that can also be readily assembled at an X-ray beam line are also commercially available (Ocean Optics, Dunedin, Fla.). The spectrophotometer is made essentially of the following components (1) an optical goniometer that accepts standard heads consisting of an observation microscope, sample illumination system, polarizers, and crystal mounting adjustments, suitable for handling cryo-cooling of crystals, (2) a fibre optics illumination lamp for sample illumination, alignment and manipulation, can be used for spectral measurements at wavelengths 350-800 nm, (3) optical microprobes consisting of two sets of mirror lenses, (4) quartz optical fibers, and (5) a computer-interfaced monochromator and CCD detector system that can be housed outside the experimental hutch. The set up and software allow for simultaneous real time measurement of absorption spectrum and X-ray diffraction intensity on the same single crystal. For P450arom crystals, the absorption spectrum will be recorded in the range of 350-550 nm, at the maximum rate of one spectrum per frame of the recorded diffraction data. The spectra will be analyzed to identify and isolate dose-dependent transitions of the Soret bands. Thus, the electronic (Soret band) transitions identified by the spectral analysis will be correlated with the anticipated structural transitions recorded as a set of diffraction images.

C. Diffraction Data Collection

The diffraction data will be gathered at a synchrotron X-ray facility equipped with a single crystal spectrophotometer (like the one described above), such as the Advance Photon Source (APS; BIOCARS 14-BM-C) and the Stanford Synchrotron Radiation Laboratory (SSRL) beam lines. For the space group of the P450arom-A crystals, 90 frames of data, each a 1° oscillation image, for a total of 90° rotation of the crystal is sufficient to cover the unique diffraction space. A data collection strategy using multiple crystals [78] will be employed so that a complete data set for each Soret band transition corresponding to an X-ray dose can be measured. In order to achieve this, an estimated 9 fresh crystals will be used to record diffraction images assuming a maximum of 5 Soret transitions. Each crystal will be mounted in the same orientation with respect to the X-ray beam, with its hexagonal rod axis aligned along the rotation axis and the "zero" of the rotation axis defined at a fixed position of the hexagon. All 90 frames of data, equivalent to 90° rotation of the crystal, will be recorded from each crystal. However, the beginning frame position of each crystal will be advanced by 10° from that of the previous crystal. Using this protocol, each 10° "wedge" of the diffraction space covered by one crystal will receive the same average X-ray dose as the corresponding wedges from all other crystals while recording different regions of the 90° diffraction space. Thus, when these successive wedges of data from all the crystals are combined for the entire 90° diffraction space, the result will be 9 complete data sets with increasing average X-ray dose, roughly from 11% to 100%, each in all likelihood representing one protein structure and one electronic state. The number crystals used and the wedge width will be adjusted up or down depending on the nature and the number of Soret bands as a function of the X-ray dose, recorded for the first crystal. The data processing methodology will be the same as described before.

D. Structure Solution, Refinement and Analysis

With an already known structure of the P450arom-A complex, we will proceed directly with the refinement of these structures.

E. Anticipated Outcome

It is quite likely that by employing this technique, we will be able to provide direct structural evidence for reaction intermediates that have been proposed over the years. Some of the findings could potentially be paradigm shifting.

The experiment has the potential of yielding important results provided the electron densities have high enough clarity for the small structural differences among dose-dependent structures to be discernable. At the current ~2.7 Å resolution of the P450arom-A complex crystals, fine differences might not be readily interpretable. However, it is quite likely that optimization of crystallization described above will improve the resolution. Our goal is to conduct this experiment at least at 2.5 Å or better. Furthermore, the photoelectron production rate and available dissolved oxygen will have a direct impact on the outcome. The electron levels can be controlled by adding either an electron scavenger or dithionite in the cryo-protection solution. If deemed necessary, we will bubble oxygen through cryo-protection solution before cryo-cooling of the crystals.

The issue of how to discriminate between conformational changes due to electron transfer and changes in the protein structure due to radiation damage: The experiment for this specific aim is designed to correlate the diffraction data with changes in the electronic state of the heme group. Therefore, only those changes in the structure that synchronize (in time and in X-ray dose) with spectrophotometric transitions (change in the Soret band) are interpretable as due to an electronic transition. Furthermore, we will focus our analysis of structural changes (due to an electronic transition) on the neighborhood of the heme group, possibly on the substrate and on the catalytic residues in its immediate vicinity. First, any structural change in the active site that does not synchronize with a Soret transition will be treated as a non-catalytic event. A structural change due to radiation damage would show up as unrelated to a Soret transition. Indeed, radiation damage-related changes may coincidentally occur during a Soret transition, or within the 10° data space where we assume no conformational shifts are occurring. These situations could pose problem for interpretation. Secondly, the Soret transitions (and the related catalytic events) will be few and discrete events isolated in time, whereas the radiation damage is a continuous and a cumulative process. Therefore, if we can detect those discrete events spectrophotometrically and limit our observation on the changes of the substrate and its immediate neighborhood, we may be able to avoid having to deal with changes due to radiation damage. Unavoidably, though, any structural changes in the catalytic cavity due to radiation damage occurring between two Soret transitions will complicate the interpretation. Nevertheless, by repeating the experiments a number of times and identifying the electronic transition points in time and in X-ray dose, we will be able to isolate the catalytic event-related changes and identify the reaction intermediates.

Ideally, if the experiment can be repeated in the absence of a bound substrate, non-catalytic events, such as radiation damage or structural transitions not related to catalysis can be identified and accounted for.

Example 10

Initiation of New Inhibitor Design, Synthesis and Assay

A. Hypothesis, Rationale, and General Approach

The hypothesis is that analysis of the wealth of structural information emerging from the complexes of the enzyme with substrates, inhibitors, and reaction intermediates will permit us to begin exploring rationally the entire conformational space of the ligand-binding site leading to the design, synthesis and testing of new inhibitors of P450arom with drug-like properties and high specificities. Although the current inhibitors have high affinities, they are not necessarily exclusive for P450arom. The structure-guided approach will address the exclusivity issue. Furthermore, identifying reaction intermediates could enable us to develop novel inhibitors that are transition state analogs. There are three general approaches towards achieving the objective described here: (i) synthesis of new inhibitors through optimization/modification of substrates/existing inhibitors by incorporating the shape and charge complementarity of the active site as well as chiral centers, (ii) virtual screening of compounds in a database utilizing the known active site structure of P450arom, and (iii) de novo design into the entire conformational space satisfying the shape and charge complementarity and/or mimicking the transition states. While the approaches (i) and (iii) could generate new inhibitors that may have undergone some active site optimization, the approach (ii) is a rapid way to identify already known and purchasable inhibitors that may serve as lead compounds without having to go through chemical synthesis. The hypothesis here is that some steroidal and non-steroidal compounds among the millions that exist in ligand libraries and are analogous to the P450arom substrates in shape, size and charge, could specifically bind at the active site as inhibitors of the enzyme. We expect to identify the most promising candidates by computer-based docking and scoring analysis. Once the high-scoring compounds are purchased and assayed for activities in the laboratory, further optimization of promising ligands can be done by synthesis of more specific interactions within the binding site environment, eventually yielding optimally active and selective inhibitors.

Standard procedures of virtual ligand library screening will be adopted to identify these existing compounds. ZINC (ZINC Is Not Commercial) ((zinc.docking.org), University of California, San Francisco) database containing ~5 million commercially available drug-like molecules and anticancer agents, will be used for this purpose. The objective is to conduct selective search and virtual docking with steroid-like molecules or with non-steroidal molecules that have properties such as overall size, hydrophobicity, and numbers of proton donors and acceptors similar to those of steroids. The Molecular Operating Environment (MOE; Chemical Computing Group, Montreal, Canada) and SYBYL (Tripos, Inc, St. Louis, Mo.) software packages will initially be used in this work.

B. New Inhibitor Synthesis

Figure 13:
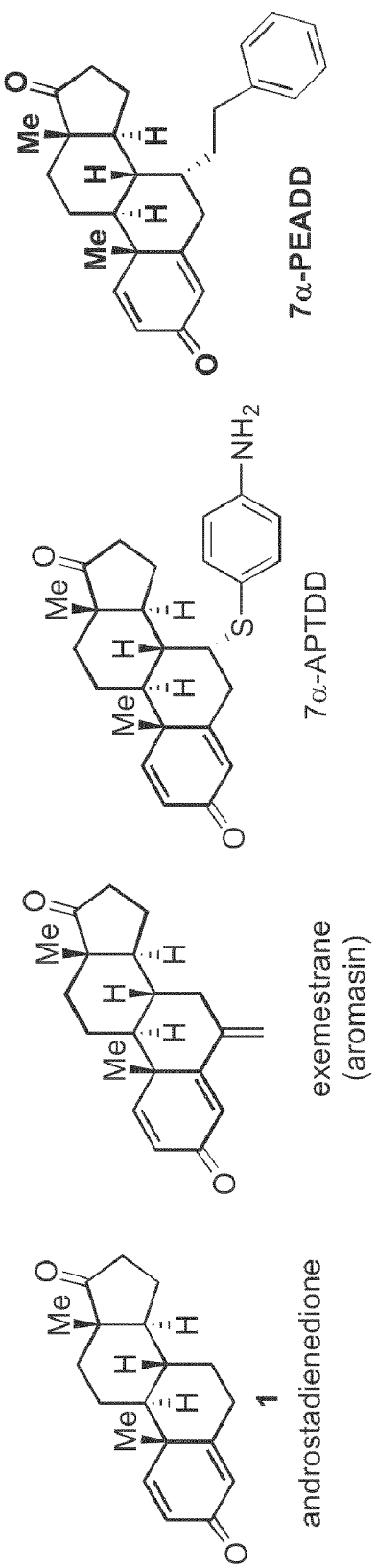
FIG. 13 shows chemical structures of some of the notable steroidal inhibitors of P450arom.

The availability of structural information about P450arom opens up the possibility for the design of novel inhibitors. Two major classes of inhibitors are known, the steroidal and non-steroidal inhibitors, and both block the biosynthesis of estrogens from androgens. One overlooked component that plays an important role in the design of potential therapeutic agents is whether or not the targets can be synthesized with reasonable efficiency. The synthetic accessibility has impacted the types of steroidal inhibitors that have been developed. Some of the most notable steroidal inhibitors are exemestane (aromasin), 7α-APTDD (7α-(4'-aminophenyl)-thioandrosta-1,4-diene-3,17-dione) and 7α-PEADD (7%-phenethyl-androsta-1,4-diene-3,17-dione) [75] (FIG. 13), which demonstrate that the C6 and C7 are tolerant to the inclusion of additional functionality. However, the selective functionalization of the steroid nucleus has long been considered a classic problem of organic synthesis. Consequently, a complete study of the types of functionality that could be accommodated at the C6 and C7 positions has not been achieved due to the limited range of conventional chemistry that can be used to make these analogs (conjugate addition and iminium chemistry starting from the readily available androstadienone or its unsaturated derivative). Furthermore, structural information emerging from the androstenedione- and exemestane-complexes of P450arom would dictate what other functionality could be introduced at these sites.

Although there are many historic methods for the synthesis of the steroid skeleton, the selective functionalization of commercially available steroids would be a much more attractive approach if a practical transformation could be developed. The major difficulty, of course, would be the requirement to control which of the many relatively unreactive sites in the steroid nucleus is manipulated in a controlled manner. Over the last five years we have developed a very powerful method for enantioselective C—H functionalization by means of rhodium carbenoid-induced C—H insertion [80,81]. This transformation displays spectacular levels of chemoselectivity and has great potential to lead to selective functionalization of the steroid skeleton. Therefore, the goal of the chemistry section will be to compliment the structure-guided drug design component by making available very different C6 and C7 functionalized steroid analogs as viable targets. By combining the molecular modeling studies, the novel synthetic leads and early biological in vitro screening data, we expect to identify novel classes of steroidal P450arom inhibitors.

Figure 14:
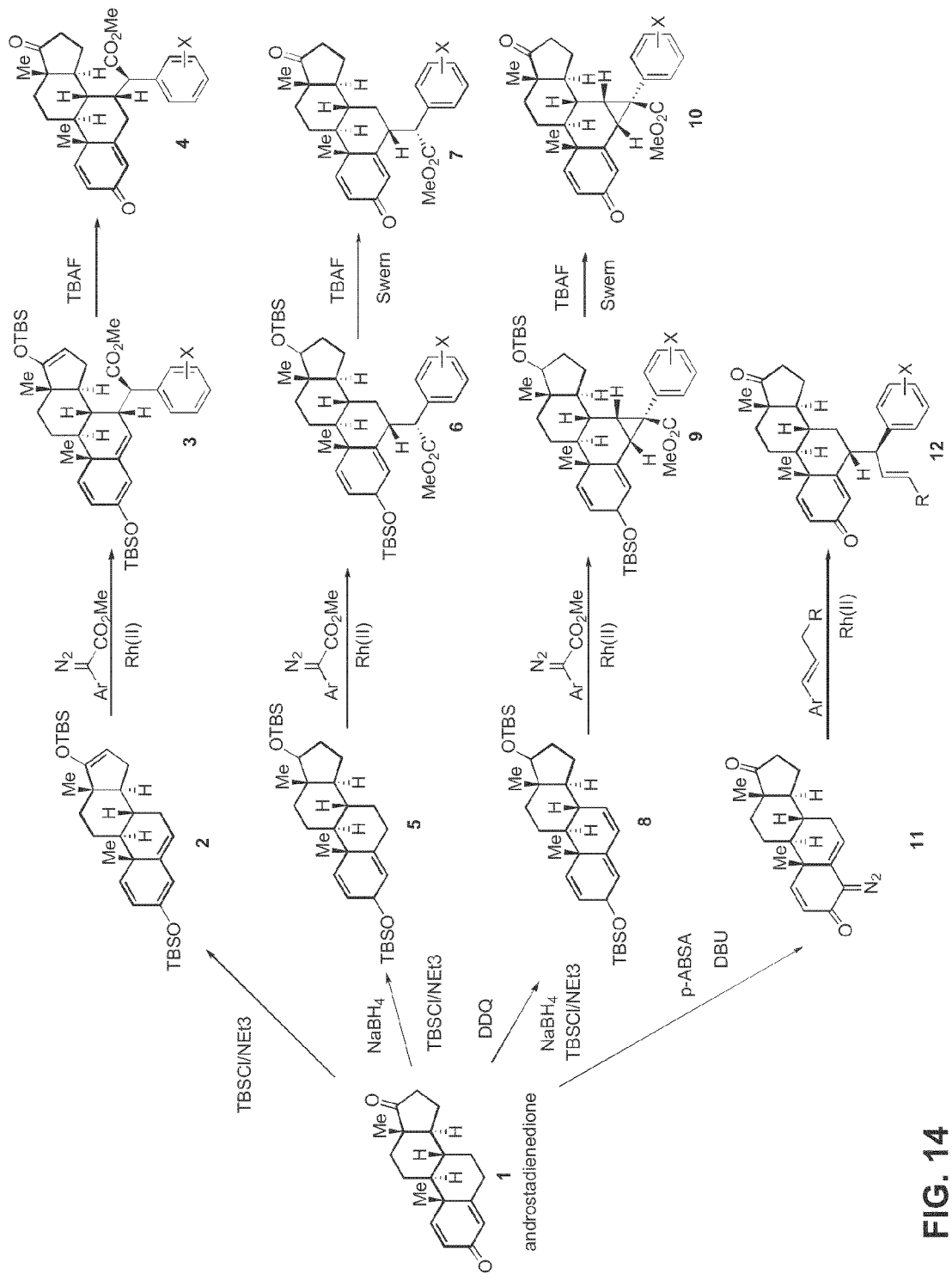
FIG. 14 shows chemical structures of the specific types of lead compounds for synthesis according to the present invention.

The specific types of modified substrates/inhibitors of P450arom that will be synthesized are summarized in FIG. 14. All of the proposed targets are derived from androstadienone (1) and all the synthetic schemes involve the use of novel carbenoid chemistry to introduce the structural diversity [80,81]. Silylation of 1 would be expected to generate 2, and then the carbenoid would be expected to cause C—H functionalization at C7 to form 3 [80,81]. Attack would be expected to occur from the alpha face, while the ester configuration would be controlled by which enantiomer of the catalyst is used. Desilylation would generate the target compound 4. If the reduced bis-silyl derivative 5 is used as substrate C—H functionalization at C6 would be expected to form 6 and then, after deprotection and oxidation, the target compound 7. These regiochemical predictions are made on the basis of our extensive studies on the electronic and steric influences that control this chemistry [80,81]. If the results deviate from our predictions, modifying the size of the silyl group should be a very useful controlling element [82]. Alternatively, the triene 8 would be expected to be susceptible to cyclopropanation, leading eventually to the cyclopropane target 10 [83]. An alternative would be to make the diazo compound 11 (this may be an interesting inhibitor in its own right because it could be a very useful photoaffinity agent), and then exploit the combined C—H activation/Cope rearrangement to form 12 [81]. As all the carbenoid chemistry is compatible with functionality that can be used in palladium catalyzed cross-coupling chemistry [84], interesting hits from 4, 7, 10, or 12 would be easily diversified if needed.

Figure 15:
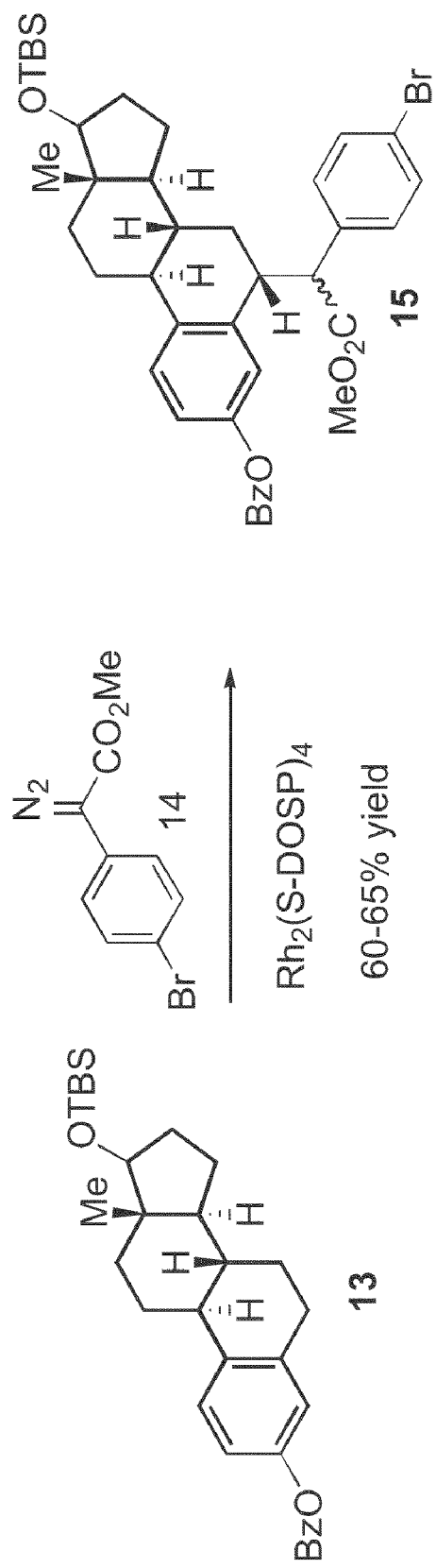
FIG. 15 shows selective functionalization of a steroid skeleton using an intermolecular C-H insertion.

We have conducted a proof of concept experiment to confirm that a steroid skeleton can be selectively functionalized using an intermolecular C—H insertion (FIG. 15). Reaction of the protected estradiol 13 with the p-bromophenyldiazoacetate 14, generated a diastereomeric mixture 15 of the C6 functionalized products in 60-65% yield. The diasteromeric mixture can be separated, but we have not yet completed the assignment of the relative configuration of the product. This is the first time that a steroid has been functionalized by means of an intermolecular C—H insertion and the highly regioselective nature of the reaction bodes well for a successful outcome to the proposed functionalization described in FIG. 14.

Figure 16:
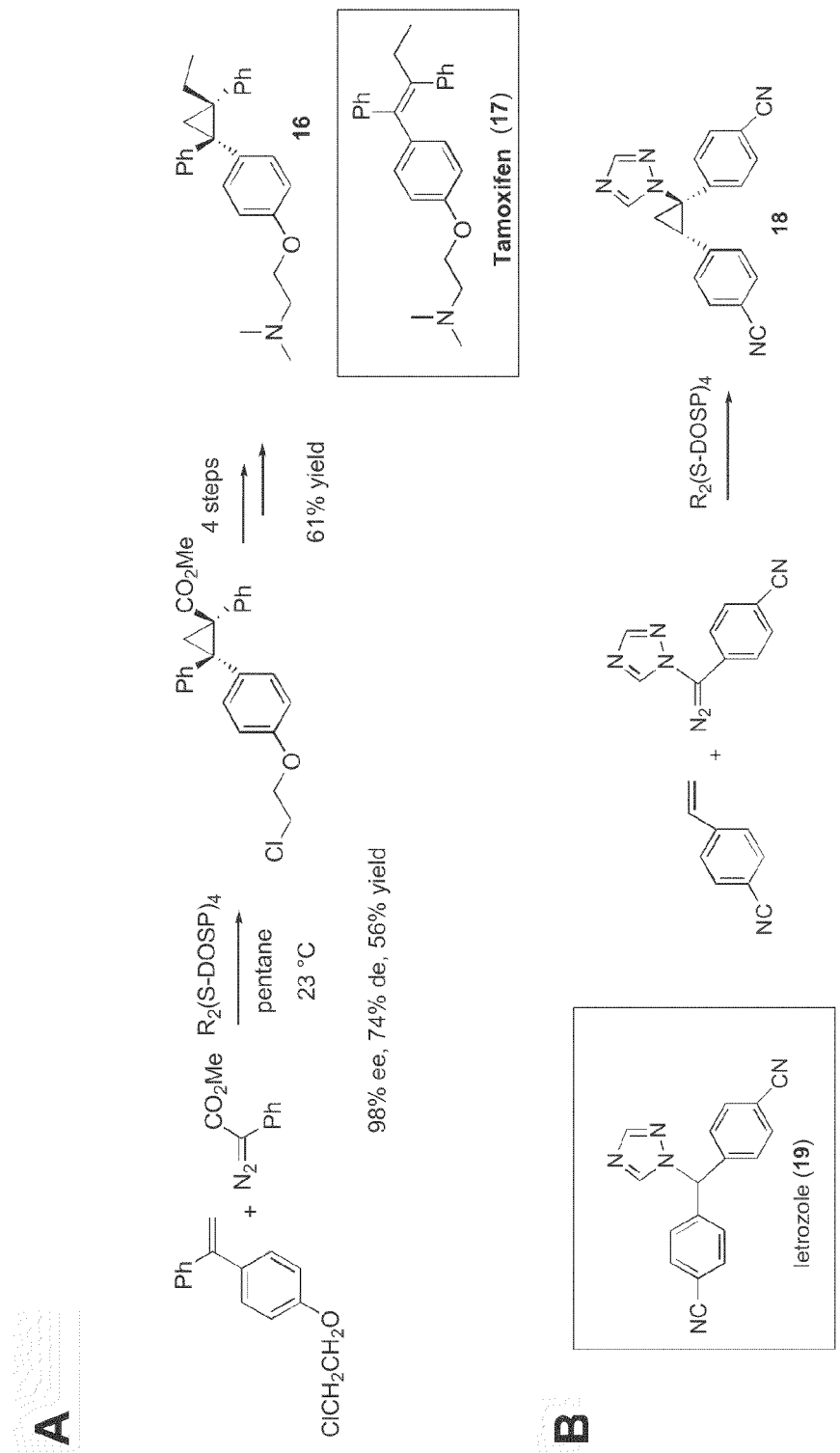
FIGS. 16A-16B: (A) A scheme for the synthesis of the cyclopropane analog of tamoxifen. Similar asymmetric cyclopropanation can be introduced in non-steroidal P450arom inhibitors, such as letrozole, as shown in (B).

The rhodium carbenoid enabling technology will also be used to make novel non-steroidal compounds as potential aromatase inhibitors. The approach will expand on our published method for the synthesis of 16, the cyclopropane analogue of tamoxifen (17, FIG. 16A) [85]. The central objective will be to make various cyclopropane analogs, such as 18, which will define more specifically the required aryl orientations of non-steroidal inhibitors such as letrozole (19). The target compound will be prepared by means of an asymmetric cyclopropanation as illustrated in FIG. 16B. Other structural orientations of 18 would be possible by modifying the diazo compound and the alkene trap. It is conceivable that the cyano groups may need to be introduced after the rhodium catalyzed reaction, in which the dibromo derivative of 18 will be initially formed, which then will be converted to 18.

The new enabling synthetic methods we have discovered in the last few years have great potential for the selective functionalization of steroids. The structural biology and modeling data, combined with our novel chemistry, offers an exciting approach for the discovery of novel P450arom inhibitors. The molecular modeling and virtual docking experiments will have a major influence on the design of synthesis targets as the project progresses.

C. Docking with MOE

Several automated docking routines are commercially available and have recently been reviewed [86]. The MOE-Dock routine searches for favorable binding configurations between a small, flexible ligand and a rigid macromolecular target. The docking utility calculates the lowest energy conformation of an enzyme-bound ligand. Crystal structures are used to validate the positioning of a ligand into the active site. The MOE package of software running on either a dual processor Apple G5 or a SGI Octane2 R12000 workstation is used to construct 3-D structures of inhibitor molecules, which are then energy-minimized. Searching is conducted at the site defined by the automated site finder, using one of two available search protocols (simulated annealing or tabu search) and a molecular mechanics forcefield MMFF94 from 11 different available forcefields. Both methods seek to optimize spatial contacts as well as electrostatic interactions. Default parameters for electrostatic (partial charges and dielectric constants), and for van der Waals interactions are used. The ligand geometry can be restricted during the search by imposing angle, torsion and distance constraints or restraints. MOE-Dock performs a series of independent docking runs and writes the resulting conformations and their energies to a molecular database file.

A protein structure is prepared for docking in the following manner: (1) hydrogen atoms are added to the target molecule; (2) partial charges of the side chains are defined; (3) heavy atoms are fixed and the hydrogens are subjected to energy minimization; (4) solvent molecules are removed from the binding cavity; (5) the binding site is chosen by the automated site finder routine that seeks and lists all possible ligand-binding sites contained within a receptor. The Alpha Triangle placement method generates "poses" by superposition of ligand atom triplets and triplet points in the receptor site. The receptor site points are alpha sphere centers (dummy atoms), which represent locations of tight packing; (6) conformational search on the ligand is conducted at the binding site and the score for each pose is calculated.

D. Scoring Function

There are many ways to define a scoring function, the purpose of which is to identify on a relative score scale the ligands and poses that would potentially have high binding-affinity for the receptor. We have used the scoring function used in MOE. By default, Dock uses the affinity dG scoring function to assess candidate poses. This function estimates the ethalpic contribution to the free energy of binding using a linear function: $G = C_{hb}f_{hb} + C_{ion}f_{ion} + C_{mlig}f_{mlig} + C_{hh}f_{hh} + C_{hp}f_{hp} + C_{aa}f_{aa}$ where the f terms fractionally count atomic contacts of specific types and the C's are coefficients that weight the term contributions to affinity estimate. The individual terms are, hb: interactions between hydrogen bond donor-acceptor pairs; ion: ionic interactions; mlig: metal ligation; hh: hydrophobic interactions; hp: interactions between hydrophobic and polar atoms; these interactions are generally unfavorable; aa: an interaction between any two atoms. This interaction is weak and generally favorable.

The score S contains the results of the scoring function as chosen (for the default function the unit is kcal/mol). The score ASE is proportional to the sum of Gaussians $R_1R_2\exp(-0.5d^2)$ over all ligand atom—receptor atom pairs and ligand atom—alpha sphere pairs. $R_1$ and $R_2$ are the radii of the atoms in Å, or is −1.85 Å for alpha spheres. d is the distance in Å between them; The scoring function E contains the score with which the poses are ranked; it is a linear combination of $\{ASE, S, E_{conf}\}$, where $E_{conf}$ is an estimated self-energy of the ligand in kcal/mol; smaller numbers mean better poses.

The rational for developing a scoring function is to include not only the binding energy of ligands, but also the terms to account for ligands' "drug-like" properties defined by the so-called Lipinski's rule of 5 [87]: (1) molecular mass less than 500 Daltons, (2) log P (hydrophobicity index (octanol/water partition coefficient) less than 5, (3) less than 5H-bond donors, (4) less than 10H-bond acceptors, and (5) less than 10 rotatable bonds. Various commercial packages use their own scoring functions for ranking the screening results. A recent comparative study with some of them show that the scoring functions rank the observed binding modes higher than the inaccurate poses provided that the experimental poses are available [88].

E. Virtual Screening of Compounds

Virtual screening of compound libraries will be conducted to identify existing but unknown ligands. The plan is to screen cancer preventive agents, chemotherapeutics, and natural products (such as flavonoids) that satisfy Lipinski's rule. ZINC and anticancer agent libraries such as the NCI database will be used for this purpose. Selective search and virtual docking will be conducted with steroid-like molecules as well as non-steroidal molecules that have properties such as overall size, hydrophobicity, and numbers of proton donors and acceptors similar to those of steroids. Several tools are available to determine affinity "hot spots" in the active site cleft [89]. Routines such as SuperStar [90] and DrugScoe [91] will be used for the purpose. We will build up a database for potential inhibitors of P450arom that are commercially available. This could be achieved by building up the current list by acquiring and archiving SMILES files (a readable format describing the chemical structure) for compounds.

F. De Novo Design

De Novo design will also be attempted implementing structural constraints obtained from experimental determination of substrate/inhibitor binding modes. The principle that guides such design is the complementarity of polar and hydrophobic interactions as well as of shape in the ligand-binding site. For the shape complementarity calculations, we will use FADE/PADRE and/or SHAPE routines (The Computation Center for Macromolecular Structure, San Diego Supercomputer Center, University of California, San Diego). Functional group substitution and/or multi-fragment search (as in MOE) will be conducted in accordance with shape and charge complementarity criteria. In order to examine alternative conformational states, models of inhibitors will be subjected to restrained dynamics simulation, followed by energy minimization. Variations in placement of the ligands will be explored using the program MOE-dock, which systematically searches the conformational space available to the inhibitor within the active site.

G. Rapid Inhibition Screening Assay of a Large Number of Compounds

The method for measuring P450arom activity using radio-labeled steroids has been described. Using microsomal P450arom preparations with known enzyme concentrations and activities, additional sample holder buckets and tube adaptors for the centrifuge, we will be able to able to assay the inhibitory properties of 10 compounds in about 4 hours' time. This rapid screening assay will help us to identify potential ligands/inhibitors among a large number of library compounds. Further measurements of $K_i$'s and the types of inhibition for promising inhibitors will be done from the Lineweaver-Burk plots using purified P450arom.

H. Anti-Proliferation Assay in a MCF-7 Cell Line Expressing P450arom

The human breast MCF-7 tumor cell line has been demonstrated to have the steroidogenic enzymes necessary to convert DHEA-sulfate/DHEA/A to E2 and has ERα. Scientists at the Mercer University, Macon, Ga., found low levels of 3β-HSD1 and P450arom in the MCF-7 Tet-Off cells from Clontech and stably transfected the cells with the genes that encode both of these human enzymes [92,93]. Western immunoblots with very specific polyclonal antibodies, produced in the Ghosh laboratory by injecting rabbits with pure P450arom and STS, show that our MCF-7 cells express STS and P450arom. Thus, this genetically engineered MCF-7 cells provide a useful model system to test the effects of new, rationally designed inhibitors of P450arom on the proliferation of human breast tumor cells.

These genetically engineered MCF-7 cells are plated in 96-well dishes (2000 cells/well) using RPMI medium without phenol red containing 10% charcoal-stripped FBS. To measure the effect of inhibiting P450arom on the cell proliferation, the substrate steroid A, and P450arom inhibitor are added to the cultures. The hormones are introduced 48 h after the plates are seeded with the cells. After 4 days, the treatments and media are refreshed. On day 10 after cell plating, the MTT dye is added to measure a viable cell count by colorimetric assay. The substrate A stimulates the growth of the MCF-7 cells in a concentration-dependent manner, and is decreased by the ER antagonist, 4-hydroxytamoxifen. In addition, the P450arom inhibitor, letrozole, inhibits the growth of DHEA-stimulated cell growth. These proliferation studies support the presence of active P450arom, 3β-HSD1 and STS in our MCF-7 cells. These preliminary data show that our MCF-7 cell system can be used to test the effects P450arom inhibitors on the rate of proliferation of human breast tumor cells.

I. Anticipated Outcome

We expect the optimization of known inhibitors based on the atomic structure of the binding site to yield inhibitors that are more exclusive for P450arom. Inclusion of chiral centers into non-steroidal inhibitors will produce chirality-specific inhibition exclusive for the target. De novo design ideas may need improvements through trial-and-error iterations. Test searches of the ZINC database with the known structure of human steroid sulfatase (STS) yielded 9436 potential ligands, from which 100 top-scoring compounds were selected for further analysis. Interestingly, the high scoring ZINC compounds with hydrophobic groups at the tail dock inside the cavity like the substrate E1-sulfate, while the extended hydrophobic tail interacts with hydrophobic residues at the lipid-protein interface. We expect that some of these predicted ligands are not only specific for binding at the lipid-protein interface near the STS active site, but also capable of crossing the plasma membrane. It is likely that the P450arom active site is also located near the lipid-protein interface. The anticipation is that screening of ZINC or similar compound libraries, coupled with incorporation of new design ideas, would yield high specificity inhibitors for P450arom.

J. Alternative Approaches

One drawback of virtual docking is that it sometimes yields false positive results. Therefore, the procedure has to be optimized by trial-and-error using experimentally observed binding modes. Other software routines, such as SYBYL, will be used for experimenting with consistency of docking results. The FlexX algorithm will be used for the purpose. The other major issue in virtual docking is whether or not to include flexibility of protein side chains and backbones. Again, we plan to conduct experiments with this option. Results from the FlexE routine that takes into account side chain flexibility will be compared with MOE results. Various protonation states for active site side chains will be explored. CScore will be used to rank the screening results. Effect on the scoring function of inclusion of any experimentally observed water molecules near the active site will be studied. As an alternative approach, a fragment-based docking procedure [94] will be initiated to generate de novo design ideas for non-steroidal inhibitors. Additionally, we will use the Glide docking routine [95, 96] (Schrödinger, Portland, Oreg.) for performing high-throughput screening of ligand libraries and induced-fit docking and scoring.

Example 11

Crystallization of the P450arom-P450 Reductase (CPR) Complex

A. Hypothesis, Rationale and General Approach

P450arom acts in conjunction with the flavoprotein cytochrome P450 reductase (CPR) that catalyzes the transfer of electrons from NADPH to all known microsomal cytochrome P450's. Although the crystal structure of the rat liver CPR has been known for sometime [97], the electron transport mechanism from CPR to P450's at the molecular level is still not understood. One of our long-term objectives is to conduct structural investigation on the P450arom-CPR enzyme complex in order to understand a complete microsomal cytochrome P450 enzyme system in the context of the aromatization reaction. Additionally, this provides an optimal platform for studying the molecular basis of a redox reaction by electron transfer. We routinely purify bovine (680 amino acids) and rat (678 amino acids) liver CPR's, both 92% identical to the human enzyme (677 amino acids), for the P450arom activity assay. Human placenta is also rich source of CPR. We have recently begun purifying the human CPR from placenta. However, because of low yield of the purified placental enzyme, we have now prepared an *E. coli* expression clone for the full-length human CPR following the protocol for the recombinant rat liver enzyme [97]. The expression and purification protocols are currently being optimized.

B. Expression and Purification of Recombinant Human CPR

Expression and purification will be performed using the procedure previously described. Optimization of the protein expression will be carried out at different cell growth and induction temperatures. The protein will be further purified by high-resolution ion exchange chromatography. Lastly, a hydroxyapatite column will be used to for the removal of NaCl and exchange of Triton X100 with 2 mM BNM (or 1 mM BDM), the detergent suitable for P450arom crystallization. The entire purification process will be performed at 4° C. on an AKTA FPLC system.

C. Crystallization of the P450arom-CPR Complex

Dilute solutions (~6 to 8 mg/ml, each ~0.1 mM) of equimolar amounts the enzymes in 100 mM K-phosphate buffer, pH 7.4, containing 20% glycerol, 0.1 mM EDTA, 0.1 mM andestenedione, 20 mM DTT, 2 mM NADPH and 2 mM BNM (or 1 mM BDM) will be incubated overnight at 4° C. The solution will then be concentrated roughly to 0.5 mM of each component and the crystallization trials will begin. First, we will conduct a fine screen around the condition at which P450arom was crystallized. We will also conduct a general screen of about 500 cocktail and buffer solutions.

D. Anticipated Outcome

There is a good probability that the complex will yield crystals under a condition similar to the crystallization condition of P450arom.

If the two enzymes fail to form a stable complex under the buffer conditions, it is unlikely that the complex crystal will ever grow. However, the probability of complex formation is higher at higher concentrations (>0.5 mM) of the proteins. The incubation of the components will then be carried out at the high concentration regime.

REFERENCES CITED

Citation of a reference herein shall not be construed as an admission that such reference is prior art to the present invention. All references cited herein are hereby incorporated by reference in their entirety. Below is a listing of references cited herein with reference number indicators:

A1. Briggs M H and Brotherton J (1970) Steroid Biochemistry and Pharmacology. Academic Press, London and New York. pp 52-85.

A2. Sato R and Omura T (1978) Cytochrome P-450. Kodansha Ltd., Tokyo/Academic Press, NY.

A3. Nelson D R (2007) Cytochrome P450s in humans. (drnelson.utmem.edu/P450lect.htm)

A4. Miller W L (2005) Regulation of steroidogenesis by electron transfer. Endocrinology 146, 2544-2550.

A5. Shimozawa O, Sakaguchi M, Ogawa H, Harada N, Mihara K, Omura T. (1993) Core glycosylation of cytochrome P-450(arom). Evidence for localization of N terminus of microsomal cytochrome P-450 in the lumen. J Biol. Chem. 268, 21399-21402.

A6. Amarneh B, Corbin C J, Peterson J A, Simpson E R, Graham-Lorence S (1993) Functional domains of human aromatase cytochrome P450 characterized by linear alignment and site-directed mutagenesis. Mol. Endocrinol. 7, 1617-1624.

A7. Simpson E R, Mahendroo, M. S., Means, G. D., Kilgore, M. W., Hinshelwood, M. M., Graham-Lorence, S., Amarneh, B., Ito, Y., Fisher, C. R., Michael, M. D., Meldenson, C. R., and Bulun, S. E. (1994) Aromatase cytochrome P450, the enzyme responsible for estrogen biosynthesis. Endocrine Reviews 15, 342-355.

A8. Poulos T L, Finzel B C and Howard A J (1987) High-resolution Crystal Structure of Cytochrome P450cam. J. Mol. Biol. 195, 697-700.

A9. Ravichandran K G, Boddupalli S S, Haserman C A, Peterson J A, and Deisenhofer J (1993) Crystal Structure of Hemoprotein Domain of P450BM-3, a Prototype for Microsomal P450s, Science 261, 731-736.

A10. Hasemann, C. A., Ravichandran, K. G., Peterson, J. A., and Deisenhofer, J. (1994) Crystal Structure and Refinement of P450terp at 2.3 Å Resolution, J. Mol. Biol., 236, 1169-1185.

A11. Cupp-Vickery, J. and Poulos, T. L. (1995) Structure of Cytochrome P450eryF: an Enzyme Involved in Erythromycin Biosynthesis, Nat. Struct. Biol., 2, 144-153.

A12. Williams P A, Cosme J, Ward A, Angove H C, Matak Vinković D, Jhoti H. (2003) Crystal structure of human cytochrome P450 2C9 with bound warfarin. Nature. 424, 464-468.

A13. Williams P A, Cosme J, Vinkovic D M, Ward A, Angove H C, Day P J, Vonrhein C, Tickle I J, Jhoti H. (2004) Crystal structures of human cytochrome P450 3A4 bound to metyrapone and progesterone. Science 305, 683-686

A14. Rowland P, Blaney F E, Smyth M G, Jones J J, Leydon V R, Oxbrow A K, Lewis C J, Tennant M G, Modi S, Eggleston D S, Chenery R J, Bridges A M. (2006) Crystal structure of human cytochrome P450 2D6. J Biol. Chem. 281, 7614-7622.

A15. Sansen, S., Yano, J. K., Reynald, R. L., Schoch, G. A., Griffin, K. J., Stout, C. D., Johnson, E. F. (2007) Adaptations for the Oxidation of Polycyclic Aromatic Hydrocarbons Exhibited by the Structure of Human P450 1A2. J Biol. Chem. 282, 14348-14355.

A16. Smith B D, Sanders J L, Porubsky P R, Lushington G H, Stout C D, Scott E E. (2007) Structure of the human lung cytochrome P450 2A13. J Biol. Chem. 282, 17306-17313

A17. Osawa Y, Higashiyama T, Fronckowiak M, Yoshida N, Yarborough C. (1987) Aromatase. J Steroid Biochem. 27, 781-789.

A18. Chen S, Zhang F, Sherman M A, Kijima I, Cho M, Yuan Y C, Toma Y, Osawa Y, Zhou D, Eng E T. Structure-function studies of aromatase and its inhibitors: a progress report. (2003) J Steroid Biochem Mol. Biol. 86, 231-237

A19. Zhou D J, Pompon D, Chen S A. (1991) Structure-function studies of human aromatase by site-directed mutagenesis: kinetic properties of mutants Pro-308-Phe, Tyr-361-Phe, Tyr-361-Leu, and Phe-406-Arg. Proc Natl Acad Sci USA. 88, 410-414.

A20. Akhtar M, Calder D L, Corina, D L, Wright J N (1982) Mechanistic studies on C19-demethylation in oestrogen biosynthesis. Biochem. J. 201, 569-580.

A21. Akhtar M, Njar V C, Wright J N. (1993) Mechanistic studies on aromatase and related C—C bond cleaving P-450 enzymes. J Steroid Biochem Mol. Biol. 44, 375-387.

A22. Laughton C A, Zvelebil M J, Neidle S. (1993) A detailed molecular model for human aromatase. J Steroid Biochem Mol. Biol. 44, 399-407.

A23. Chen S, Zhou D, Swiderek K M, Kadohama N, Osawa Y, Hall P F. (1993) Structure-function studies of human aromatase. J Steroid Biochem Mol. Biol. 44, 347-356.

A24. Oh, S. S. and Robinson, C. H. (1993) Mechanism of human placental aromatase: a new active site model. J. Steroid Biochem. Molec. Biol. 44, 389-397.

A25. Kadohama N, Zhou D, Chen S, Osawa Y. (1993) Catalytic efficiency of expressed aromatase following site-directed mutagenesis. Biochim Biophys Acta. 1993 May 13; 1163(2):195-200.

A26. Zhou D, Cam L L, Laughton C A, Korzekwa K R, Chen S (1994) Mutagenesis study at a postulated hydrophobic region near the active site of aromatase cytochrome P450. J Biol. Chem. 269, 19501-19508.

A27. Graham-Lorence S, Amameh B, White R E, Peterson J A, Simpson E R (1995) A three-dimensional model of aromatase cytochrome P450. Protein Sci. 4, 1065-1080.

A28. Kao Y C, Korzekwa K R, Laughton C A, Chen S (2001) Evaluation of the mechanism of aromatase cytochrome P450. A site-directed mutagenesis study. Eur J. Biochem. 268, 243-251.

A29. Hong Y, Yu B, Sherman M, Yuan Y C, Zhou D, Chen S (2007) Molecular basis for the aromatization reaction and exemestane-mediated irreversible inhibition of human aromatase. Mol. Endocrinol. 21, 401-414.

A30. Hong Y, Cho M, Yuan Y C, Chen S (2008) Molecular basis for the interaction of four different classes of substrates and inhibitors with human aromatase. Biochem Pharmacol. 75, 1161-1169

A31. Brueggemeier R W (2006) Update on the use of aromatase inhibitors in breast cancer. Expert Opin Pharmacother. 7, 1919-1930.

A32. Eisen A, Trudeau M, Shelley W, Messersmith H, Pritchard K I (2008) Aromatase inhibitors in adjuvant therapy for hormone receptor positive breast cancer: A systematic review. Cancer Treat Rev. 2007 Dec. 28; [Epub ahead of print]

A33. Nakajin S, Shinoda M, Hall P F (1986) Purification to homogeneity of aromatase from human placenta. Biochem Biophys Res Commun. 134, 704-710.

A34. Kellis J T, Vickery L E (1987) Purification and characterization of human placental aromatase cytochrome P-450. J. Biol. Chem. 262, 4413-4420.

A35. Yoshida N and Osawa Y (1991) Purification of Human Placental Aromatase Cytochrome P-450 with Monoclonal Antibody and Its Characterization. Biochemistry 30, 3003-3010.

A36. Amarneh B, Simpson E R (1995) Expression of a recombinant derivative of human aromatase P450 in insect cells utilizing the baculovirus vector system. Mol Cell Endocrinol. 109, R1-5.

A37. Lala P, Higashiyama T, Erman M, Griswold J, Wagner T, Osawa Y and Ghosh D (2004) Suppression of human cytochrome P450 aromatase activity by monoclonal and recombinant antibody fragments and identification of their stable antigenic complex. J. Steroid Biochem. Mol. Biol. 88, 235-245.

A38. Otninowski Z, Minor W (1995) The HKL Program Suit, In: HKL Manual, Yale University, New Haven, Conn.

A39. Collaborative Computational Project, Number 4. "The CCP4 Suite: Programs for Protein Crystallography" (1994) Acta Cryst. D50, 760-763.

A40. Emsley P, Cowtan K (2004) Coot: model building tools for molecular graphics. Acta Crystallogr. D 60, 2126-2132.

A41. Murshudov G N, Vagin A A, Dodson E J (1997) Refinement of Macromolecular Structures by the Maximum-Likelihood Method. Acta Cryst. D53, 240-255.

A42. Guallar V, Baik M H, Lippard S J, Friesner R A (2003) Peripheral heme substituents control the hydrogen-atom abstraction chemistry in cytochromes P450. Proc. Natl. Acad. Sci. USA. 100, 6998-7002.

A43. Nagano S, Poulos T L (2005) Crystallographic study on the dioxygen complex of wild-type and mutant cytochrome P450cam. Implications for the dioxygen activation mechanism. J. Biol. Chem. 280, 31659-31663.

A44. Nagano S, Cupp-Vickery J R, Poulos T L (2005) Crystal structures of the ferrous dioxygen complex of wild-type cytochrome P450eryF and its mutants, A245S and A245T: investigation of the proton transfer system in P450eryF. J. Biol. Chem. 22102-22107.

A45. Hackett J C, Brueggemeier R W, Hadad C M (2005) The final catalytic step of cytochrome P450 aromatase: a density functional theory study. J. Am. Chem. Soc. 127, 5224-5237.

A46. Pettersen E F, Goddard T D, Huang C C, Couch G S, Greenblatt D M, Meng E C, and Ferrin T E (2004) UCSF Chimera—A Visualization System for Exploratory Research and Analysis. J. Comput. Chem. 25, 1605-1612.

A47. Cojocaru V, Winn P J, Wade R C (2007) The ins and outs of cytochrome P450s. Biochim. Biophys. Acta 1770, 390-401.

A48. Shimozawa O, Sakaguchi M, Ogawa H, Harada N, Mihara K, Omura T (1993) Core glycosylation of cytochrome P-450(arom). Evidence for localization of N terminus of microsomal cytochrome P-450 in the lumen. J. Biol. Chem. 268: 21399-21402.

A49. Hernandez-Guzman F G, Higashiyama T, Pangborn W, Osawa Y, Ghosh D. (2003) Structure of human estrone sulfatase suggests functional roles of membrane association. J Biol. Chem. 278, 22989-22997.

3. Sato, R. and Omura, T. (1978) Cytochrome P-450. Kodansha Ltd., Tokyo/Academic Press, NY.

20. Kellis, J. T. and Vickery, L. E. (1987) Purification and Characterization of Human Placental Aromatase Cytochrome P-450, J. Biol. Chem., 262, 4413-4420.

50. Washida, N., Kitawaki, J., Higashiyama, T., Matsui, S., and Osawa, Y. (1996) Preparation of an Activity-Inhibiting Monoclonal Antibody Against Human Placental Aromatase Cytochrome P450, Steroids 61, 126-132.

51. Lala, P., Higashiyama, T., Erman, M., Griswold, J., Wagner, T., Osawa, Y. and Ghosh, D. (2004) Suppression of human cytochrome P450 aromatase activity by monoclonal and recombinant antibody fragments and identification of their stable antigenic complex. J. Steroid Biochem. Mol. Biol. 88, 235-245.

52. Otninowski, Z. and Minor, W. (1995) The HKL Program Suit, In: HKL Manual, Yale University, New Haven, Conn. Collaborative Computational Project, Number 4. 1994.

53. "The CCP4 Suite: Programs for Protein Crystallography". Acta Cryst. D50, 760-763

54. Emsley P and Cowtan K. (2004) Coot: model building tools for molecular graphics. Acta Crystallogr. D 60, 2126-2132.

55. Murshudov G N, Vagin A A and Dodson E J (1997) Refinement of Macromolecular Structures by the Maximum-Likelihood Method. Acta Cryst. D53, 240-255.

56. Chang, C.-C., Hernandez-Guzman, F. G., Luo, W., Wang, X., Ferrone, S, and Ghosh, D. (2005) Structural basis of antigen mimicry by an anti-idiotypic antibody in a human melanoma antigen system. J. Biol. Chem. 280, 41546-41552.

57. Gartner, C. A., Thompson, S. J., Rettie, A. E. and Nelson, S. D. (2001) Human aromatase in high yield and purity by perfusion chromatography and its characterization by difference spectroscopy and mass spectrometry. Protein Expr. Purif. 22, 443-54

58. Kagawa N, Hori H, Waterman M R, Yoshioka S. (2004) Characterization of stable human aromatase expressed in E. coli. Steroids 69, 235-43.

59. Chen, S., Zhou, D., Swiderek, K. M. Kadohama, N., Osawa, Y., and Hall, P. F. (1993) Structure-Function Studies of Aromatase, J. Steroid Biochem & Molecular Biol., 44, 347-356.

60. Sigle, R. O., Titus, M. A., Harada, N., and Nelson, S. D. (1994) Baculovirus Mediated High Level Expression of Human Placental Aromatase (CYP19A1), Biochem. Biophys. Res. Commun., 201, 694-700.

61. Amameh, B. and Simpson, E. R. (1995) Expression of a Recombinant Derivative of Human Aromatase P450 in Insect Cells Utilizing the Baculovirus Vector System, Mol. Cell. Endocrinol., 109, R1-R5.

62. Kurisu, G., Zhang, H., Smith, J. L. and Cramer, W. A. (2003) Structure of the cytochrome b6f complex of oxygenic photosynthesis: tuning the cavity. Science. 302(5647), 1009-1014.

63. Luft, J. R. et al., and DeTitta, G. T. (1994) A macromolecular crystallization procedure employing diffusion cells of varying depths as reservoirs to tailor the time course of equilibration in hanging- and sitting-drop vapor-diffusion and microdialysis experiments. J. Appl. Cryst. 27, 443-452.

64. Leslie, A. G. (2006) The integration of macromolecular diffraction data. Acta Crystallogr D Biol Crystallogr. 62 (Pt 1), 48-57.

65. Ghosh, D., Sawicki, M., Pletnev, V., Erman, M., Ohno, S., Nakajin, S., and Duax, W. L. (2001) Porcine Carbonyl Reductase: Structural Basis for a Functional Monomer in Short-chain Dehydrogenases/Reductases, J. Biol. Chem., 276, 18457-18463.

66. Sawicki, M. W., Ng, P. C., Burkhart, B. M., Pletnev, V. Z., Higashiyama, T., Osawa, Y. and Ghosh, D. (1999) Structure of an Activity Suppressing Fab Fragment to Cytochrome P450 Aromatase: Insights Into the Antibody-Antigen Interactions, Mol. Immunol. 36, 423-432.

67. MacRee, D. E. (1999) XtalView/Xfit—A versatile program for manipulating atomic coordinates and electron density. J Struct Biol. 125(2-3):156-65.

68. Sack, J. S. (1988) CHAIN. Mol. Graph. 6, 224-225.

69. Jones, A. T., Zhou, J.-Y., Cowan, S. W, and Kjeldgaard, M. (1991) Improved methods for building protein models in electron density maps and the location of errors in these models. Acta Crystallogr. A47, 110-119.

70. Brünger, A. T. (1992) X-PLOR, Version 3.1, User's Guide, Yale University, New Haven, 71. Brünger, A. T. et al. and Warren, G. L. (1998) Crystallography & NMR system: A new software suite for macromolecular structure determination. Acta Crystallogr. D 54, 905-921.

72. Laskowski R A, MacArthur M W, Thornton J M. (1998) Validation of protein models derived from experiment. Curr Opin Struct Biol. 8, 631-639.

73. Hooft, R. W. W., Vriend, G., Sander, C. and Abola, E. E., (1996) Errors in protein structures. Nature 381, 272-272.

74. Ghosh, D., Erman, M., Sawicki, M., Lala, P., Weeks, D. R., Li, N., Pangborn, W., Thiel, D. J., Jörnvall, H., and Eyzaguirre, J. (1999) Determination of a Protein Structure by Iodination: The Structure of Iodinated Acetylxylan Esterase. Acta Crystallogr. D., Biological Crystallography, D55, 779-784.

75. Brueggemeier, R. W., Hackett, J. C. and Diaz-Cruz, E. S. (2005) Aromatase inhibitors in the treatment of breast cancer. Endocrine Reviews 26, 331-345.

76. Brodie, A. (2002) Aromatase Inhibitors and the Application to the Treatment of Breast Cancer. In: Breast Cancer: Prognosis, Treatment and Prevention, ed. Jorge Pasqualini, Chapter 8, pp. 251-270, Marcel Dekker, NY.

77. Ghosh, D., Erman, M., Wawrzak, Z., Duax, W. L., and Pangborn, W. (1994) Mechanism of Inhibition of 3α,20β-Hydroxysteroid Dehydrogenase by a Licorice-Derived Steroidal Inhibitor, Structure 2, 973-980 (1994).

78. Berglund, G. I., Carlsson, G. H., Smith, A. T., Szoke, H., Herriksen, A. and Hajdu, J. (2002) The catalytic pathway of horseradish peroxidase at high resolution. Nature 417, 463-468.

79. Schlichting, I., Berendzen, J., Chu, K., Stock, A. M., Maves, S. A., Benson, D. E., Sweet, R. M., Ringe, D., Petsko, G. A. and Sligar, S. G. (2000) The catalytic pathway of cytochrome p450cam at atomic resolution. Science. 287, 1615-1622.

80. Davies, H. M. L. and Loe, O (2004) Intermolecular C—H Insertions of Donor/Acceptor-Substituted Rhodium Carbenoids: A Practical Solution for Catalytic Enantioselective C—H Activation, Synthesis, 2595-2608.

81. Davies, H. M. L. and Nikolai, J. (2005) Catalytic and Enantioselective Allylic C—H Activation with Donor/Acceptor-Substituted Carbenoids, Org. Bio. Chem. 3, 4176-4187.

82. Davies, H. M. L., Beckwith, R. E. J., Antoulinakis, E. G. and Jin, Q. (2003) New strategic reactions for organic synthesis: catalytic asymmetric C—H activation α to oxygen as a surrogate to the aldol reaction, J. Org. Chem. 68, 6126-6132.
83. Davies, H. M. L., Bruzinski, P., Hutcheson, D. K. and Fall, M. J. (1996) Asymmetric Cyclopropanations by Rhodium (II) N-(Arylsulfonyl)prolinate Catalyzed Decomposition of Vinyldiazomethanes in the Presence of Alkenes. Practical Enantioselective Synthesis of the Four Stereoisomers of 2-Phenylcyclopropane-1-amino Acid, J. Am. Chem. Soc. 118, 6897-6907.
84. Ni, A., France, J. and Davies, H. M. L. (2006) Diversity synthesis using the complimentary reactivity of rhodium (II)- and palladium(I)-catalyzed reactions, J. Org. Chem. 71, 5594-5598.
85. Davies, H. M. L., Nagashima, T. and Klino, J., III (2000) Stereoselectivity of Methyl Aryldiazoacetate Cyclopropanations of 1,1-Diarylethyles. Asymmetric Synthesis of a Cyclopropyl Analog of Tamoxifen. Org. Lett. 2, 823-826.
86. Cummings, M. D., DesJarlais, R. L., Gibbs, A. C., Mohan, V. and Jaeger, E. P. (2005) Comparison of automated docking programs as virtual screening tools. J. Med. Chem. 48, 962-976.
87. Lipinski, C. A., Lombardo, F., Dominy, B. W., Feeney, P. J. (1997) Experimental and computational approaches to estimate solubility and permeability in drug discovery and development settings", Adv. Drug Delivery Rev., 1997, 23, 3-25.
88. Kontoyianni, M., Sokol, G. S, and Mcclellan, L. M. (2005) Evaluation of library ranking efficacy in virtual screening. J. Comput. Chem. 26, 11-22.
89. Gohlke, H.; Hendlich, M.; Klebe, G. (2000) Predicting binding modes, binding affinities and 'hot spots' for protein-ligand complexes using a knowledge-based scoring function. *Perspect. Drug Discovery Des* 20, 115-144
90. SuperStar—Predicting Protein-Ligand Interactions Using Experimental Data, 2004 The Cambridge Crystallographic Data Centre
91. Velec, H. F. G., Gohlke, H. and Klebe, G. (2005) Drug-Score$^{CSD}$-Knowledge-Based Scoring Function Derived from Small Molecule Crystal Data with Superior Recognition Rate of Near-Native Ligand Poses and Better Affinity Prediction. J. Med. Chem. 48, 6296-630
92. Thomas J L, Umland T C, Scaccia L A, Boswell E L and Kacsoh B (2004) The higher affinity of human type 1 3β-hydroxysteroid dehydrogenase (30-HSD1) for substrate and inhibitor steroids relative to human 3β-HSD2 is validated in MCF-7 tumor cells and related to subunit interactions. *Endocrine Res*, 30, 935-941.
93. Thomas J. L., Ghosh, D., Scaccia L. A. and Kacsoh, B. (2006) A human breast tumor MCF-7 cell line with endogenous steroid sulfatase and stably transfected with human 3β-hydroxysteroid dehydrogenase type 1 and aromatase creates a new model system that measures the effect of enzyme inhibitors on tumor cell proliferation. The 88th Annual Meeting of the Endocrine Society. June 24-27, Boston, Mass., 2006.
94. Hartshorn, M. J. et al. and Jhoti, H. (2005) Fragments-based lead discovery using X-ray crystallography. J. Med. Chem. 48, 403-413.
95. Halgren, T. A. et al. and Banks, J. L. (2004) Glide: a new approach for rapid, accurate docking and scoring. 2. Enrichment factors in database screening. J. Med. Chem. 47, 1750-1759
96. Friesner, R. A. et al. and Shenkin, P.S. (2004) Glide: A New Approach for Rapid, Accurate Docking and Scoring. 1. Method and Assessment of Docking Accuracy. J. Med. Chem. 47, 1739-1749.
97. Wang, M., Roberts, D. L., Paschke, R., Shea, T. M., Masters, B. S. S. and Kim, J.-J. P. (1997) Three-dimensional structure of NADPH-cytochrome P450 reductase: prototype for FMN- and FAD-containing enzymes. Proc. Natl. Acad. Sci. USA 94, 8411-8416.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A crystal comprising a human aromatase in complex with a ligand, wherein said ligand is bound to a ligand binding site of said human aromatase, wherein the amino acid sequence of said human aromatase is SEQ ID NO:1, and wherein said crystal is in a space group of P3$_2$21 and has unit cell parameters of a=b=140.2 Å, c=119.3 Å, α=β=90°, and γ=120°.

2. A crystal according to claim 1, wherein the ligand binding site is the active/substrate-binding site.

3. A crystal according to claim 2, wherein said active/substrate-binding site comprises amino acid residues Arg115 through Phe147, Ile217 through Leu228, Leu301 through Ser314, Pro368 through Arg375, and Ile474 through His480 of SEQ ID NO:1.

4. A crystal according to claim 2, wherein said aromatase comprises a heme proximal/P450 reductase coupling site comprises amino acid residues Arg145 through Met149, Glu357 through Met364, and Pro423 through Met447 of SEQ ID NO:1.

5. A crystal according to claim 1, wherein said aromatase comprises an active site access channel comprising amino acid residues Asp186 through Arg192, Gln218 through Leu228, Pro308 through Phe317, Pro368 through Leu372, and Gln472 through Lys485 of SEQ ID NO:1.

6. A crystal according to claim 1, wherein the x-ray diffraction pattern of the crystal is solved to produce a three-dimensional structure described by atomic coordinates comprising:
  atomic coordinates 553 through 821, 1359 through 1459, 2062 through 2161, 2611 through 2673, and 3468 through 3535 as set forth in Appendix A;
  atomic coordinates 1112 through 1179, 1367 through 1459, 2113 through 2191, 2611 through 2647, and 3450 through 3565 as set forth in Appendix A; and/or
  atomic coordinates 793 through 840, 2508 through 2578, and 3057 through 3257 as set forth in Appendix A.

7. A crystal according to claim 1, wherein the x-ray diffraction pattern of the crystal is solved to produce a three-dimensional structure described by the atomic coordinates as set forth in Appendix A.

8. The crystal according to claim 1, wherein said ligand is selected from the group consisting of an androgenic substrate of human aromatase, an androgenic substrate intermediate of human aromatase, and a competitive inhibitor of human aromatase.

9. The crystal according to claim 8, wherein the androgenic substrate of human aromatase is selected from the group consisting of androstenedione, testosterone, and 16α-hydroxytestosterone.

10. The crystal according to claim 8, wherein the androgenic substrate intermediate of human aromatase is selected from the group consisting of 19-hydroxyandrostenedione, 19-aldoandrostenedione, and 19-hydroxytestosterone.

11. The crystal according to claim 8, wherein the competitive inhibitor of human aromatase is selected from the group consisting of exemestane, letrozole, anastrazole, formestane, fadrozole, and aminoglutethimide.

12. The crystal according to claim 2, wherein said active/substrate-binding site comprises amino acid residues selected from the group consisting of Arg115, Ile133, Phe134, Phe221, Trp224, Ala306, Asp309, Thr310, Val370, Val373, Met374, and Leu477 of SEQ ID NO:1.

13. The crystal according to claim 2, wherein the active/substrate-binding site comprises a catalytic cleft comprising amino acid residues selected from the group consisting of Ile133, Phe134, Ile305, Ala306, Asp 309, Thr310, Val370, Leu372, Val373, Met374, Leu477, and Ser478 of SEQ ID NO:1.

14. The crystal according to claim 2, wherein the active/substrate-binding site comprises amino acid residues selected from the group consisting of Arg192, Gln218, Gln225, Leu228, Pro308, Met311, and Glu483 of SEQ ID NO:1.

15. The crystal according to claim 2, wherein the active/substrate-binding site comprises three-dimensional regions selected from the group consisting of:
  an I-helix comprising Ile305, Ala306, Asp309, and Thr310 of SEQ ID NO:1;
  a B-C loop comprising Ile133 and Phe 134 of SEQ ID NO:1;
  a K-helix-β3-loop comprising Val370, Leu372, and Val373 of SEQ ID NO:1;
  a β3 segment comprising Met374 of SEQ ID NO:1; and
  a β8-β9 loop comprising Leu477 and Ser378 of SEQ ID NO:1.

16. The crystal according to claim 1, wherein the aromatase has an access channel having an interior protein border comprising at least amino acid residues Arg192, Asp309, Ser478, and Glu483 of SEQ ID NO:1.

17. The crystal according to claim 2, wherein the ligand is an androstenedione bound to the active/substrate-binding site of the human aromatase, and wherein the crystal diffracts x-ray to a resolution of 2.90 Å or better.

18. A composition comprising the crystal according to claim 1.

19. A composition comprising the crystal according to claim 2.

20. A method for crystallizing a human aromatase, the method comprising:
  providing a protein solution comprising the human aromatase of SEQ ID NO:1 with a ligand in a first solution, wherein said first solution comprises 100 mM K-phosphate buffer, pH 7.4, containing 20% glycerol, 0.1 mM EDTA, 0.1 mM A, and either 2 mM n-nonyl-β-D-maltopyranoside (BNM) or 1 mM n-dodecyl-β-D-maltopyranoside (BDM);
  combining the protein solution with a second solution, wherein said second solution comprises 24 to 30% polyethylene glycol (PEG) 4000 in 50 mM Tris-HCl buffer, pH 8.5, containing 0.5 M NaCl, in the ratios of 1:1, 2:1 and 3:1, and wherein said providing and combining steps are conducted at about 4° C.; and
  incubating the resulting solution at 4° C. to yield a crystallized human aromatase in complex with the ligand.

21. The method according to claim 20, wherein said DTT is present during crystallization at a concentration of between about 10 mM and 20 mM.

22. A crystallized human aromatase provided by the method of claim 20.

23. A method for obtaining a three dimensional structure of a human aromatase, said method comprising:
  (a) obtaining a crystal comprising a human aromatase in complex with a ligand, wherein said ligand is bound to a ligand binding site of said human aromatase, wherein the amino acid sequence of said human aromatase is SEQ ID NO:1, and wherein said crystal is in a space group of P3$_2$21 and has unit cell parameters of a=b=140.2 Å, c=119.3 Å, α=β=90°, and γ=120°;
  (b) using the crystal obtained in step (a) to obtain an x-ray diffraction pattern; and
  (c) solving the three dimensional structure of the human aromatase from the diffraction pattern obtained in step (b), thereby obtaining the three dimensional structure of the human aromatase.

24. A method for identifying a compound that binds to a human aromatase, said method comprising:
  (a) obtaining a crystal comprising a human aromatase in complex with a ligand, wherein said ligand is bound to a ligand binding site of said human aromatase, wherein the amino acid sequence of said human aromatase is SEQ ID NO:1, and wherein said crystal is in a space group of $P3_221$ and has unit cell parameters of $a=b=140.2$ Å, $c=119.3$ Å, $\alpha=\beta=90°$, and $\gamma=120°$;
  (b) using the crystal obtained in step (a) to obtain an x-ray diffraction pattern;
  (c) solving the three dimensional structure of the human aromatase from the diffraction pattern obtained in step (b), thereby obtaining the three dimensional structure of the human aromatase; and
  (d) identifying one or more compounds that binds to the human aromatase based on the three dimensional structure.

25. The method according to claim 24 further comprising:
  contacting one or more compounds identified in step (d) with the human aromatase of SEQ ID NO:1, and determining the binding of one or more compound to said aromatase.

26. The method according to claim 24 further comprising:
  contacting one or more compounds identified in step (d) with the human aromatase of SEQ ID NO:1;
  measuring the activity of the human aromatase of SEQ ID NO:1; and
  comrparing the activity of said aromatase in the presence and absence of said one or more compounds. wherein compounds found to decrease the aromatase activity are identified as aromatase inhibitors.

27. The method according to claim 26 further comprising:
  comparing the inhibitory activities of inhibitors of the human aromatase of SEQ ID NO:1.

28. The method according to claim 24 further comprising:
  contacting one or more compounds identified in step (d) with a cell that expresses a human aromatase of SEQ ID NO:1; and
  detecting whether a phenotype of the cell changes when the one or more compounds are present.

* * * * *

UNITED STATES PATENT AND TRADEMARK OFFICE
CERTIFICATE OF CORRECTION

PATENT NO. : 7,687,252 B2  Page 1 of 1
APPLICATION NO. : 12/265709
DATED : March 30, 2010
INVENTOR(S) : Debashis Ghosh It is certified that error appears in the above-identified patent and that said Letters Patent is hereby corrected as shown below:

Claim 26, at Column 64, Line 7: Delete "comrparing the activity" and insert --comparing the activity--

Signed and Sealed this

Twenty-ninth Day of June, 2010

David J. Kappos
*Director of the United States Patent and Trademark Office*